US012558517B2

(12) United States Patent
Martin

(10) Patent No.: US 12,558,517 B2
(45) Date of Patent: Feb. 24, 2026

(54) CATHETER CONSTRUCTION

(71) Applicant: Maduro Discovery, LLC, Campbell, CA (US)

(72) Inventor: Brian B. Martin, Santa Cruz, CA (US)

(73) Assignee: Maduro Discovery, LLC, Los Gatos, CA (US)

( * ) Notice: Subject to any disclaimer, the term of this patent is extended or adjusted under 35 U.S.C. 154(b) by 0 days.

(21) Appl. No.: 18/456,328

(22) Filed: Aug. 25, 2023

(65) Prior Publication Data

US 2024/0058575 A1 Feb. 22, 2024

Related U.S. Application Data

(63) Continuation of application No. PCT/US2023/071362, filed on Jul. 31, 2023.

(60) Provisional application No. 63/505,397, filed on May 31, 2023, provisional application No. 63/369,947, filed on Jul. 30, 2022.

(51) Int. Cl.
*A61M 25/00* (2006.01)

(52) U.S. Cl.
CPC .... *A61M 25/0053* (2013.01); *A61M 25/0023* (2013.01); *A61M 25/005* (2013.01); *A61M 25/0054* (2013.01); *A61M 25/008* (2013.01); *A61M 25/0067* (2013.01); *A61M 2025/0081* (2013.01)

(58) Field of Classification Search
CPC .......... A61M 25/0053; A61M 25/0023; A61M 25/005; A61M 25/0054; A61M 25/008; A61M 25/0067; A61M 25/0045; A61M 2025/0081
See application file for complete search history.

(56) References Cited

U.S. PATENT DOCUMENTS

| | | | |
|---|---|---|---|
| 5,176,660 A | 1/1993 | Truckai |
| 5,454,795 A | 10/1995 | Samson |
| 5,554,139 A | 9/1996 | Okajima |
| 5,639,409 A | 6/1997 | Van Muiden |
| 5,762,637 A | 6/1998 | Berg et al. |
| 5,769,830 A | 6/1998 | Parker |

(Continued)

FOREIGN PATENT DOCUMENTS

| | | |
|---|---|---|
| EP | 0715863 | 6/1996 |
| JP | 08-057035 | 8/1994 |

(Continued)

*Primary Examiner* — James D Ponton
*Assistant Examiner* — John A Doubrava
(74) *Attorney, Agent, or Firm* — Levine Bagade Han LLP

(57) ABSTRACT

Polymeric tubing, for use with catheters or other medical devices, where the polymeric tubing can have regions of customized properties including, but not limited to, durometer, torque control, flexibility, axial strength, stiffness, etc. One variation of the device allows for transitions between regions to be configured such that there can be gradual or customized transitions between various regions such that the structural characteristics differential between the regions selectively designed. Additional variations include outer layers having a plurality of material sections extending in a spiral direction along the axial length to form a continuous wall of the outer layer. In certain variations, the structural characteristic differential is minimized or eliminated as compared to conventional catheters.

20 Claims, 50 Drawing Sheets

(56)                    References Cited

U.S. PATENT DOCUMENTS

| | | | |
|---|---|---|---|
| 5,795,341 | A | 8/1998 | Samson |
| 5,827,201 | A | 10/1998 | Samson et al. |
| 5,876,386 | A | 3/1999 | Samson |
| 5,891,114 | A | 4/1999 | Chien et al. |
| 5,947,940 | A | 9/1999 | Beisel |
| 5,951,539 | A | 9/1999 | Nita et al. |
| 5,976,120 | A | 11/1999 | Chow et al. |
| 6,143,013 | A | 11/2000 | Samson et al. |
| 6,146,814 | A | 11/2000 | Millet |
| 6,368,316 | B1 | 4/2002 | Jansen et al. |
| 6,425,908 | B2 | 7/2002 | Ravenscroft et al. |
| 6,858,024 | B1 | 2/2005 | Berg et al. |
| 7,025,758 | B2 | 4/2006 | Klint |
| 7,279,208 | B1 | 10/2007 | Goffena et al. |
| 7,507,229 | B2 | 3/2009 | Hewitt et al. |
| 7,716,705 | B2 | 5/2010 | Berger et al. |
| 8,377,035 | B2 | 2/2013 | Zhou et al. |
| 10,512,753 | B1 | 12/2019 | Nguyen |
| 10,610,666 | B2 | 4/2020 | Stern |
| 10,898,683 | B2 | 1/2021 | Martin |
| 11,077,285 | B2 | 8/2021 | Martin |
| 11,179,546 | B2 | 11/2021 | Martin |
| 11,865,273 | B2 | 1/2024 | Martin |
| 12,350,447 | B1 | 7/2025 | Martin |
| 2002/0032408 | A1 | 3/2002 | Parker et al. |
| 2002/0183781 | A1 | 12/2002 | Casey |
| 2004/0002727 | A1 | 1/2004 | Hwang et al. |
| 2005/0137519 | A1 | 6/2005 | Boismier |
| 2005/0215942 | A1 | 9/2005 | Abrahamson et al. |
| 2006/0136032 | A1 | 6/2006 | Legarda et al. |
| 2006/0264905 | A1 | 11/2006 | Eskridge et al. |
| 2007/0233040 | A1 | 10/2007 | Macnamara et al. |
| 2009/0198219 | A1 | 8/2009 | Campbell et al. |
| 2010/0030165 | A1 | 2/2010 | Takagi et al. |
| 2011/0172643 | A1 | 7/2011 | Jansen et al. |
| 2012/0101480 | A1 | 4/2012 | Ingle et al. |
| 2017/0072163 | A1 | 3/2017 | Lim et al. |
| 2017/0182290 | A1 | 6/2017 | Stern |
| 2018/0289925 | A1 | 10/2018 | Palmer et al. |
| 2018/0361116 | A1 | 12/2018 | Quick et al. |
| 2019/0117385 | A1 | 4/2019 | Atlani et al. |
| 2019/0134348 | A1 | 5/2019 | Wada |
| 2019/0351182 | A1 | 11/2019 | Chou et al. |
| 2020/0391009 | A1* | 12/2020 | Martin .............. A61M 25/0053 |
| 2021/0001079 | A1 | 1/2021 | Martin |
| 2021/0162176 | A1 | 6/2021 | Martin |
| 2021/0290907 | A1 | 9/2021 | Martin |
| 2021/0308416 | A1 | 10/2021 | Ito et al. |
| 2021/0393277 | A1 | 12/2021 | Vale et al. |
| 2022/0008692 | A1 | 1/2022 | Pulugurtha et al. |
| 2023/0390524 | A1 | 12/2023 | Martin |
| 2023/0390525 | A1 | 12/2023 | Martin |
| 2023/0390526 | A1 | 12/2023 | Martin |
| 2024/0016596 | A1 | 1/2024 | Martin |
| 2024/0033469 | A1 | 2/2024 | Martin |
| 2024/0033476 | A1 | 2/2024 | Martin |
| 2024/0058576 | A1 | 2/2024 | Martin |
| 2024/0198043 | A1 | 6/2024 | Martin |
| 2024/0198044 | A1 | 6/2024 | Martin |
| 2024/0399107 | A1 | 12/2024 | Martin |
| 2025/0025665 | A1 | 1/2025 | Martin |
| 2025/0177701 | A1 | 6/2025 | Martin |

FOREIGN PATENT DOCUMENTS

| | | |
|---|---|---|
| JP | 11-114068 | 4/1999 |
| JP | 2001-079095 | 3/2001 |
| JP | 2001-137347 | 5/2001 |
| JP | 2006-515778 | 6/2006 |
| JP | 2007-260403 | 10/2007 |
| JP | 2009-060082 | 3/2009 |
| JP | 4547374 | 9/2010 |
| JP | 2012-213507 | 11/2012 |
| JP | 2015-144791 | 8/2015 |
| JP | 2017-202042 | 11/2017 |
| JP | 2018-526185 | 9/2018 |
| JP | 3181547 | 7/2021 |
| WO | WO 2006/096314 | 9/2006 |
| WO | WO 2020/257125 | 12/2020 |
| WO | WO 2024/030872 | 2/2024 |
| WO | WO 2024/040872 | 2/2024 |
| WO | WO 2024/138061 | 6/2024 |
| WO | WO 2024/249757 | 12/2024 |
| WO | WO 2025/019333 | 1/2025 |
| WO | WO 2025/193984 | 9/2025 |

* cited by examiner

255

203

245     263    245     235

263

203

270      255

263     255     203

245

330

332

334

336

338

340

230

232

342

344

346

348

230

232

290
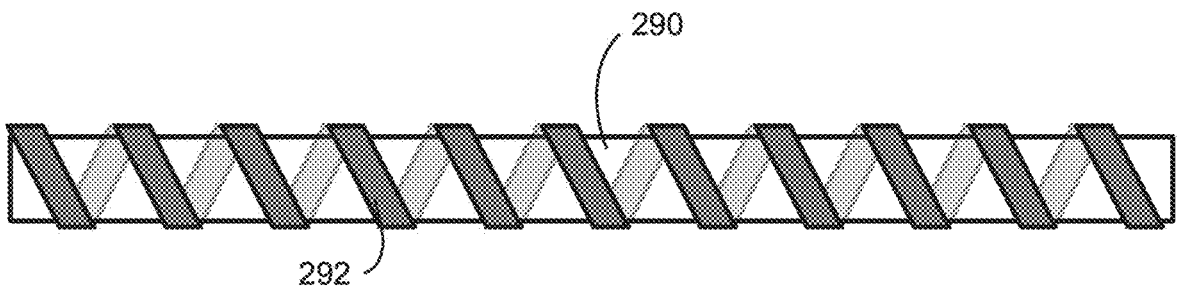
292
FIG. 14A
290　292　294
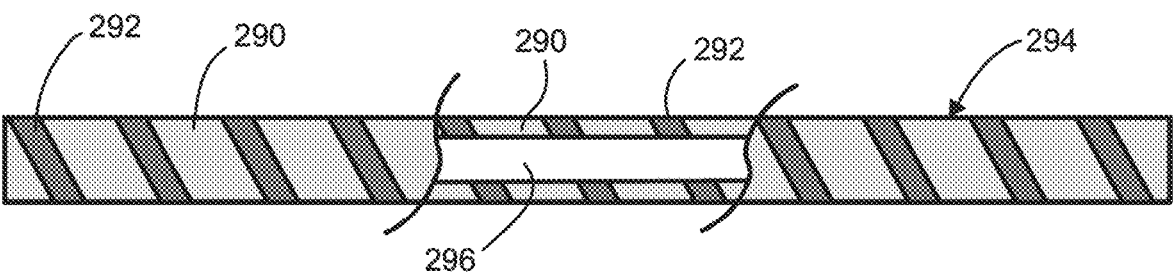
FIG. 14B
292　290　290　292　294
296
FIG. 14C

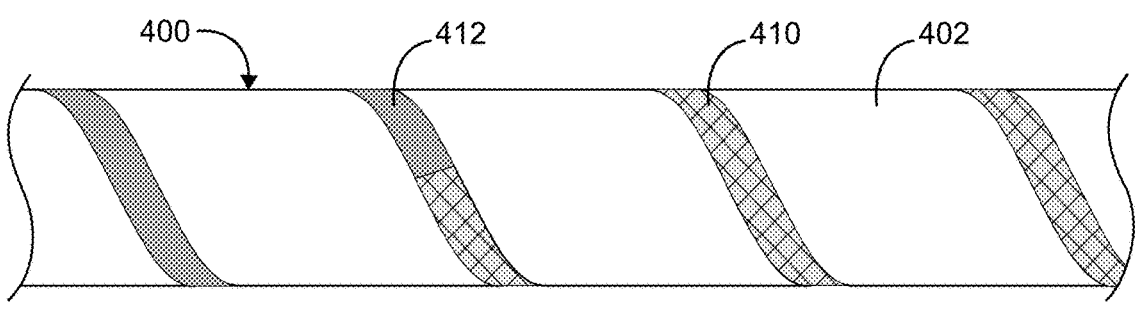
FIG. 23C
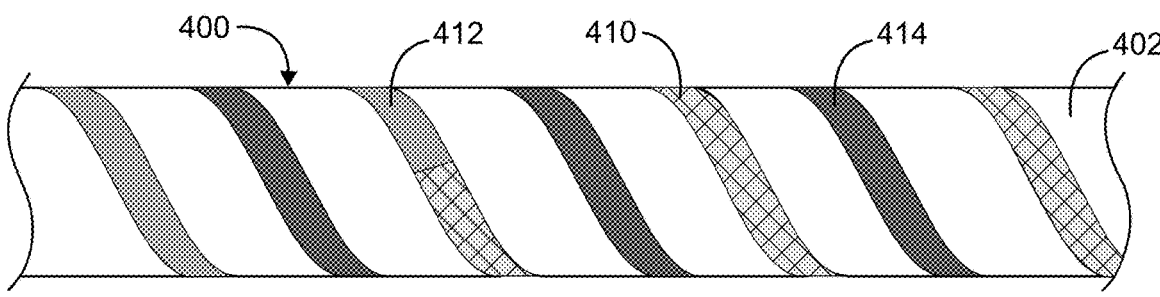
FIG. 23D
FIG. 23E

CATHETER CONSTRUCTION

CROSS-REFERENCE TO RELATED APPLICATIONS

This application is a continuation of PCT Application no. PCT/US2023/071362 filed on Jul. 31, 2023, which claims the benefit of U.S. provisional application No. 63/369,947, filed Jul. 30, 2022, and U.S. provisional application No. 63/505,397, filed May 31, 2023, the entirety of all of the preceding are incorporated by reference. This application is also a continuation in-part of U.S. patent application Ser. No. 18/451,646, filed Aug. 17, 2023, which is a continuation of U.S. patent application Ser. No. 17/303,833, filed Jun. 8, 2021 (U.S. Pat. No. 11,856,273), which is a continuation of U.S. patent application Ser. No. 17/173,003, filed Feb. 10, 2021 (U.S. Pat. No. 11,179,546), which is a divisional of U.S. patent application Ser. No. 16/902,154, filed Jun. 15, 2020 (U.S. Pat. No. 11,077,285), which claims the benefit of U.S. provisional application No. 62/862,035, filed on Jun. 15, 2019.

FIELD OF THE INVENTION

Polymeric tubing, for use with catheters or other medical devices, where the polymeric tubing can have lengths of customized properties including, but not limited to, durometer, torque control, flexibility, axial strength, stiffness, etc. In one variation, the transition regions between lengths can be configured such that there can be abrupt, gradual, or customized transition regions between various lengths such that the structural characteristics differential between the lengths and over the transition regions are selectively designed. In certain variations, the structural characteristic differential is minimized or eliminated as compared to conventional catheters.

BACKGROUND OF THE INVENTION

Medical catheters allow physicians to apply a variety of different therapies within the body of a patient. Many catheters access remote regions of the human body for delivering diagnostic or therapeutic tools and/or agents to those sites. Alternatively, the catheter can comprise a shaft or support for a therapeutic working end (e.g., balloon, filter retriever, electrode, etc.). Some catheters, including but not limited to catheters for neurovascular use, are intended to be advanced from a main artery (e.g., a femoral or radial artery) through tortuous anatomy into a small cerebral vessel. As such, the catheter must be configured with varying structural traits due to the varying regions of the anatomy through which the catheter passes. Many times, the vascular pathways wind back upon themselves in a multi-looped path making it difficult for catheter design to meet the requirements demanded by the tortuous anatomy. For example, catheters must be fairly stiff at their proximal end to allow the pushing and manipulation of the catheter as it progresses through the body, and yet must be sufficiently flexible at the distal end to allow passage of the catheter tip through the loops and smaller blood vessels. Regardless, the catheter must not cause significant trauma to the blood vessel or to the surrounding tissue.

FIG. 1A illustrates a traditional catheter construction and shows sectional views of a catheter section 10 that can be constructed on an inner mandrel or core 12 that is later removed. The traditional catheter construction includes a layer 14, such as PTFE, that provides a lubricious surface for the interior of the catheter while also supporting various structural components to provide varying sections 16 and 18 of the catheter 10. For example, the illustrated catheter 10 includes a reinforced section 16 in which a braid or coil 20 (or both) are wrapped around the second layer 14. Many catheters use metal braids in the proximal end of the catheter and metal coils in the distal end of the catheters (or one under the other).

Many catheters intended to navigate through tortuous anatomy also include regions with varying durometers 18 in which polymers of different durometers 22, 24, and 26 are placed next to each other. FIG. 1A is intended for illustrative purposes to show basic structures of conventional catheters. The catheter 10 of FIG. 1A shows polymer 22 terminates before a distal end 8 of the catheter 10 for illustrative purposes to only show the underlying reinforced section 16. In most conventional catheters, the entirety of the distal end is encapsulated by a polymer.

As shown in FIG. 1A, a series of adjacently placed polymer jackets 22, 24, 26 are placed over the reinforcement layer and fused into place (such as by heating and reflowing the polymer onto the braid or coil). Different polymer durometers (i.e., "stiffness") are used for different sections. As a result, each of these sections of catheter will have unique structural characteristics/properties, where the structural properties can include but are not limited to stiffnesses, resistance to twisting or torsion, flexibility, column strength, etc. The illustrated construction 10 provides for varying structural characteristics over the varying regions of the catheter. However, in conventional devices, such a catheter construction yields abrupt changes in characteristics at the transition or edge of each region 22, 24, 26.

In many conventional catheter devices, higher durometer polymers are used in the proximal region, with softer durometers placed as the catheter progresses toward the distal end. More sophisticated catheters have more "sections" or transitions of stiffness (i.e., more discreet pieces of extrusion of different durometers used for the outer jacket). For example, FIG. 1C shows a representation of an end of a Sofia® Plus Distal Access Catheter 19 manufactured by Microvention Termuo (Aliso Viejo, CA), which is an example of a commercially available intracranial catheter described by Microvention as having an "exceptionally soft distal tip" and "torqueable shaft" at the proximal length. The catheter includes an intermediate section 23 that is adjacent to a soft distal tip 25. The proximal length of the catheter isn't shown since FIG. 1C is intended to show that the intermediate length 23 is constructed from a relatively higher durometer polymer and has an abrupt transition to the relatively softer distal tip 25. Typically, a higher durometer polymer provides improved torque, rotational/axial stability but poor flexibility. As shown in FIG. 1C, a push force applied at the harder durometer polymer proximal end can cause area 38 to buckle, which is approximately where the polymers change. The buckling results in even worse push and navigation.

Typically, stiffer durometers are more suitable for the proximal region of the catheter. Although stiffer durometer polymers do not bend as well around curves, they have greater positional stability in the vessels and tend to transmit torque well. In contrast, softer durometers are suitable for the distal region of the catheter; because these polymers bend more easily and gently around the more delicate and tortuous distal curves. However, softer durometer polymers do not transmit torque well and have poor positional stability. Thus, conventional catheter designs use a "balancing act" between mechanical properties, where the design elements (stiff and stable vs soft and less stable) are compromised. Additionally, the change from one durometer to another has long been a source of mechanical challenge. These transitions are a source of discontinuity and are known in the field to cause challenges in torque transmission and can lead to irregularities in bending stress which leads to poor navigation in the anatomy. As such, engineers attempt to make the transitions as long and gradual as possible and to mitigate abrupt changes by having numerous small transitions as opposed to fewer larger transitions.

Regardless of the length of the transitions, the traditional construction, as shown in FIG. 1A relies on the braid or coil 20 (or both) used to transmit torque as the catheter navigates through tortuous anatomy. However, since the polymers 22, 24, 26 (etc.) are exterior to the braid/coil 20, a greater degree of torque is applied to the polymers. Polymers having different physical properties will also have different resistance to torque. For example, in a variation where polymers 22, 24, and 26 have decreasing flexibility (22 being the most flexible and 26 being the least), torque applied by the rotation of section 26 will not be fully applied to section 24. Therefore, section 24 will not rotate as much as section 26. The same effect will occur with section 22; its rotation will not be as much as section 24 and even less than section 26. This results in poor torque control or torque instability. Furthermore, when these sections are flexed, the transition between polymers creates discontinuities in how the catheter responds to flexing or bending across different sections.

FIG. 1B provides an illustration of a section of a catheter body 10 (without abrupt transition regions) in a curved profile to represent the section of the catheter body 10 being pushed to advance through tortuous anatomy. FIG. 1B illustrates a force 7 applied to a proximal end 9 of the catheter body 10, which is resisted by a wall of the vessel, which is represented as force 6. In order to advance the catheter body 10, force 7 must be greater than force 6. When advanced through a tortuous path, the catheter body 10 is placed in a state of tension 32 at an outer portion of the bend and a state of compression 34 at an inner portion of the bend. However, polymers are suited for either compression or tension, and conventional catheter designs do not allow for the selection of a single polymer to maximize performance for both compression and tension. For example, polymers that respond well to tension at the outside of the curve (e.g., generally softer polymers) might not respond well to the compression at the inside of the curve. Likewise, polymers that respond well to compression at the inside of the curve (e.g., relatively stiffer polymers) do not respond well to the tension at the outside of the curve. In addition, polymers must also be selected to respond to torsion and axial compression. Otherwise, problems with poor torque control or instability (e.g., referred to as "whip") and axial instability (commonly referred to as catheter backup) can result. As a compromise, traditional catheter design requires a balancing of polymer properties but fails to produce devices that are optimized for any given procedure—such a compromise results in undesired effects. For example, FIG. 1D provides an image of a React™ 071 catheter 36 supplied by Medtronic. The catheter 36 was held only at ends 37, allowing the catheter to assume its naturally shaped profile. As shown, instead of having a smooth bend radius or curve, the abrupt transition of the catheter 36 causes the bend radius to be irregular at point 38, which results in buckling of the catheter when pushed. The buckling of the catheter 36 reduces the transmission of the push force to the region beyond the buckling as well as decreases navigability.

The undesirability of abrupt transition regions is just one of the drawbacks of traditional catheter design, which requires a balancing act of compromising performance characteristics over any given section of a catheter by selecting a less than desirable material. Accordingly, there remains a need to improve catheter design and catheter structures to produce a catheter with highly customized properties.

SUMMARY OF THE INVENTION

The catheters of the present invention allow for catheter construction custom designed without the need to compromise performance features. Such catheter constructions are possible by being able to customize the properties and materials of any given section of the catheter. Such customized properties include but are not limited to durometer, torque control, flexibility, axial strength, stiffness, etc. The present disclosure also includes variations of improved catheters that have gradual or customized transition sections that can be configured selectively. For example, any section of a polymeric tubing (and therefore a finished catheter construction) can include polymers having a low durometer, a moderate durometer, as well high durometer in the same region. The ability to improve transitions is just one example of the benefit of an improved catheter constructed in accordance with the teachings herein.

For purposes of explaining the features of the present invention, the polymeric strands/components represent the material sections described herein prior to being formed into a tubular wall. As noted herein, in some variations, a material section can be formed from a first polymeric material and extend in a spiral pattern. At some point, the first polymeric material terminates at an end and is joined to an end of a second polymeric material, which still extends or continues in the spiral pattern of the material section. In such a case, the material section is considered to have two different polymeric materials at different lengthwise regions. In additional variations, a material section comprises a polymeric material and extends spirally for a lengthwise region of the tubing, then terminates such that adjacent material sections join together to maintain continuity of the wall of the resulting tubing. It is also noted that, when referring to the joined construction of individual strands, the term tubular wall, polymer tubing, polymer layer, composite tubing, composite layer, etc. can include material sections comprised of one or more materials: metal, stainless steel, alloy, liquid crystal polymer (LCP), fibers, composite material or other similar structures.

It is noted that a transition section shall be used to describe the changing of one or more material strands with a different material. The term transition region shall describe the overall effect of the one or more transition sections. In some variations, the transition region does not include any transition sections because a material simply terminates. Therefore, catheter constructions of the present disclosure can have a transition region that gradually changes material properties over an axial length, or, alternatively, the transition region can be a region of an abrupt change in material properties.

The present disclosure includes a number of variations of catheters having outer tubing layers formed from a plurality of materials to customize characteristics of the lengthwise regions of the catheters. Specific variations of catheters can also include this composite polymeric layer as being on an interior layer of the catheter construction, but in many variations, the custom composite layer is on the outer layer.

Variations of such catheter tubing can include a tubular outer layer extending along an axial length of the tubular body; the tubular body comprising a plurality of material sections extending spirally along the axial length to form a wall of the tubular body, where each material section is joined to an adjacent material section to form the wall; wherein the plurality of material sections include at least a first material section and a second material section, the first material section comprises a first structural property and the second material section comprises a second structural property, where the first structural property differs from the second structural property; and wherein along a transition region of the tubular body a width of the first material section increases while a width of the second material section decreases causing a structural property of the transition region to vary along the transition region.

Another variation of the catheter can include an outer tubular body having a first section and a second section each extending along an axial length of the tubular body; wherein the outer tubular body comprises a plurality of material sections extending spirally along the axial length, where each material section is sealingly joined to an adjacent material section to form a composite wall of the outer tubular body which surrounds a lumen that extends along the axial length; wherein in the first section the plurality of material sections include at least a first material section and a second material section forming the composite wall, the first material section comprises a first structural property and the second material section comprises a second structural property, where the first structural property differs from the second structural property; and a third material section having a third structural property, where the third material section is joined to an end of the first material section at the second section such the third material section replaces the first material section in the second section.

An additional variation of the catheter includes a catheter tubing comprising: a tubular body having a first section and a second section each extending along an axial length of the tubular body; and a plurality of material sections extending spirally along the axial length to form the first section, where each material section is sealingly joined to an adjacent material section to form a composite wall of the tubular body that surrounds a lumen that extends along the axial length; wherein each of the plurality of material sections comprises a structural property respectively and where the structural property of at least two material sections is different; wherein the first section comprises a first sequence of material sections, and wherein the second section comprises a second sequence of material sections such that the material sections in the first sequence is different than the material sections in the second sequence causing a structural property of the first section to be different than a structural property of the second section.

Another catheter construction includes a catheter construction comprising: a catheter shaft having an axial length, the catheter shaft comprising a tubular outer layer comprising a plurality of material sections each having a respective width measured along the axial length, the plurality of material sections extending in a spiral direction along the axial length to form a wall of the tubular outer layer, the tubular outer layer having a first lengthwise region, a second lengthwise region, and a transition region therebetween; wherein at the first lengthwise region the plurality of material sections includes a first material section and a second material section, where a structural property of the first material section is different than a structural property of the second material section to cause the first lengthwise region to have a first structural characteristic; wherein at the transition region, the second material section terminates at an end and a third material section is joined to the end of the second material section, where the structural property of the second material section is different than a structural property of the third material section; and wherein the first material section and the third material section spirally extend from the transition region to the second lengthwise region causing a structural characteristic of the second lengthwise region to be different than the structural characteristic of the first lengthwise region.

Yet another variation of a catheter construction includes a catheter shaft having a tubular outer layer extending over at least a portion of an axial length of the catheter construction, the tubular outer layer comprising a plurality of material sections each having a respective width measured along the axial length, the plurality of material sections extending in a spiral direction along the axial length to form a wall of the tubular outer layer, the tubular outer layer having a first lengthwise region, a second lengthwise region; and wherein at the first lengthwise region the plurality of material sections includes a first material section at a first lengthwise region having a first structural characteristic; wherein at the second lengthwise region at least a portion of the first material section terminates at an end and a second material section is joined to the end of the first material section, where the structural property of the first material section is different than a structural property of the second material section to cause the second lengthwise region to have a second structural characteristic different than the first structural characteristic.

Another variation of a catheter construction includes a tubular outer layer comprising a plurality of material sections, each having a respective width measured along the axial length, the plurality of material sections extending in a spiral direction along the axial length to form a continuous wall of the tubular outer layer; wherein the plurality of material sections includes a first material section and a second material section adjacent to the first material section, where a structural property of the first material section is different than a structural property of the second material section.

Another variation includes a catheter shaft having an axial length, the catheter shaft comprising an inner liner, a reinforcement structure exterior to the inner liner, and a tubular outer layer extending over the reinforcement structure; the tubular outer layer comprising a plurality of material sections each having a respective width measured along the axial length, the plurality of material sections extending in a spiral direction along the axial length to form a continuous wall of the tubular outer layer; wherein the plurality of material sections includes a first material section, a second material section, and a third material section, where a structural property of each of the first material section, second material section, and third material section are different; and the tubular outer layer having a first transition region where a width of at least one of the first material section, second material section, or third material section changes over the first transition region causing a change in a structural property of the first transition section.

Yet additional variations include medical tubing comprising: a tubular layer comprising a plurality of material sections, each having a respective width measured along the axial length, the plurality of material sections extending in a spiral direction along the axial length to form a continuous wall of the tubular outer layer; wherein the plurality of material sections includes a first material section and a second material section adjacent to the first material section, where a structural property of the first material section is different than a structural property of the second material section; and a first lengthwise region of the tubular outer layer where a width of the first material and a width of the second material both change along the first lengthwise region causing a structural property to change over the first lengthwise region.

A medical tube can also include a tubular outer layer comprising a plurality of material sections each having a respective width measured along the axial length, the plurality of material sections extending in a spiral direction along the axial length to form a continuous wall of the tubular outer layer; wherein the plurality of material sections includes a first material section, a second material section, and a third material section, where a structural property of each of the first material section, second material section, and third material section are different; and the tubular outer layer having a first lengthwise region where a width of at least one of the first material section, second material section, or third material section changes over the first lengthwise region causing a change in a structural property of the first lengthwise section.

Another variation of a medical tube comprises: a catheter shaft having an axial length, the catheter shaft comprising an inner liner, a reinforcement structure exterior to the inner liner, and a tubular outer layer extending over the reinforcement structure; the tubular outer layer comprising a plurality of material sections each having a respective width measured along the axial length, the plurality of material sections extending in a spiral direction along the axial length to form a wall of the tubular outer layer, the tubular outer layer having a first lengthwise region, a second lengthwise region, and a transition region therebetween; wherein at the first lengthwise region the plurality of material sections includes a first material section and a second material section, where a structural property of the first material section is different than a structural property of the second material section to cause the first lengthwise region to have a first structural characteristic; wherein at the transition region, the second material section terminates at an end and a third material section is joined to the end of the second material section, where the structural property of the second material section is different than a structural property of the third material section; and wherein the first material section and the third material section spirally extend from the transition region to the second lengthwise region causing a structural characteristic of the second lengthwise region to be different than the structural characteristic of the first lengthwise region.

The present disclosure also includes one or more methods of forming a polymer tube. For example, such a method can include wrapping a plurality of polymer strands in a spiral configuration forming a polymer tube, where at least two of the polymer strands comprise different structural properties; wherein in a first section of the polymer tube, the plurality of polymer strands forms a first sequence; altering the sequence of the polymer strands to form a second sequence in a second section of the polymer tube; and fusing each polymer strand to an adjacent polymer strand to form a continuous wall in the polymer tube, where the continuous wall defines a lumen therethrough and wherein a structural property of the first section differs from a structural property of the second section due to the difference in the first sequence and the second sequence.

Another catheter under the present disclosure includes an inner liner; an outer layer comprising a plurality of polymer strands wrapped in a spiral configuration, where at least two of the polymer strands comprise different structural properties; wherein in a first section of the outer layer, the plurality of polymer strands forms a first sequence; where in a second section of the polymer tube the polymer strands form a second sequence; and where each polymer strand is fused or joined to an adjacent polymer strand such that the plurality of polymer strands form a continuous wall defining a lumen through the polymer tube and wherein a structural property of the first section differs from a structural property of the second section due to the difference in the first sequence and the second sequence.

Another variation of a catheter includes an inner liner; an outer layer comprising a first polymeric material having a tube shape, at least a second polymer strand wrapped in a spiral configuration about the tube shape and fused into the first polymeric material that at least a portion of the wall of the tube shape comprises the first polymeric material and the second polymeric material, where the first polymeric material and the second polymeric material comprise different structural properties; wherein in a first section of the outer layer the first polymeric material and the second polymeric material forms a first pattern; wherein in a first section of the outer layer the first polymeric material and the second polymeric material forms a first pattern; and where each polymer strand is fused or joined to an adjacent polymer strand such that the plurality of polymer strands form a continuous wall defining a lumen through the polymer tube and wherein a structural property of the first section differs from a structural property of the second section due to the difference in the first sequence and the second sequence.

The catheter and tubing configurations of the present disclosure allow for a considerable number of combinations and permutations of different variations of catheters as well as combination of aspects of those structures as well. It is contemplated that any of the following requirements and elements can be combined with any independent claim where the requirements of the independent claims would not contradict the various elements.

Any of the constructions herein can include the tubular outer layer comprising a plurality of material sections each having a respective width measured along the axial length, the plurality of material sections extending in a spiral direction along the axial length to form a continuous wall of the tubular outer layer.

Any variation of the devices/methods can further comprise an inner liner within the tubular outer layer and a reinforcement structure exterior to the inner liner and within the tubular outer layer.

Variations can include the width of the first material section and the width of the second material section change along the first transition region.

Variations can include the tubular outer layer having a proximal lengthwise region proximal to the first transition region, where the proximal lengthwise region is entirely formed from the first material section.

Variations can include a third material section extending over a majority of the axial length of the catheter tubular body.

Variations can include a width of the first material section being greater than the width of the second material in at least a first section of the wall of the tubular body.

Variations can include tapering of an end of the second material section.

The catheters and structures described herein can have material sections that have a right-hand wind, a left-hand wind, or both.

Variations of any devices or methods herein can include at least one of the material sections that comprise a non-fusable material. Moreover, such a non-fusable material can be used for manufacture only, whereupon removal of that non-fusable material imparts a groove cavity or other design feature on any surface of the device.

The devices herein can also include an inner liner within the tubular outer layer and a reinforcement structure exterior to the inner liner and within the tubular outer layer.

Variations of the device construction herein can further include a tubular outer layer further having a second lengthwise region, a third lengthwise region, and a transition region therebetween; wherein the second lengthwise region includes the first material section and the second material section that define a structural characteristic of the second lengthwise region; wherein at the transition region, the second material section has an end and a third material section is joined to the end of the second material section, where the structural property of the second material section is different than a structural property of the third material section; and wherein the first material section and the third material section spirally extend from the transition region to the third lengthwise region causing a structural characteristic of the third lengthwise region to be different than the structural characteristic of the second lengthwise region.

The catheter or catheter construction of any of the proceeding examples can include a tubular outer layer that comprises a plurality of material sections, each having a respective width measured along the axial length, the plurality of material sections extending in a spiral direction along the axial length to form a continuous wall of the tubular outer layer. Moreover, the changes in any material section can be incremental or continuously vary.

This application is related to U.S. patent application Ser. No. 17/173,003, filed Feb. 10, 2021, which is a divisional of U.S. patent application Ser. No. 16/902,154, filed Jun. 15, 2020, which is a non-provisional of U.S. provisional application No. 62/862,035, filed on Jun. 15, 2019. This application is also related to PCT application no. PCT/US2020/037808 filed on Jun. 15, 2020, the entirety of each of which is incorporated by reference.

BRIEF DESCRIPTION OF THE FIGURES

FIG. 2D illustrates a concept of a catheter shaft intended to illustrate features of the catheter design according to this disclosure.

FIG. 2E illustrates various paths through which variations of catheter section of the present invention are specifically designed to navigate through.

FIGS. 14A to 14C illustrate another variation a composite polymer tube having a plurality of material sections where the material section is embedded within a polymer tube.

FIG. 23A to 23F illustrates another variation of fabrication of a composite tube.

DETAILED DESCRIPTION

The catheter configuration discussed herein can be used in a variety of devices where different regions are selected for customized properties. The configurations described herein can be incorporated into various medical devices or can be used as catheter shafts. Furthermore, in some variations, the construction features of the present disclosure are not limited to in-dwelling medical devices and can be used for any device requiring tubing.

The polymeric tubing described herein can be constructed in any manner that allows the material section configurations (and hybrid-regions) disclosed below. Such manufacturing means includes, but is not limited to: forming the polymeric tube by winding directly onto catheter shaft; forming the strands into composite sheets and then winding the sheet onto a structure to complete a catheter shaft; and/or first winding ribbons/strands onto a mandrel or support structure, then fusing the material into a tube, then transferring onto a catheter assembly.

Figure 2A:
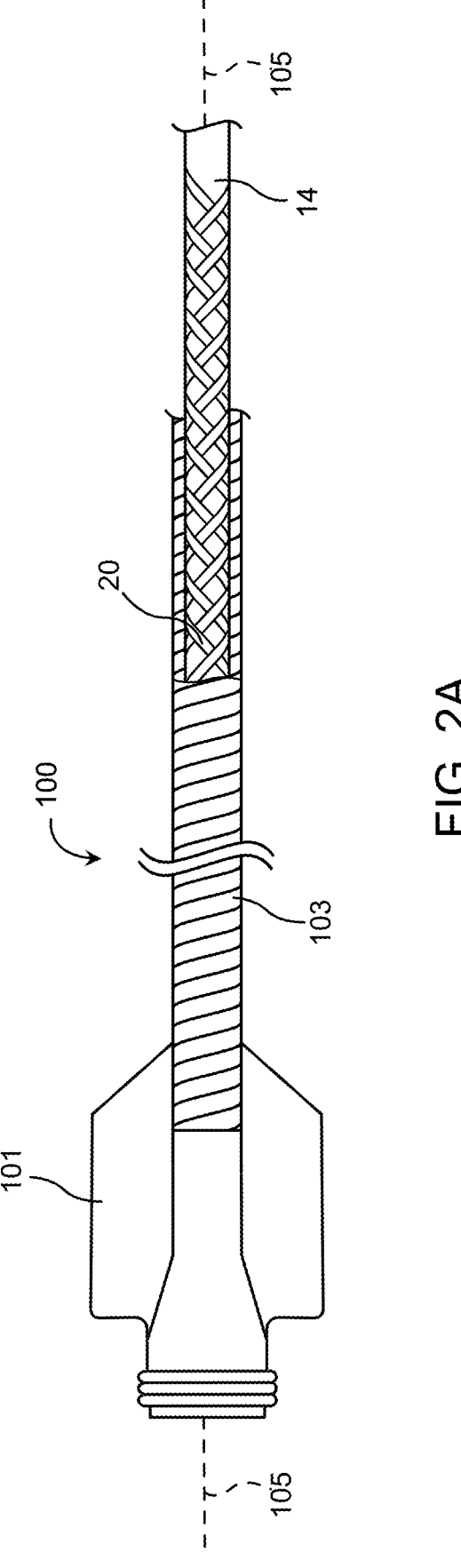
FIGS. 2A to 2C show partial sectional views of improved catheters incorporating improved polymeric outer layers as described herein.
Figures 2B, 2C:
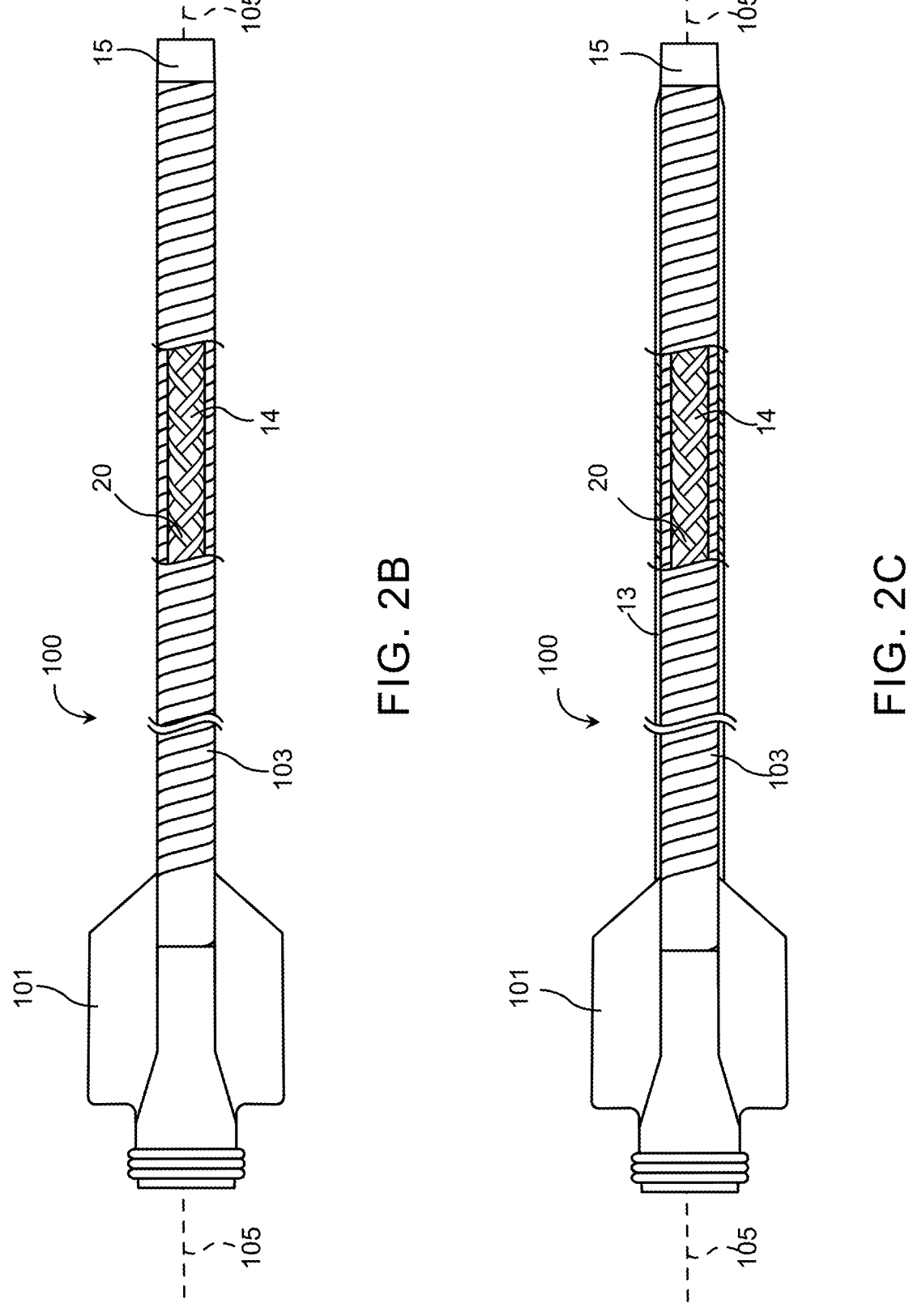

FIGS. 2A to 2C show a partial sectional view of an improved catheter 100 incorporating an improved composite outer layer 103 as discussed herein. The catheter construction discussed herein can incorporate any number of features known by those skilled in the art of catheter construction. Such features are omitted herein so that the focus of the improved catheter composite outer layer 103 can be explained. Furthermore, the improved catheter construction disclosed herein can be incorporated into any number of catheters that can benefit from customization of features provided by the improved polymeric outer layer 103. For example, such catheters include, but are not limited to, distal access catheters, sheaths, guide catheters, balloon catheters, intracranial support catheters, micro catheters, arterial line catheters, central venous catheters, pulmonary artery catheters, coronary and cardiac catheters, and peripheral catheters, etc.

Additional variations of the improved construction can be used in any polymeric tubular structure. It should be noted that any catheter construction or polymer tubing disclosed herein is not limited to a single uniform outer diameter across the entire catheter. As disclosed below, the catheters and polymer tubing of the present disclosure can have an undulating outer diameter. Alternatively, or in combination, the outer diameter can vary throughout various lengthwise regions of the catheter. The term lengthwise region is intended to mean a region of any length along an axis 105 of the tube construction. The catheter constructions and tubular constructions disclosed herein can have any number of conventional cross-sectional shapes. For example, variations of the devices can include catheters that have different diameters and/or cross-sectional shapes at different regions. Some sections of catheters and tubular constructions can include round cross-sectional shapes that change to non-round shapes.

As shown in FIG. 2A, in one variation of the device, the tubular construction or shaft of the catheter 100 extends from a hub 101 and can be formed by the improved outer composite layer 103, discussed below, that overlays a braid 20, coil, or other support structure commonly used with catheters. The braid 20 is positioned about a tubular inner liner 14 (commonly constructed from PTFE, but other materials are within the scope of this disclosure). As shown in FIG. 2A, the improved composite layer 103, is the outermost component of the catheter tubing. As noted below, the improved composite layer 103 can include any number of lengthwise regions that are better suited to transmit torque through the catheter 100. Positioning these polymeric torque transfer regions on the exterior of the catheter improves the effectiveness of the torque transfer region as compared to conventional catheters that mainly rely on the braid 20 that is positioned within the catheter shaft.

FIG. 2B illustrates a variation similar to that shown in FIG. 2A, where the catheter 100 includes a distal tip 15 coupled to the end of the tubing 103. In some variations, the distal tip 15 can comprise a soft polymeric or other material. FIG. 2C illustrates a device 100 similar to those shown in FIGS. 2A and 2B with the addition of an outer layer 13 positioned over the tubular member 103. The outer layer 13 can comprise a transparent or translucent material. In most cases, the performance and characteristics of the device 100 will be controlled by the selection of materials forming the tubular member 103, the incorporation of the braid/coil or other support structure 20. In additional variations, the outer layer 13 will not affect the performance and/or characteristics of the device 100.

Figures 2D, 2E:
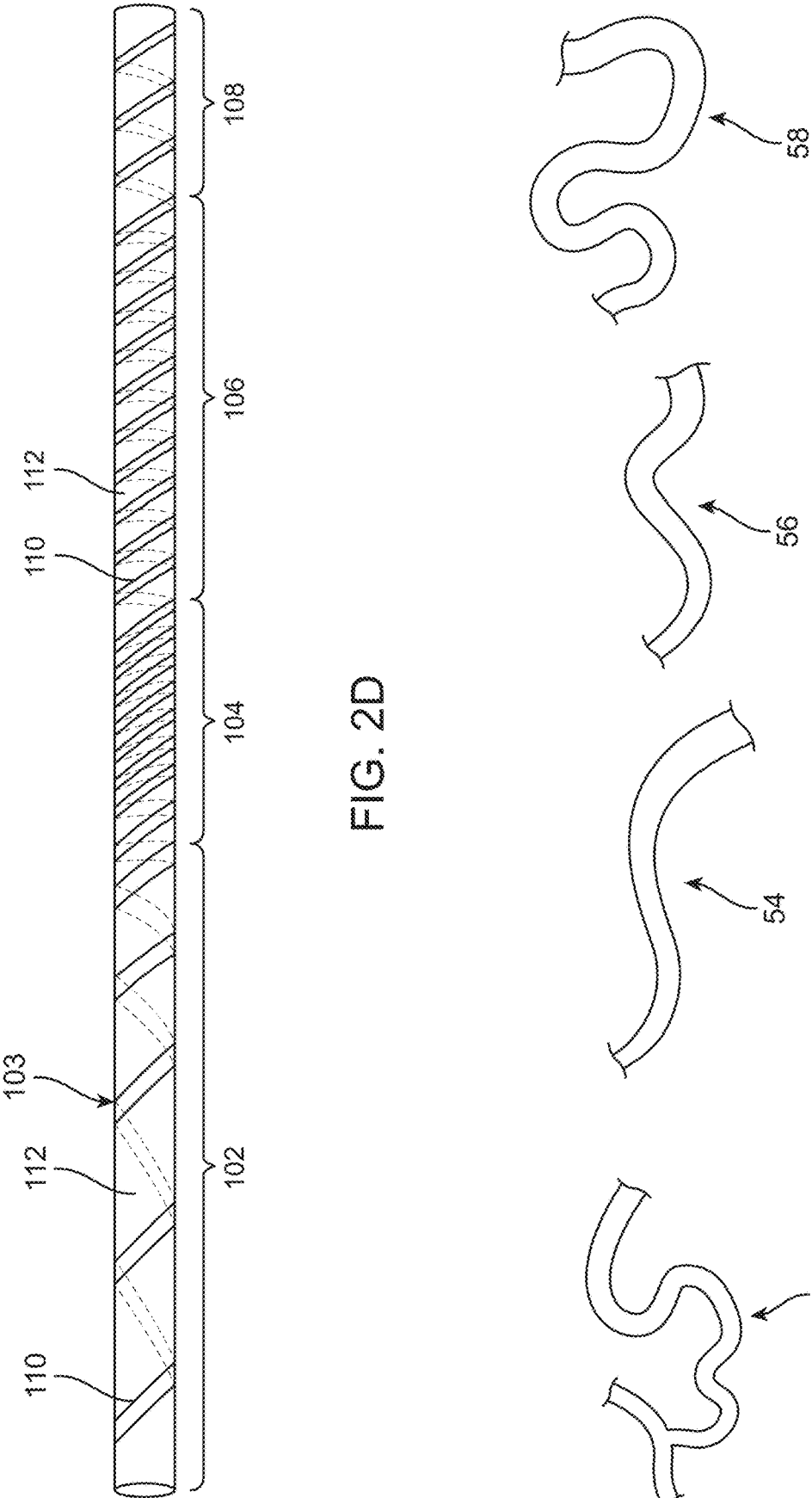

FIG. 2D illustrates a concept of a catheter layer 103 intended to illustrate features of the catheter design according to this disclosure. The layer 103 can be incorporated into the catheter construction as shown in FIG. 2A or in any variation of such a construction (e.g., a catheter without a reinforcing structure 20 and/or a catheter without a liner 14). As shown, the catheter layer 103 can include any number of regions 102, 104, 106, and 108, where the structural properties of each region can be customized based upon an intended purpose for the catheter or as otherwise needed. For example, the layer 103 illustrated in FIG. 2D can be optimized or matched for use in a catheter that is intended to be advanced through vasculature that has a varying tortuosity. In the illustrated example, referring to FIG. 2E, region 102 can be designed to navigate tortuous region 52, while regions 104, 106, and 108 can be designed for respective regions 54, 56, and 58. FIG. 2D shows the catheter layer 103 as having at least one material section extending in a spiral or helical pattern with a pitch that varies along the length of the finished layer 103. In one variation, the various lengthwise regions 102, 104, 106, 108 can be matched to particular regions of the vasculature 52, 54, 56, 58 each having a different levels of tortuosity. As described herein, the layer 103 can comprise any number of material sections. Moreover, the actual material of any material section (e.g., 110, 112) can change over the length of the layer 103, which can result in a new region.

FIG. 2D also illustrates that material section 110 comprises a helical region of a polymer extending adjacent to a second material section 112 that comprises a second polymer (or alternate catheter material) to create regions (102, 104, 106, 108). having desired properties that extend along the catheter 100. For example, a pitch of the first material section 110 can vary in each region 102, 104, 106, and 108. Alternatively, or in combination, a width of any of the material sections can vary by region. For instance, the material section 110 can comprise a reinforcing polymer (e.g., PEBAX 72D or similar material).

In another variation, the material section 110 can comprise a first polymer material (e.g., PEBAX 35D) within a second material section 112 comprising a relatively stiffer material (e.g., PEBAX 40D-70D) where the helical pitch of the material sections are selected such that a first region 102 is relatively firmer than the remaining regions, and where a firmness of an adjacent region 104 decreases relative to region 102. This varying of firmness can continue until region 108 is the softest/least stiff region and serves as a distal portion of the material layer 103, which in turn similarly affects the distal portion of a catheter incorporating the material layer 103.

Figure 2F:
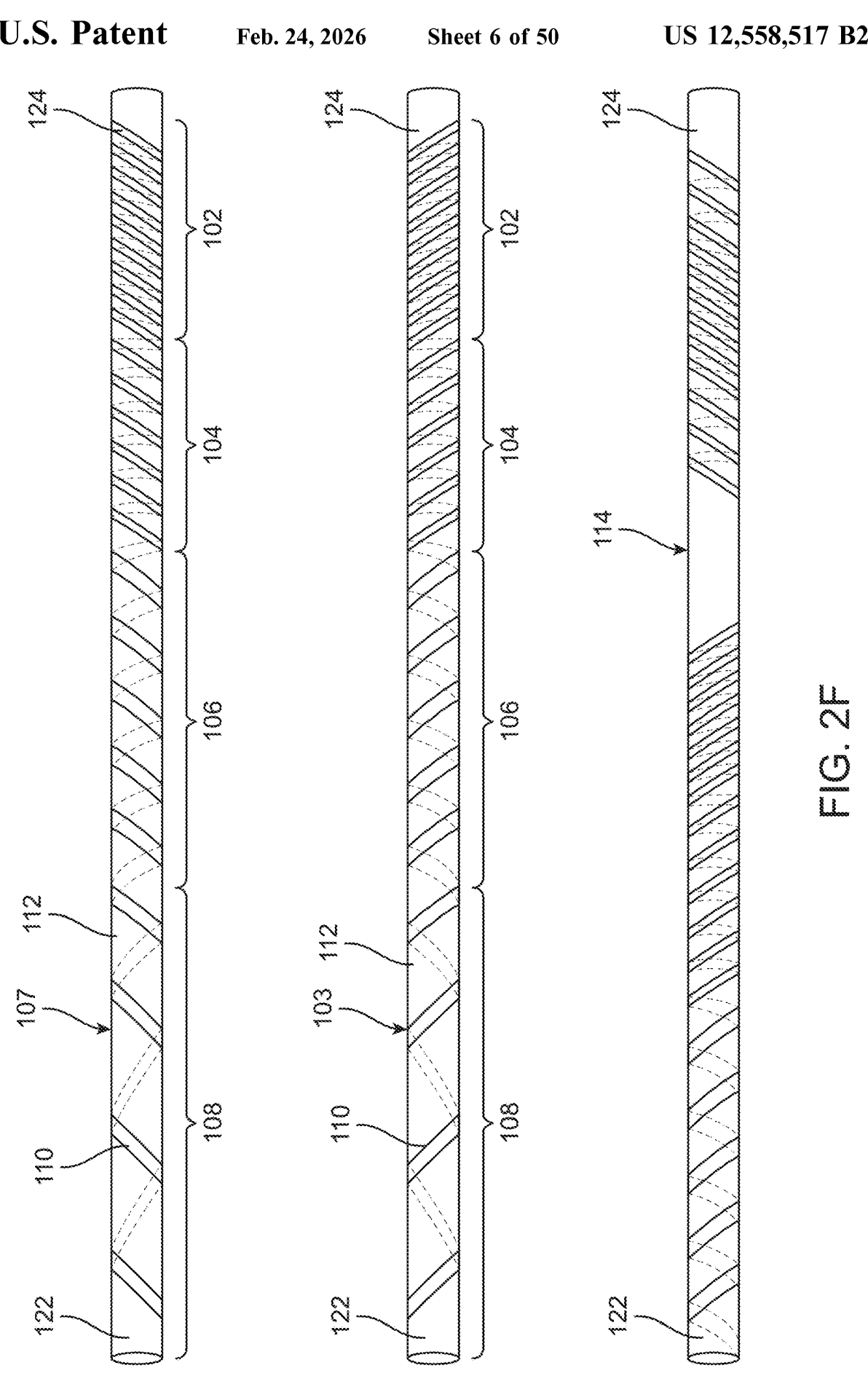
FIG. 2F illustrates three catheters that have material sections that are wound in left-hand and right-hand directions.

The construction of the layers 103 of the present disclosure allows for any number of engineered catheters with custom properties. FIG. 2F illustrates two layers 103 and 107 to illustrate that the novel layers of the present disclosure provide an ability to produce catheter constructions having winding directions of either left-hand (layer 103) or right-hand (layer 107) winding of the material sections 110, 112 to produce directionally biased catheters having opposite winding features between distal 122 and proximal 124 regions. In the first variation shown in FIG. 2F, layer 103 can be used with a catheter that requires varying regions 102, 104, 106, 108. However, in this variation, region 108 comprises a material section 110 having a loose pitch wound in a right-handed direction and comprising a stiff polymer strand to produce a soft region that can be used to form a distal region of a catheter. The adjacent region 106 comprises a more moderate pitch of the material section 110 such that it is not as soft as region 108. The pitch of the material section 110 can increase in sections 104 and 102, which allows for increased support. While the figures in 2F only show two material sections, 110 and 112, any number of material sections formed from polymeric material can be used to produce the varying sections of the outer layer 103 that forms the catheter. As noted above, the structural characteristics of the various regions can be matched to the characteristics of the target anatomy. Moreover, the winding of the material sections 110 and/or 112 (or the specific material selection) as shown in either layer 103 or 107 can produce a specific directionally-wound catheter (i.e., a catheter that is pre-disposed to follow a winding of a particular region of the anatomy). Specifically, the directionality of the winds can be matched to the directional twist of the vessels (i.e., left-hand wind catheter for left side internal carotid artery and vessels, and right-hand wind catheter for right internal carotid artery and vessels, etc.). For example, a left carotid artery of an individual winds in a left-handed direction while a right carotid artery of that individual winds in a right-handed direction. The catheter constructions using the disclosed catheter layers (e.g., 103, 107) produce a catheter that is suited to specifically follow the bend of a specific internal carotid artery or any other artery or body passageway. Generally, the direction of the reinforcement strand, as discussed herein, can pre-dispose the catheter to bend or navigate in a particular rotational direction within the anatomy. As noted herein, the present disclosure permits customization of any region of a catheter construction with specific material characteristics. Moreover, catheter layer 114 includes a single tubing having a right-handed winding adjacent to the distal end of the layer 114 and a left-handed winding adjacent to the proximal end of the layer 114. Clearly, the present disclosure includes winding of material sections in a single direction or multiple directions along the length of any tubing.

Figure 1A:
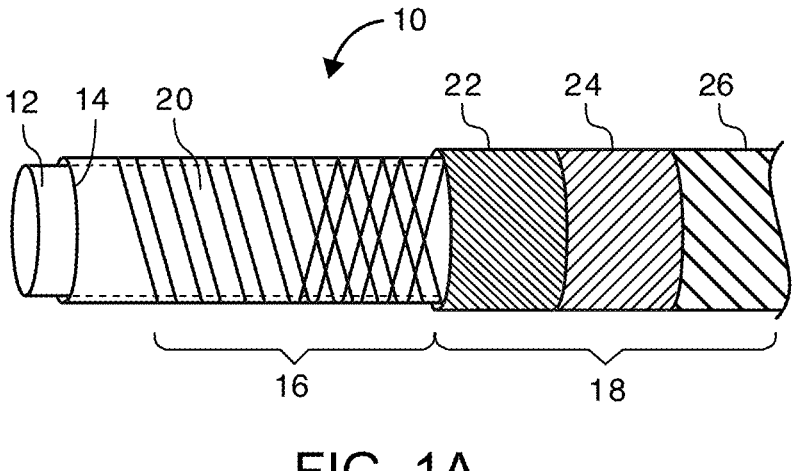
FIG. 1A illustrates a traditional catheter construction and shows sectional views of a catheter section that is constructed on an inner extruded tube.
Figure 1B:
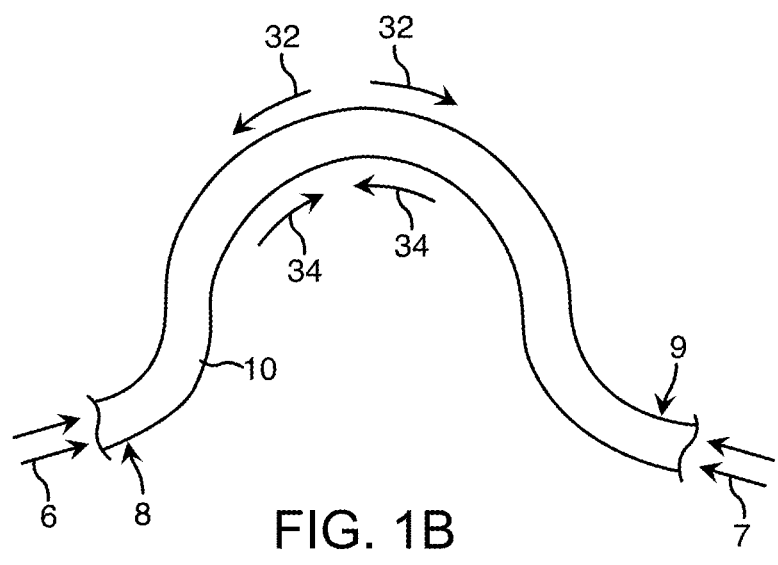
FIG. 1B provides an illustration of a catheter body in a curved profile.
Figure 1C:
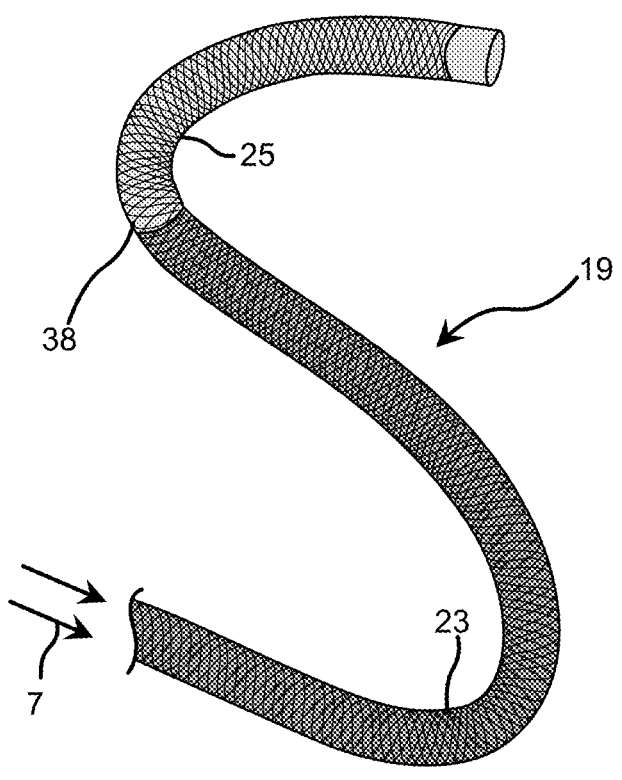
FIG. 1C shows a conventional catheter having multiple durometer regions.
Figure 2G:
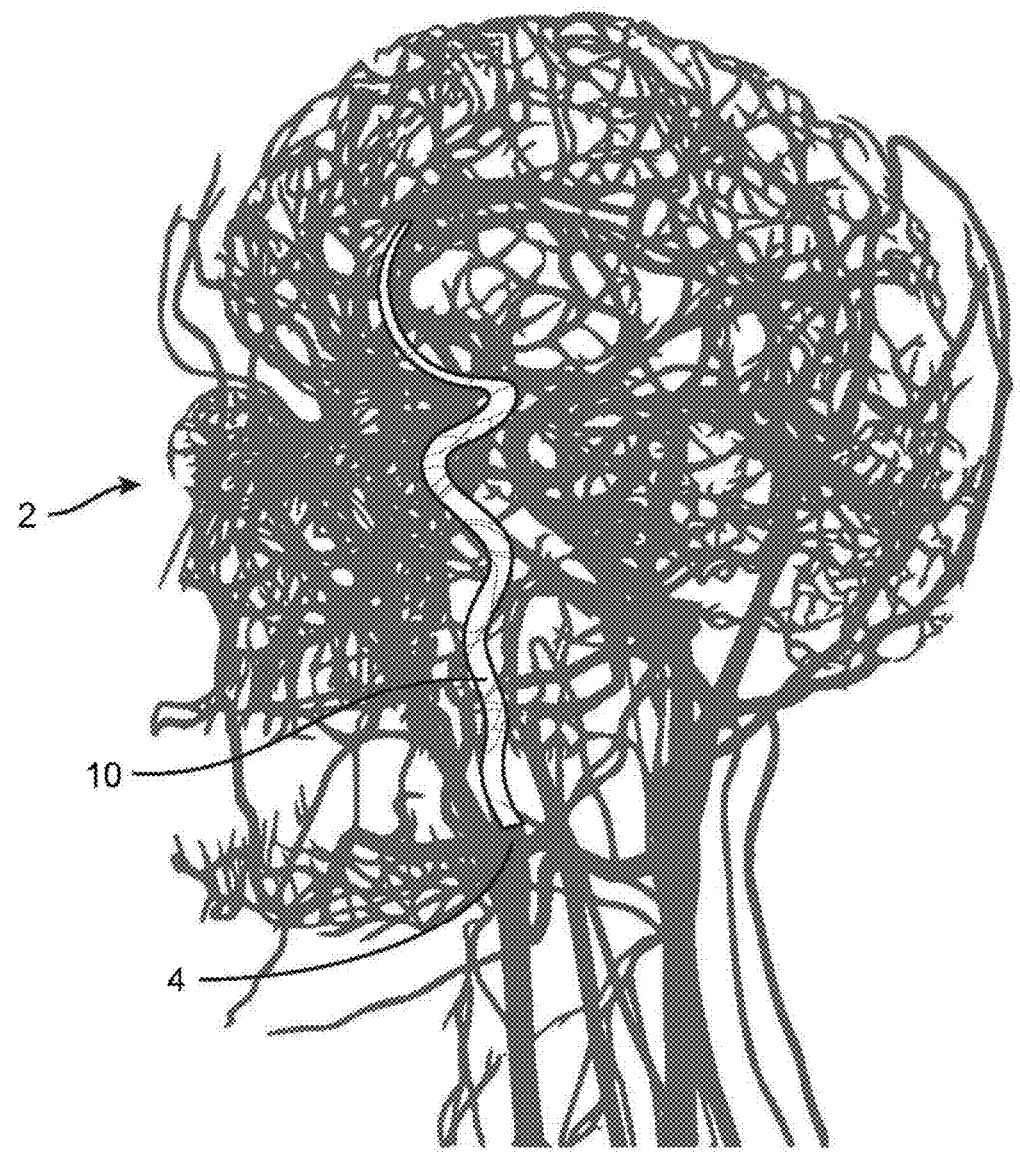
FIG. 2G illustrates various cerebral vessels with a catheter that is advanced through one of the carotid arteries.
Figure 2I:
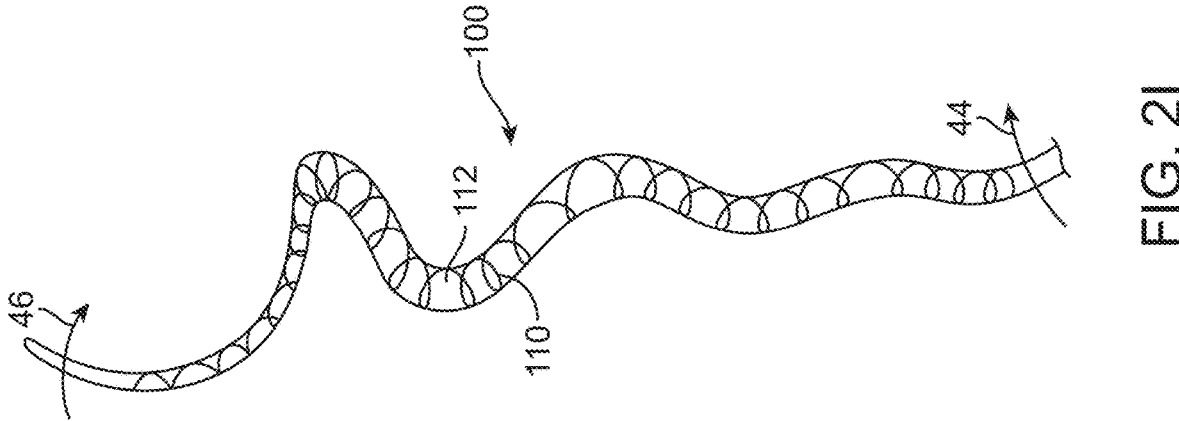
FIGS. 2I and 2J illustrate a shape of an improved catheter when it advances in the vessel of FIG. 2I and takes the shape of that vessel.
Figure 2H:
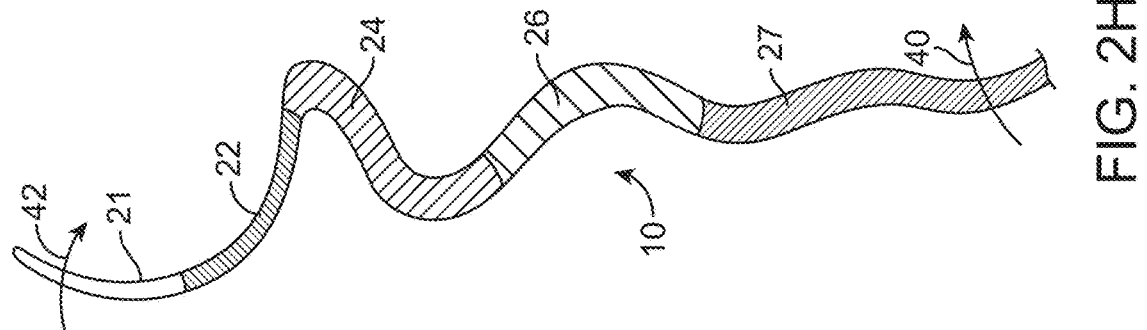
FIG. 2H illustrates a conventional catheter when advanced through a carotid artery, where the conventional catheter includes different sections having abrupt changes between sections.
Figure 2J:
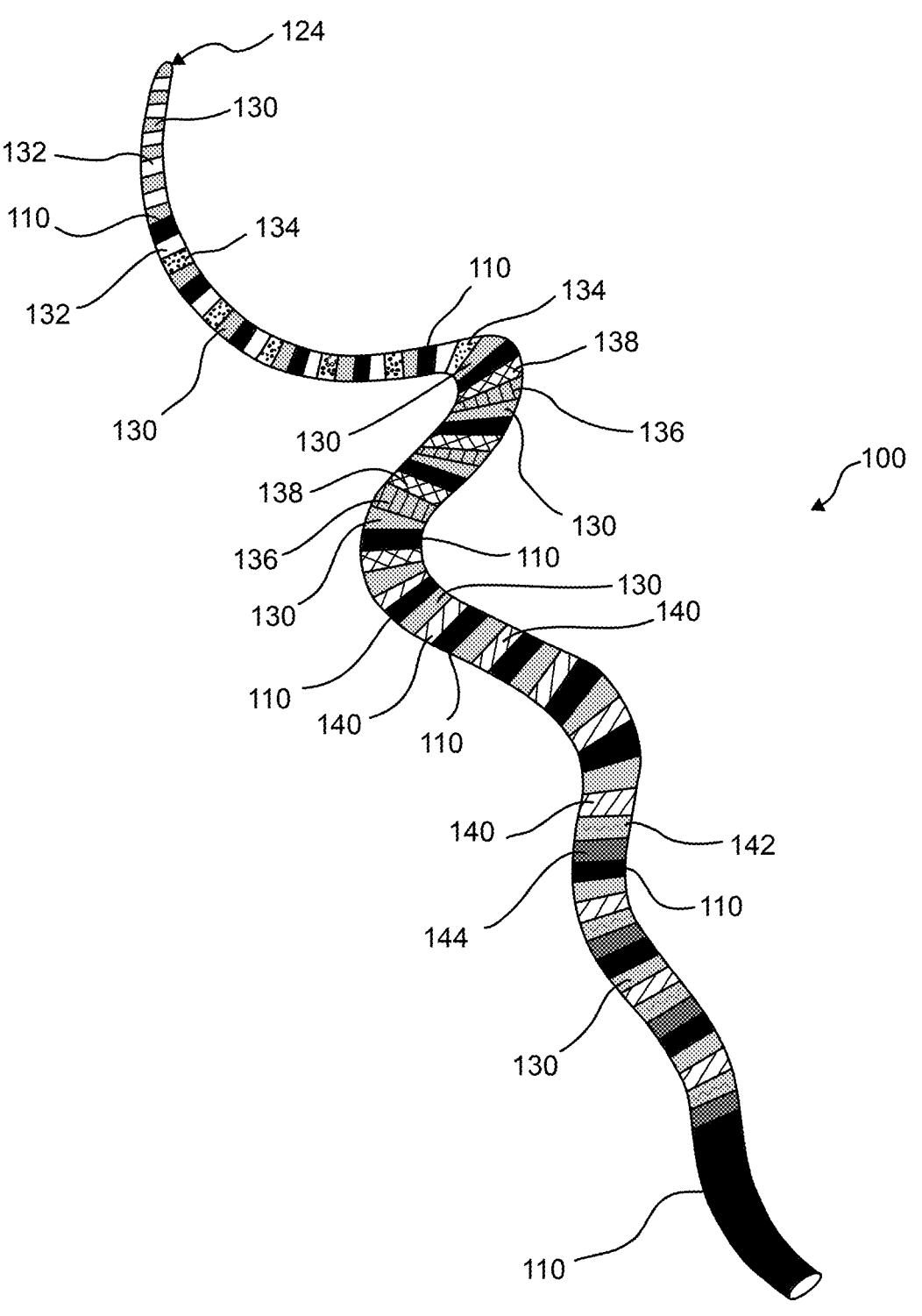

FIGS. 2G, 2I, and 2J further illustrate the benefit of the catheter using the configurations disclosed herein. FIG. 2G illustrates various cerebral vessels with a catheter 10 advanced through one of the carotid arteries 4, which is typically used to, access the brain. The carotid arteries 4 have various regions of tortuosity and decreases in diameter as the vessel advances further into the brain. FIG. 2H illustrates a conventional catheter that is advanced through the vessel 4 of FIG. 2G and takes a shape of that vessel 4. This catheter 10 is similar to the construction shown in FIG. 1A, where the catheter includes varying discrete regions of stiffness 21, 22, 24, 26, 27. As discussed above, although conventional catheters are designed to have different regions, each region has a discrete change in polymer (or other features such as removal of an inner liner, alteration of a braid/coil structure, etc.) and therefore, the, catheter 10 has an abrupt change in structural properties at the intersection of each region 21, 22, 24, 26, 27. One of the issues with such designs is the loss of torque being evenly applied across the various sections. In other words, the torque 40 applied at the proximal, stiffer section 27 will be greater than the torque 42 of the distal-most section 21, which is generally the most flexible section. In addition to a difference in torque, the rotational deflection of the proximal section 27 will be greater than the rotational deflection of the distal-most section 21.

FIGS. 2I and 2J illustrate when an improved catheter 100 advances in the vessel 4 of FIG. 2G and takes the shape of that vessel. FIG. 2I illustrates a variation of a catheter 100 of the present design but only shows a first material section 110 spirally wound with a second material section 112 for purposes of illustration. As noted herein and shown in FIG. 2J, any number of material sections can be used in a catheter 100. For purposes of illustration, the material section 110 comprises a single polymer having a stiff material property (e.g., 72D). This example shows the first material section 110 with the polymer that extends the length of the catheter 100. Therefore, the helically formed polymer strand material section 110 assists in transmitting application of torque 44 through length of the material section 110 along the catheter 100 such that the torque 46 at the distal end is closer to the torque 44 at the proximal end unlike conventional catheters.

FIG. 2J illustrates an additional variation of a catheter 100 having a number of material sections 110, 130, 132, 134, 136, 138, 140, 142 spirally extending along a length of the catheter 100. The material sections shown in FIG. 2J are merely for the purpose of illustration, and any number of polymers can extend spirally about the catheter 100 where some polymers cease or taper at different regions, and different polymers begin such that various regions of the catheter can include different polymers to give each region of the catheter a unique structural property. FIG. 2J is intended to illustrate the ability to position a combination of materials along any section of the catheter 100. For purposes of illustrating one variation of the catheter 100, a material section 110 of the catheter forms a majority of a wall of the material layer (see e.g., 103 in FIG. 2A) at the proximal end 122 of the catheter 100. The polymer forming the material layer 110 at the proximal end 122 of the catheter 100 extends spirally along a length of the catheter 110, and the material either changes or the material section is terminated prior adjacent to a distal end 124 of the catheter 100 such that the material sections at the distal end 124 comprise different material sections 130, 132 or different polymers. As noted herein, a material section can be terminated, or a polymer in a material section can be joined to an end of a different polymer in a material section such that the polymer changes in the same material section.

Figure 2K:
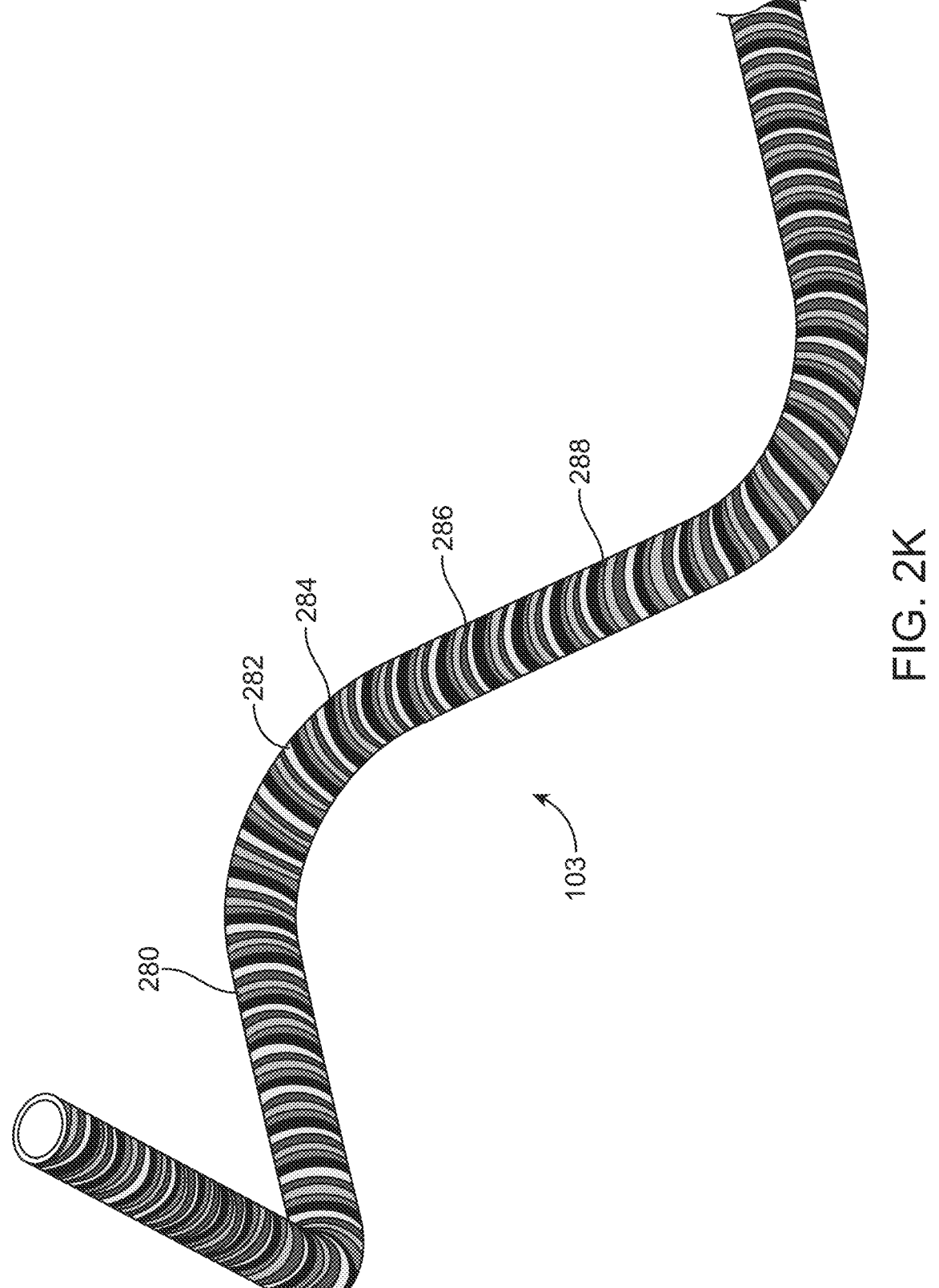
FIG. 2K illustrates one possible design configuration to produce a catheter construction using a composite tubing with material sections comprising different materials that each provide different mechanical advantages/benefits all within a single region of the finished catheter.

FIG. 2K illustrates one possible design configuration to produce a catheter construction using a composite tubing 103 with material sections comprising different materials that each provide different mechanical advantages/benefits, all within a single region of the finished catheter. The result is that the finished catheter section will achieve a mix of mechanical features within one region of the catheter. Such a configuration is simply not possible with conventional catheter designs. For example, FIG. 2K shows a composite layer or tube 103 having multiple material sections 280, 282, 284, 286, and 288. These material sections can each provide unique benefits: material section 280 comprises a low durometer ultra-soft material for high flexibility; material section 282 comprises a moderate durometer material that provides some flexibility as well as axial stability; material section 284 comprises a high durometer material that provides enhanced torque control as well as rotational and axial stability. Material sections 286 and 288 are shown to represent that the composite tube 103 can include any number of additional material layers.

The various polymer strands used to fabricate the catheter (or outer layer) can be selected to impart desired characteristics for the catheter 100 based upon a desired use of the catheter and/or depending on the intended path of the target within the body. This construction allows various characteristics of any polymer to be extended across sections of the catheter 100 or an entirety of the catheter 100 such that the catheter does not contain any regions of abrupt changes in structural characteristics/properties that affect bending, torqueing, flexing, etc. rotational stability and axial stability.

Figure 3A:
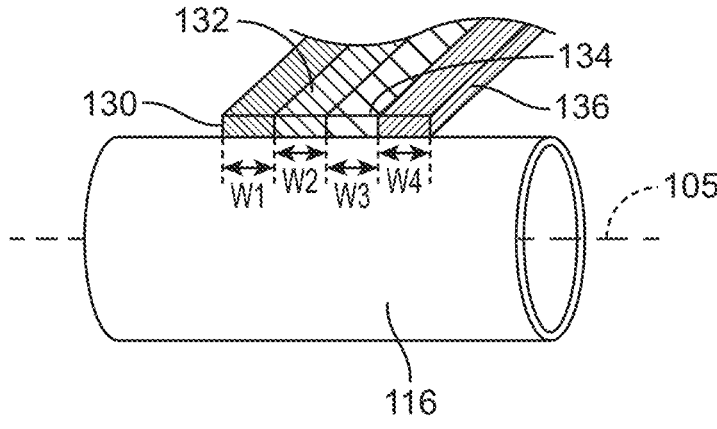
FIGS. 3A and 3B illustrate one example of the fabrication process to construct a catheter section under the present disclosure.
Figure 3B:
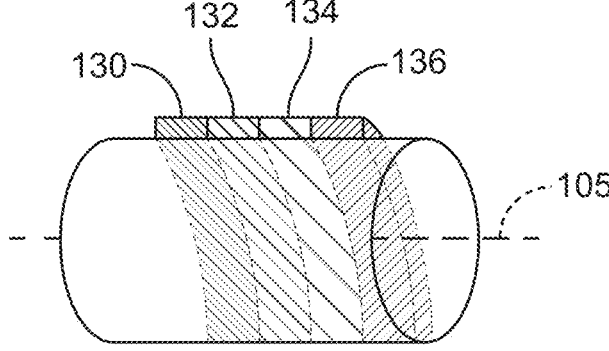

FIGS. 3A and 3B illustrate an example of the fabrication process to construct a catheter section under the present disclosure. It is contemplated that any manufacturing process that creates a catheter or catheter layer with a plurality of material sections is within the scope of this disclosure. For example, such manufacturing processes can include wrapping polymer strands (as shown), 3D printing, extrusion, etc.). As shown in FIG. 3A a number of polymer strands or ribbons are placed in a pattern to coincide with material sections 130, 132, 134, 136 and can be wrapped about a structure 116. The structure can comprise a mandrel, tube, or a braid/liner of a catheter structure. Once the polymeric strands are wrapped, they are fused or otherwise joined together to form a layer as described here (e.g., see layer 103 of FIG. 2A). In one variation, the wrapped and joined polymer ribbons form a wall layer of a catheter after they are fused together. Alternatively, the polymer ribbons can form an outer layer over a tube, braid and/or coil 116 and form a portion of a catheter section. For the sake of convenience, the polymer strands/ribbons/extrusions shall be referred to as polymer strands. The present invention includes the polymer sections as having any shape necessary to complete the catheter section. As shown, a cross-section of the polymer strands can be rectangular. Alternatively, the polymer strands can be oval, round, or have any other shape. In additional variations, polymer strands of different shapes and sizes can be combined to form a layer. Moreover, the polymer strands can comprise single lumen extrusions/tubes that are collapsed and melted/fused down. Alternatively, the strands can be extruded or otherwise manufactured to be solid. In another variation, the lumen of each polymeric strand is left intact. In a typical variation, the strands are wound over a braid or coil (as discussed above). In an additional variation, the polymer strand construction discussed herein can be used to form an inner layer of a catheter (instead of or in addition to a polymeric liner), with a separate construction being used for an external layer of the catheter. In an additional variation, even though the disclosure herein discusses strands and material sections as comprising polymers. A strand or material section can comprise a non-polymeric material (e.g., metal, stainless steel, alloy, liquid crystal polymer (LCP), fibers, composite material, or other similar structures). Strands can be different materials, shapes, sizes, and mixed together, or can be placed and removed to leave voids. Strands can also be different materials, shapes, sizes, and mixed together, or can be placed and removed to leave voids.

For purposes of explaining the features of the present invention, the polymeric strands/components represent the material sections described herein prior to being formed into a tubular wall. As noted herein, in some variations, a material section can be formed from a first polymeric material and extend in a spiral pattern. At some point, the first polymeric material terminates at an end and is joined to an end of a second polymeric material, which still extends or continues in the spiral pattern of the material section. In such a case, the material section is considered to have two different polymeric materials at different lengthwise regions. In additional variations, a material section comprises a polymeric material and extends spirally for a lengthwise region of the tubing, then terminates such that adjacent material sections join together to maintain continuity of the wall of the resulting tubing.

Regardless of the fabrication process, the polymer strands in each of the material sections 130-136 can comprise polymers of varying compositions. In one example, the polymers can be a common material (e.g., PEBAX) where each strand in a respective material section 130-136 comprises a different durometer. For example, the strands can have the following associated durometers: 130—72D, 132—63D, 134—35D, and 136—45D. Clearly, any number of variations are within the scope of this disclosure.

FIG. 3A also illustrates the plurality of material sections 130, 132, 134, 136, each having a respective width W1, W2, W3, and W4, measured along an axial length 105 of the tube. In this illustration, the axial length 105 is the axial length of the core or tube, which will generally be similar if not the same as an axial length of the finished tube or a catheter having a layer formed by material sections 130, 132, 134, 136. In the case of materials not yet formed into a tube structure, the width is measured in a plane that is perpendicular to a length of the strand. As shown in FIG. 3B the material sections extend in a spiral direction along the axial length 105 to form a continuous wall as discussed herein.

Figure 3C:
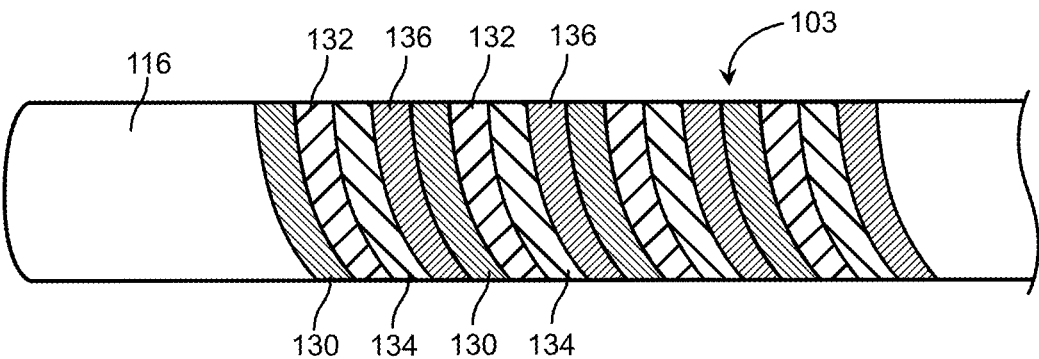
FIG. 3C illustrates a catheter section comprising a plurality of discrete polymeric strands of material that are wrapped about a mandrel or tube.

FIG. 3C illustrates a wall section 103 after a plurality of discrete polymeric strands of material in material sections 130, 134, 132, 136 are joined together a support structure 116. Section 103 can be incorporated into a medical catheter, medical device, and/or other tubing.

Figure 3D:
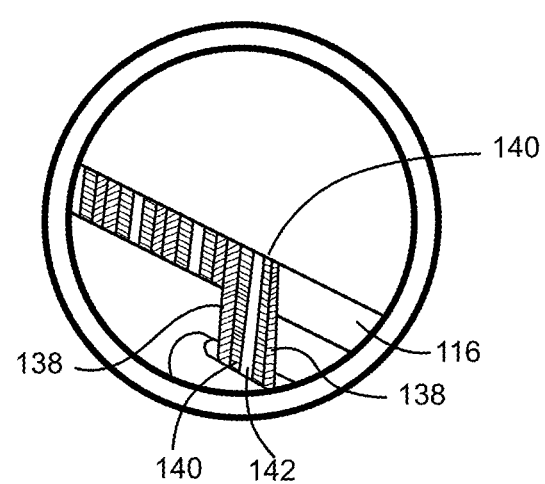
FIG. 3D illustrates an image of an example of a wrapping process.

FIG. 3D illustrates an image of an example of a wrapping process where strands of polymer form material sections 138, 140, 142 and are wrapped directly onto a catheter reinforcement braid 116. (Alternatively, the strands could be wrapped onto a mandrel, fused or partially fused together, and then transferred onto the catheter braid as conventional catheter construction). In this variation, the strands 138-142 are separate and are wrapped such that the strands are in contact for joining to form a sealed connection between adjacent materials such as by thermal fusing. However, any process that results in joining of adjacent materials can be used.

While the variations disclosed herein show a single layer of various material sections forming a wall of the tubing, it is noted that tubings can be formed from multiple layers where each layer comprise multiple material sections. Where each layer can have the same or different sequence of material sections.

Figure 3E:
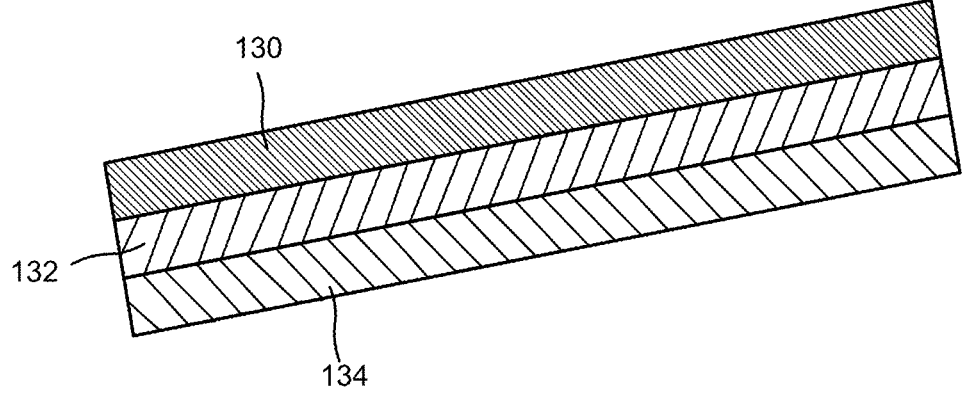
FIG. 3E illustrates a configuration where polymeric strands are secured together prior to being helically wound.

FIG. 3E illustrates a configuration where polymeric strands 130-134 that are secured together prior to being helically wound to form material sections 130-134. For example, the strands can be fused together or tacked together prior to winding.

Figure 3F:
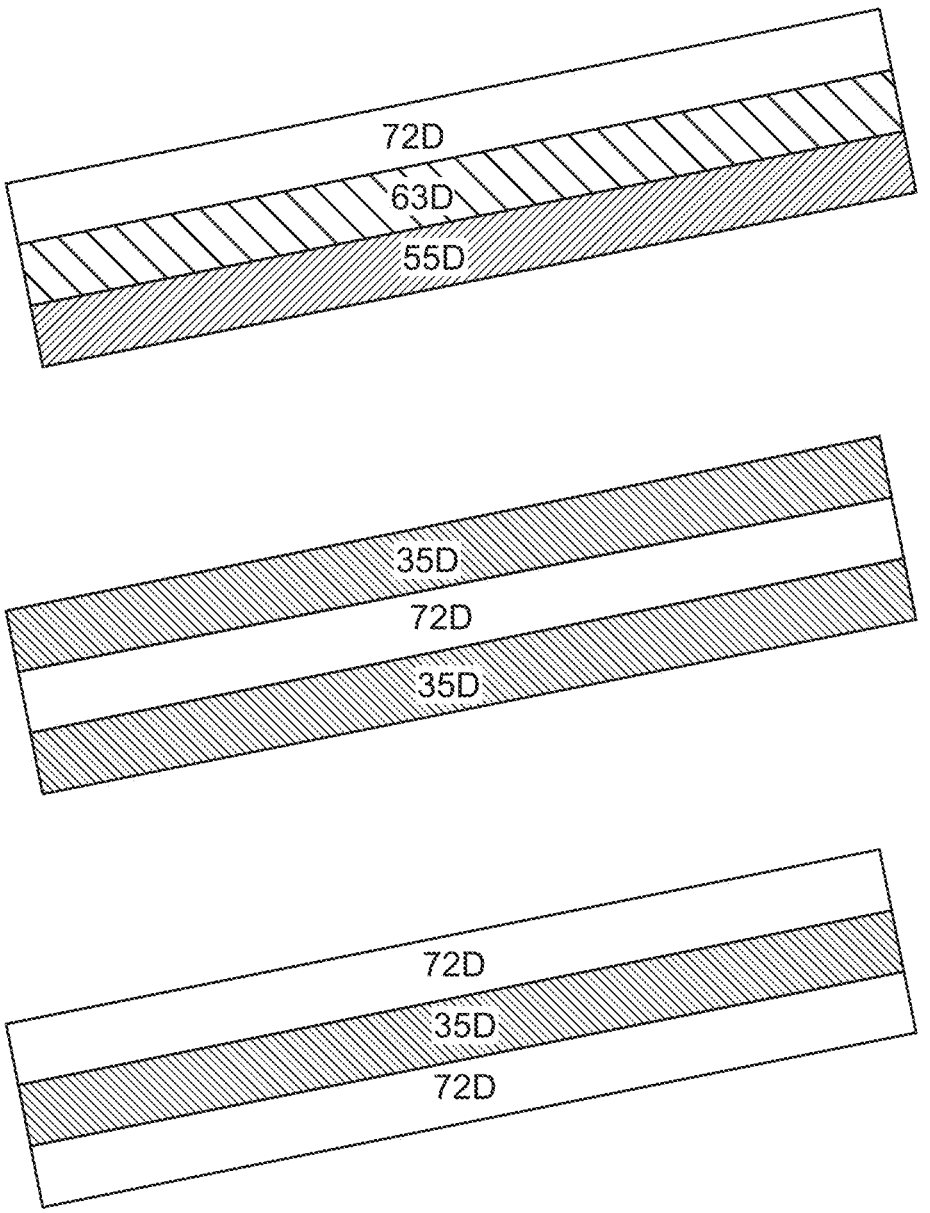
FIG. 3F illustrates three additional variations of polymer strands arranged having varying properties.

FIG. 3F illustrates three additional variations of polymer strands arranged having varying properties. In the illustrated example, the durometer of the strand is shown. However, the polymer strands can vary other properties as needed. As shown in the bottom-two variations, two strands of a similar configuration can be placed adjacent to a dis-similar strand. When formed into a tubular member the center material section will be bounded by material sections having the same polymer.

Figure 3G:
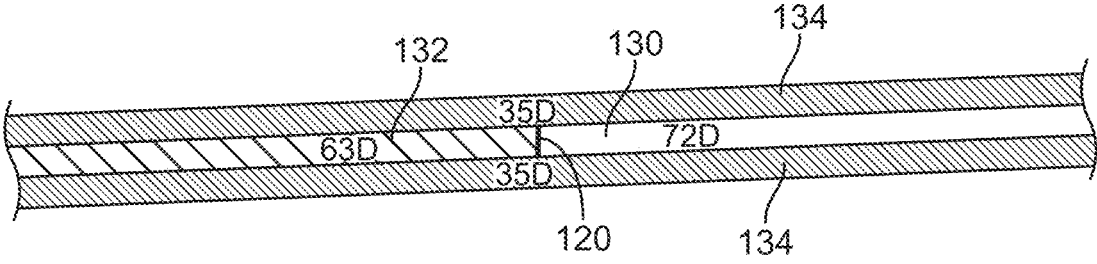
FIGS. 3G and 3H show additional variations of polymer strands joined together end-to-end and lengthwise prior to being helically wound and formed into a tubular body.
Figure 3H:
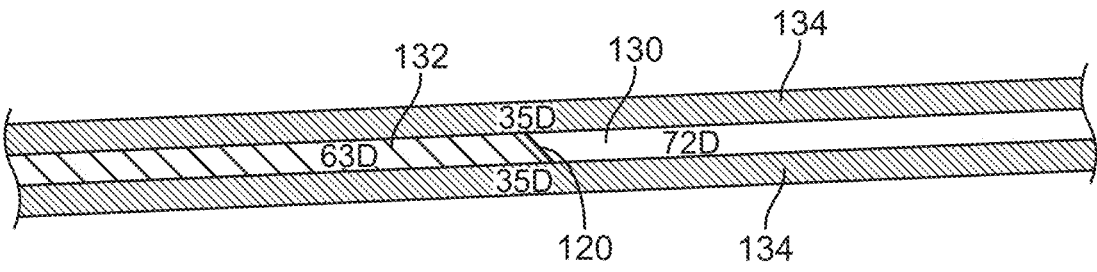

FIGS. 3G and 3H show additional variations of polymer strands 130, 132, 134, 130-134 joined together end-to-end and lengthwise prior to being formed into a wall where strands 134 will ultimately form the material sections on either side of the material section formed by strands 130 and 132. In this variation, strands 130 and 132 are joined end-to-end at a transition section 120 to allow for a transition of materials lengthwise along an axial direction of the finished catheter. This means that when formed into the tubular member/wall the center material section comprises material 130 joined to material 132 at edge 120. The joint or transition section 120 between strands 130 and 132 can be an abrupt transition section 120 as shown in FIG. 3G or an angled or tapered transition section 120 as shown in FIG. 3H.

Figure 3I:
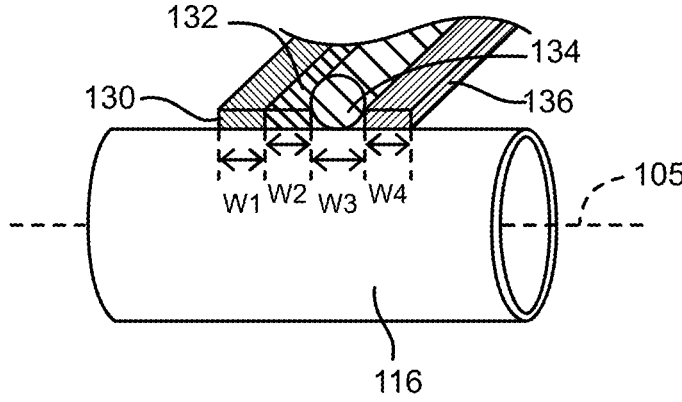
FIGS. 3I and 3J depict additional variations of non-uniform strands joined together prior to forming a tubing for use in a catheter construction.
Figure 3J:
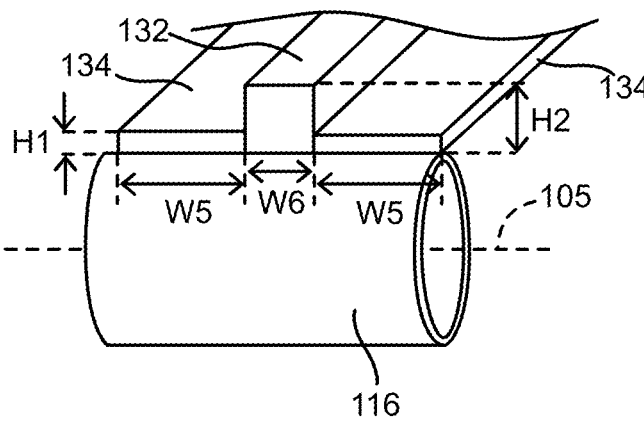

FIGS. 3I and 3J depict additional, but not exhaustive, variations of strands 130, 132, 134, 136 being joined together where the strands are not uniform. For example, FIG. 3I illustrates a strand 134 as having a circular cross-sectional shape. As noted above, any type of cross-sectional shape can be used. In such cases, a width W3 of the strand 134 can be considered its widest dimension along the axis. In some variations, the size of the strand 134 will cause the resulting material section to slightly protrude from a surface of the tube. FIG. 3J illustrates such a case, where a height H1 of certain strands 134 are joined with a strand 132 having a greater height H2. FIG. 3J also illustrates the widths W5 and W6 of the strands as not being uniform. Again, any permutation of shapes, sizes, widths, heights, etc., can be combined to make a polymer layer. It should be noted that any strand of material incorporated into a composite polymeric layer can include strands of material having a melt temperature different than one or more adjacent strands. It is also noted that in some variations, one or more strands can be non-meltable (i.e., a thermoset material, or metals, Teflon, etc.) that are mechanically held by the adjacent strands but do not melt. In additional variations, the non-meltable strand is used during formation of the tubing and then removed to create a void or pattern.

Figures 4A, 4B:
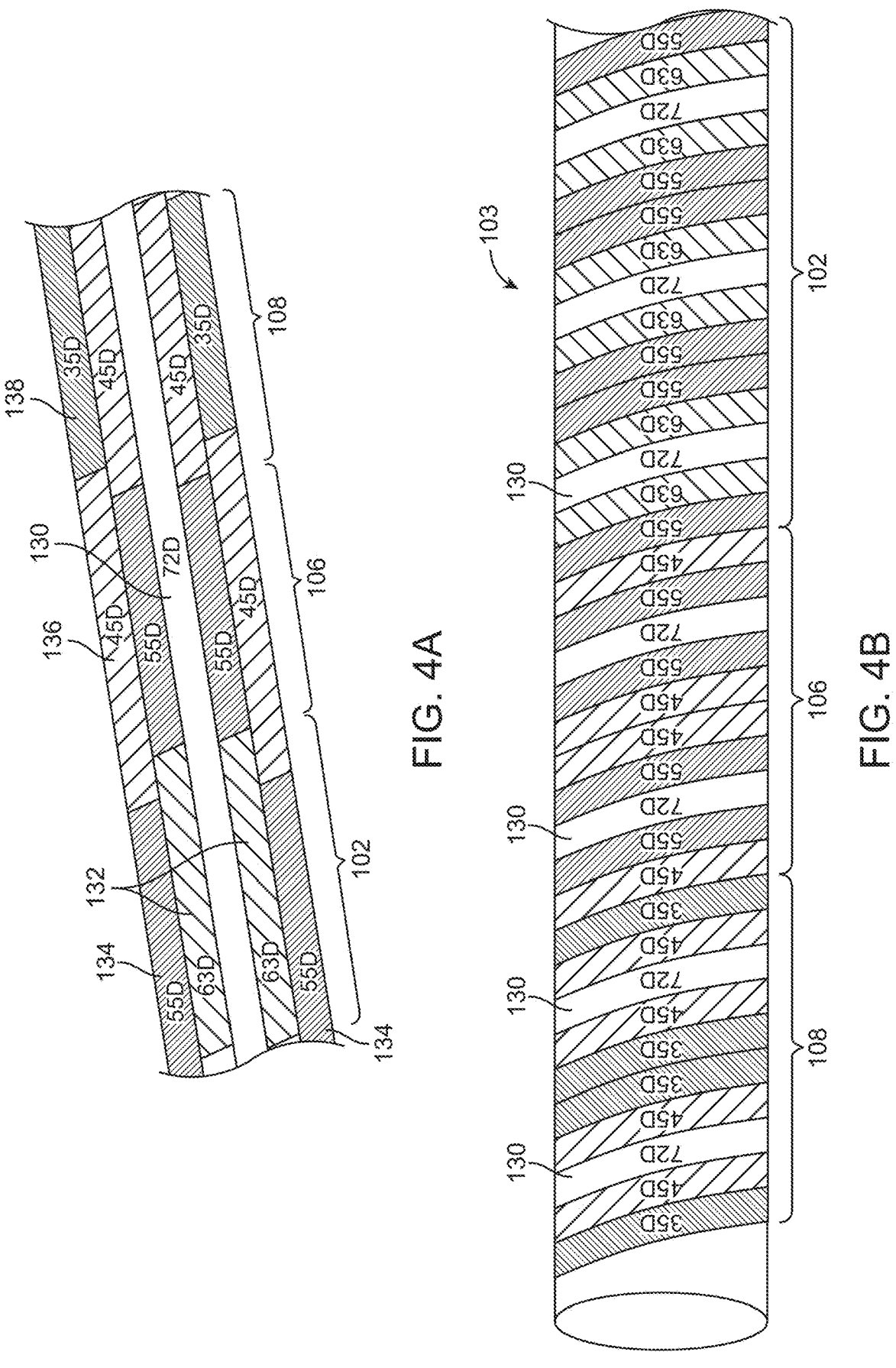
FIG. 4A illustrates another variation of a group of joined strands prior to forming the tubular section depicted in FIG. 4B.
FIG. 4B illustrates a catheter section formed from the strands shown in FIG. 4A.

FIG. 4A illustrates another variation of a group of joined strands 130-138 prior to forming the tubular section depicted in FIG. 4B. As shown, the strands comprise different properties resulting in different sections 102, 106, and 108 for the catheter. When wound, as shown in FIG. 4B, the varying of the composition of material sections 130-138 form different axial sections 102, 106, 108 extending lengthwise along the tubular layer 103. In both variations depicted in FIG. 4A and FIG. 4B, the strands/tubular layer 103 include a single strand 130 that will extend continuously as a material section 130 over a full length of the finished tube 103. In this example, the strand 130 comprises a 72D material and can be ultimately used as reinforcement for the finished catheter. (mainly used to transmit torque and provide stability through a normally soft and flexible distal region that usually does not transmit torque well and usually has poor stability).

Figure 5:
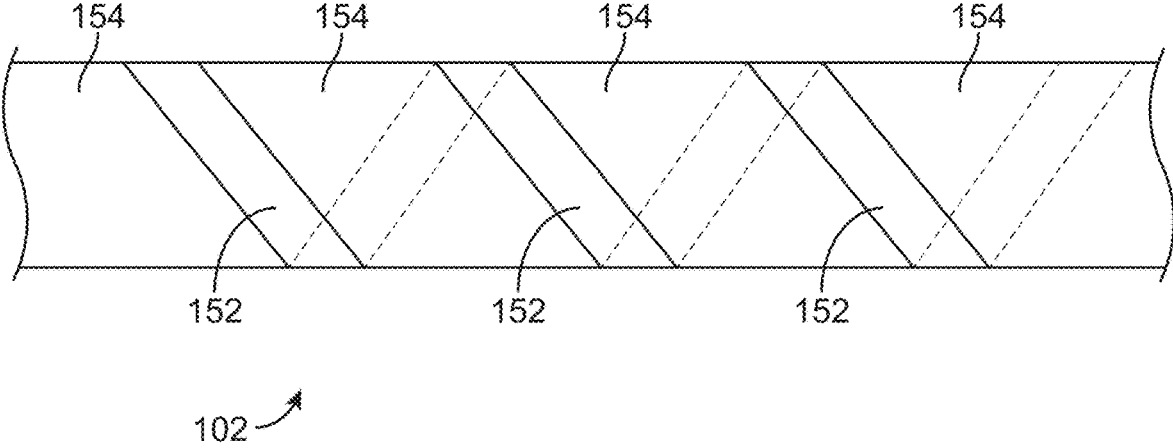
FIG. 5 shows a catheter section, which illustrates spacing of dis-similar strands.

FIG. 5 shows a section 102 of a tubing where strands 152 and 154 are joined to form the tube. The figure illustrates spacing of dis-similar strands 152 and 154. In the example, strands 152 can be separated by a second strand 154, where this second strand either comprises segments having the same width as strand 152 or the second strand 154 has a greater width than the first strand 152. As noted above, the width is measured along an axial length of the tube. For example, strand 152 can comprise a high durometer material while strand 154 comprises a relatively lower durometer material. In an alternate variation, strand 152 comprises a low durometer material while strand 154 comprises a high durometer material. For example, in one variation of the device a low durometer material could range between 35D to 45D while a high durometer material can range between 63D and 72D. Clearly, additional variations of material are within the scope of this disclosure.

Figure 6A:
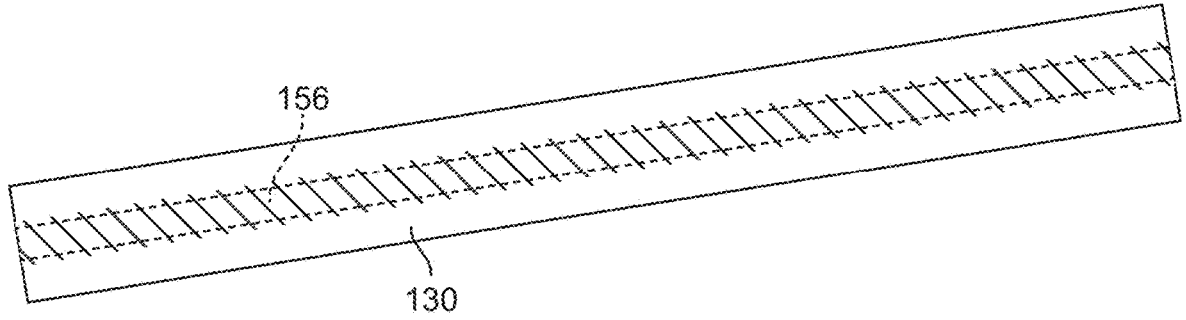
FIGS. 6A to 6C show variations of strands having reinforcing structures.
Figure 6B:
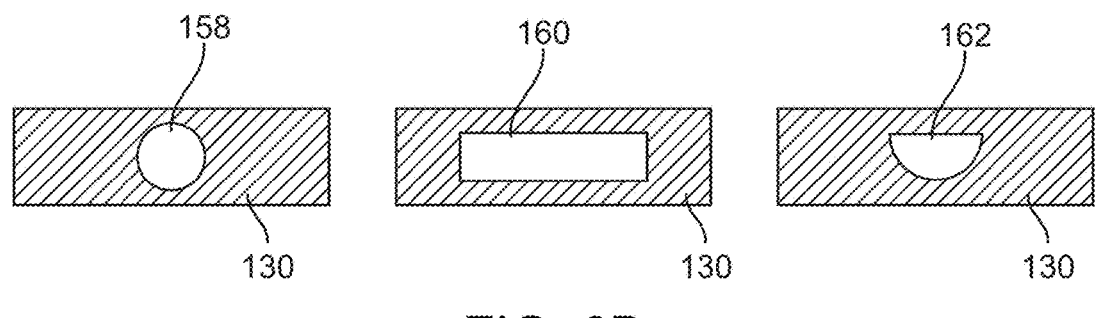
Figure 6C:
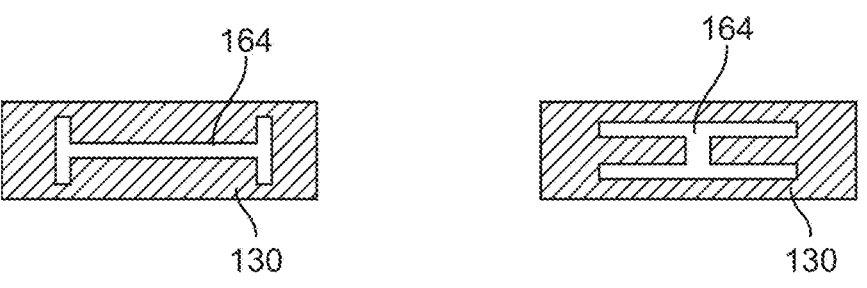

FIG. 6A illustrates an additional variation of a catheter construction described herein where a polymer strand 130 includes a support member 156 extending therethrough that reinforces the strand 130 or provides alternate structural and characteristics. The support member 156 can extend through a full length of the strand 130 or partially through a strand. Moreover, a variation of the reinforced strand 130 can include a plurality of support members that extend through a strand. FIG. 6B illustrates a cross-sectional view of a strand 130 to illustrate some cross-sectional shapes of reinforcement members. As shown, the reinforcement member can have circular 158 or elliptical cross section, the support member can have a rectangular or square 160 cross section, or the support member can comprise a D-shaped 162 cross section. The support member can comprise a metal, an alloy, or polymer. For example, the support member can comprise SS wire, a shape memory wire, a drawn-filled tube, or a composite fiber material. It can be in a cable, braid, coil, strand, etc., or any shape/structure/material used to provide support. FIG. 6C illustrates various complex cross-sectional shapes 164 for a support member within a strand 130. In certain variations, the catheter section can comprise different cross-sectional shapes in different sections of the catheter. For example, it was found that strands with a circular or oval cross-sectional shape are better suited for a distal region of a catheter while, strands with a D-shaped support member are useful at the mid or proximal region of the catheter.

Figure 7A:
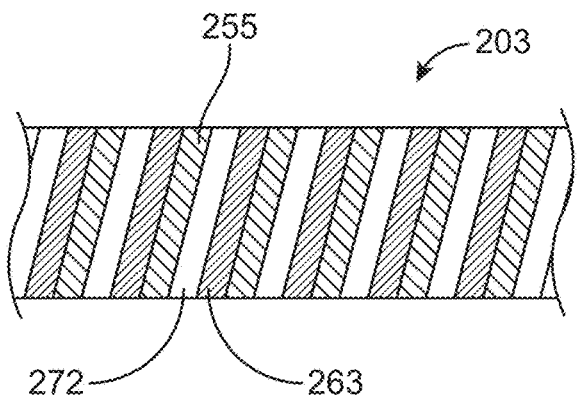
FIGS. 7A to 7F illustrate some examples of catheter sections formed from various polymers.
Figure 7B:
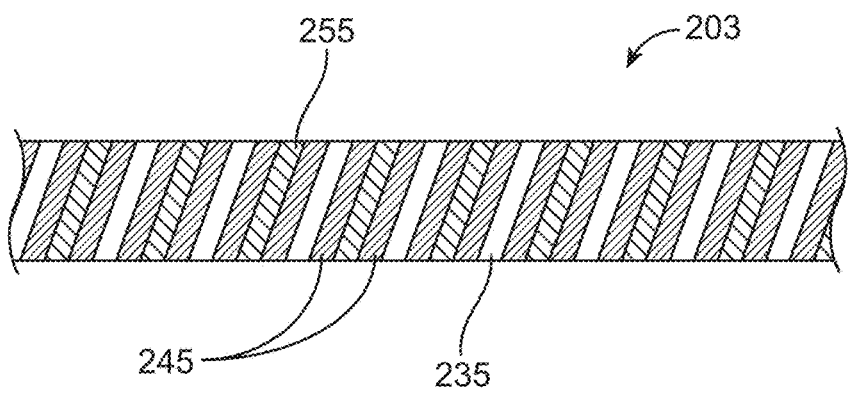
Figure 7C:
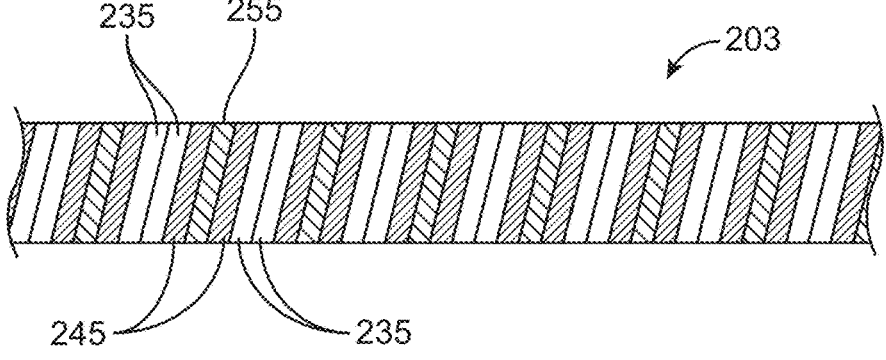
Figure 7D:
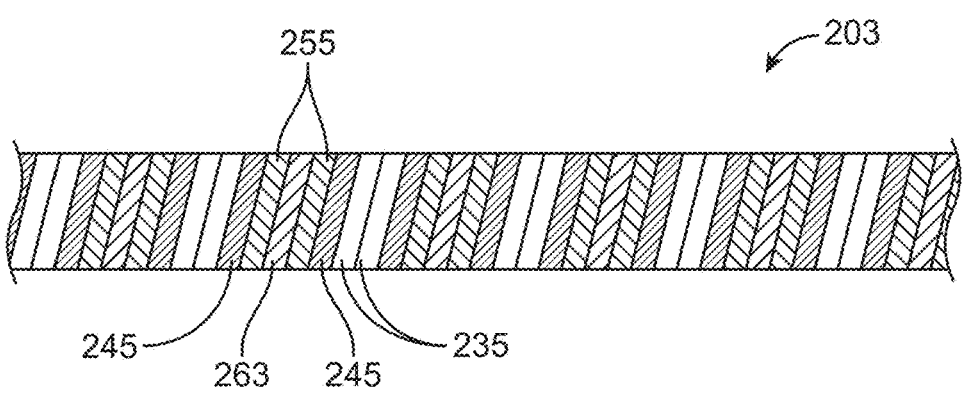
Figure 7E:
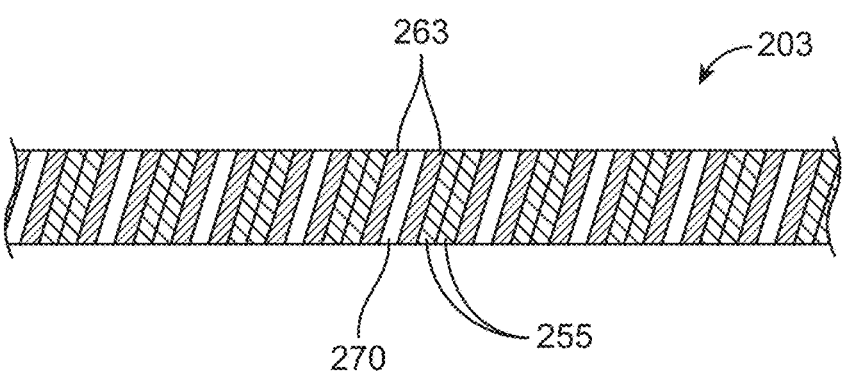
Figure 7F:
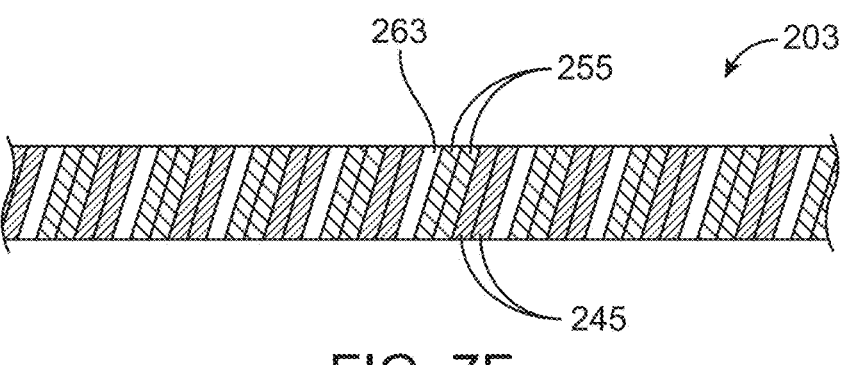

FIGS. 7A to 7F illustrate some examples of tubular sections 203 formed from various polymers to have multiple material sections extending in a spiral pattern along the tubing 203. For purposes of illustration in 7A to 7F, the materials properties are shown in association with the following element numbering: 35D—235, 45D—245, 55D—255, 63D—263, 72D—272. However, this association is intended to demonstrate variations of tubing 203. Any variation of materials can be used in the catheter constructions described herein. Furthermore, any tubing section 203 can be used in any segment of a completed catheter, as discussed herein. The illustrations of FIGS. 7A to 7F are intended to show a non-exhaustive combination of segments. In each figure, the pattern illustrated by the respective material sections 235, 245, 255, 263, 272 repeats to provide that segment of the tubing 203 with unique properties. For example, FIG. 7B illustrates a pattern where a 55D material section 255 is immediately between two 45D material sections 245 and that assembly is between two 35 D material sections 235. This configuration can provide characteristics that allow for a "shock absorber" effect. In FIGS. 7C, 7D, 7E, and 7F certain strands are doubled during construction of the tubing 203 to provide for wider material sections with that configuration. For example, the material section 235 in FIG. 7D is shown to be near twice the width of material sections 245, 255, and 263. FIG. 7E shows material section 255 as nearly twice the width of sections 263 and 270. FIG. 7F shows material sections 245 and 255 as being near twice the width of section 263. Again, the illustrated variations are intended to provide a non-exhaustive sample of variations for possible catheter construction.

Figures 8A, 8B:
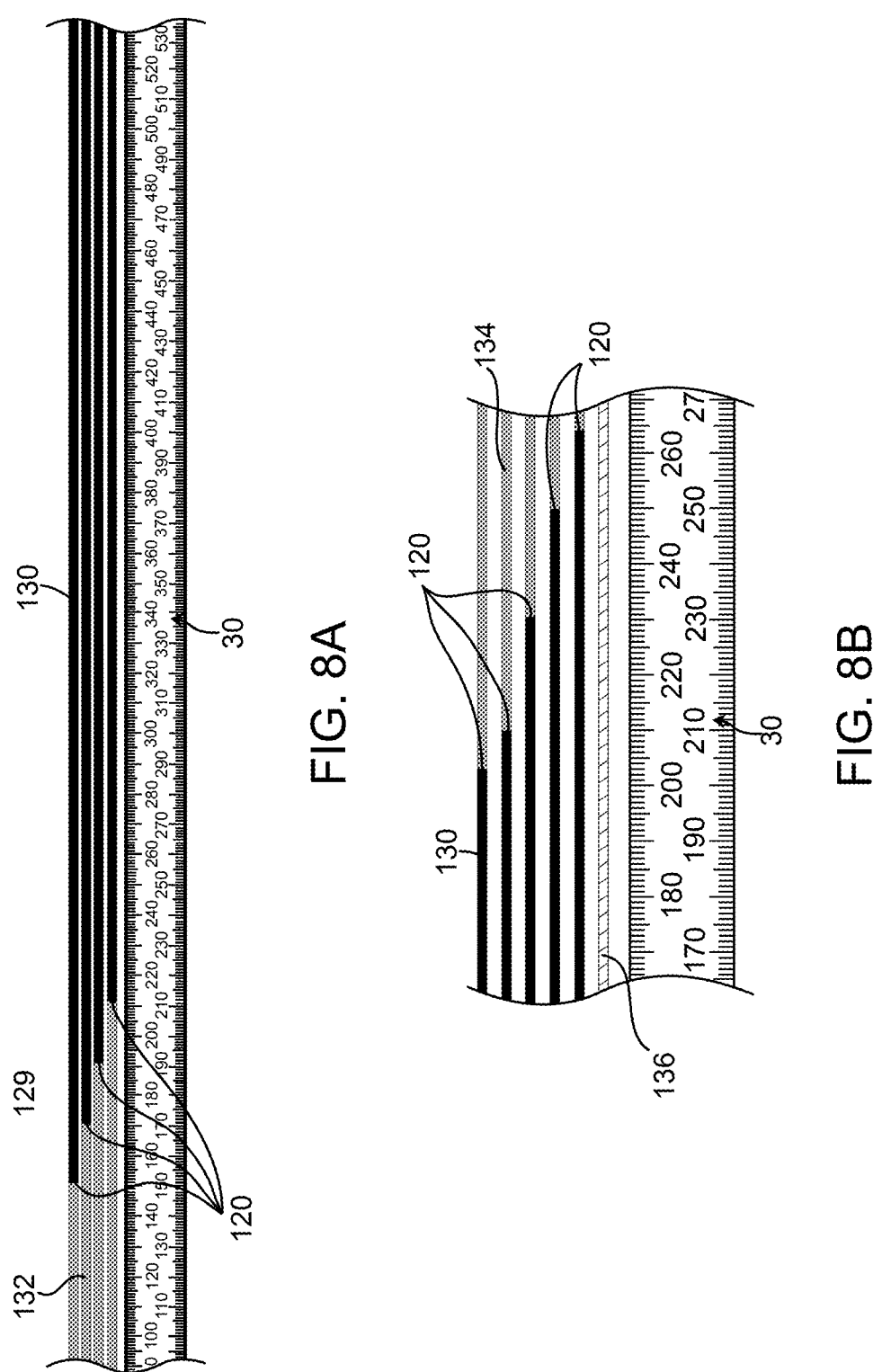
FIGS. 8A and 8B show a picture of a plurality of strands extending next to a scale to illustrate a perspective of the strands for one variation of the catheter construction.

FIGS. 8A and 8B shows an example of strands 130 and 132 extending next to a scale 30 to illustrate a perspective of one example of strands 130 and 132 that ultimately form a tubular member as described above where the overlap or staggering of the polymer end-joint locations, produces a finished polymer tube/catheter construction with a transition region 129 that is significantly improved over conventional catheter constructions. FIGS. 8A and 8B demonstrate how the overlap or staggering of the polymers at individual transition sections 120 (where the materials each have a butt-joint location) such that the end of 130 adjoins the end of 134), and will, when wrapped, result in a significantly improved transition region 120 over the conventional catheters discussed above. As shown, the configuration of FIG. 8A includes staggered transition sections 120, which creates a transition region 129 similar to that shown FIG. 9A. As noted herein, when strands 130 and 132 are formed into a tubular member, the strands 130 collectively form a material section that changes from a first material over region 129 to a second material having the material of strands 132. FIG. 8B shows a variation similar to the example of FIG. 8A with strands 134 joined/spliced end-to-end with strands 130. However, strand 136 remains continuous. When fabricated into a tubular member, strands 134 form a material section that changes in materials as described with respect to FIG. 8A, but the tube section formed by FIG. 8B includes a material section formed by strand 136 that remains constant.

Figure 9A:
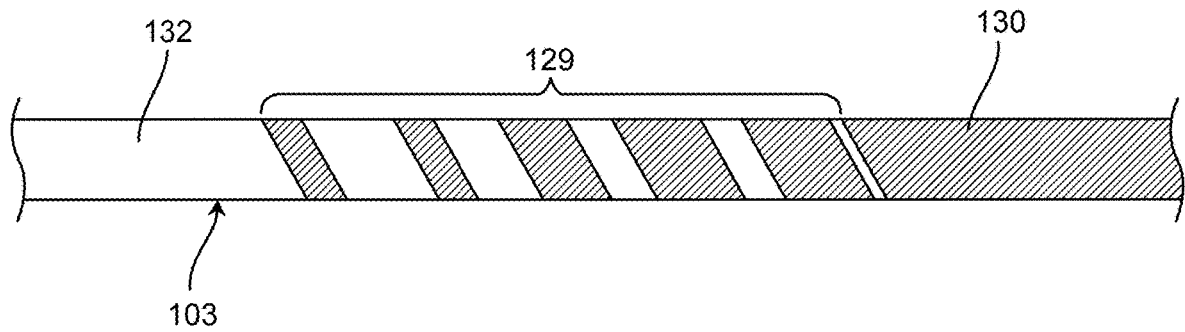
FIGS. 9A and 9B show two examples of sections of catheters having an outer layer that can be incorporated on a catheter or used as a stand-alone device.
Figure 9B:
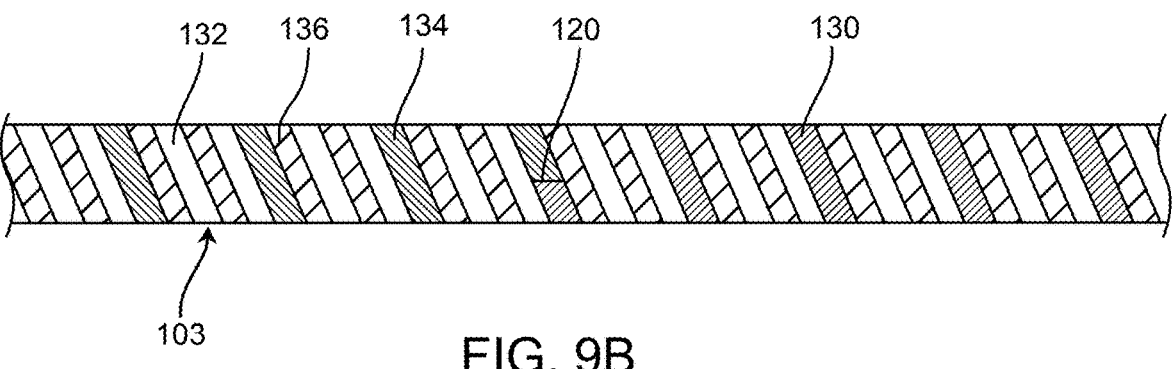

FIGS. 9A and 9B show two examples of sections of catheters having an outer layer 103 that can be incorporated on a catheter or used as a stand-alone device/structure. FIG. 9A illustrates a material section 130 formed from a first polymer and a material section 132 formed from a second polymer. The outer layer 103 includes a lengthwise region 129 of the tubular layer where a width of the first material section 130 and a width of the second material section 129 both change in width along the lengthwise region 129 causing a structural property to change over the first lengthwise region 129. As shown, the right side of FIG. 9A comprises a tubular member where an entirety is formed from material section 130 and a left side where an entirety of the material section 132 is formed from material section 132. In the transition region 129, the widths of the respective material sections inversely change along the lengthwise region 129 such that as the width of the first material 130 decrease towards the left and the width of the second material section increases. These transition regions can be made as long and gradual as desired, by adjusting the length of section 129, and by adjusting the number of strands/ribbons used, to give drastically improved and superior transition regions compared to conventional catheters.

FIG. 9B illustrates a variation of a tubing 103 having a plurality of material sections 130, 132, 136 spirally wound to form the tubing 103 where the tubing 103 includes a joint 120 where material section 130 changes to a different material 134, that continues in the spiral pattern of material 130. This end-to-end joining of materials allows the material section to continue while changing materials.

Figures 10A, 10B:
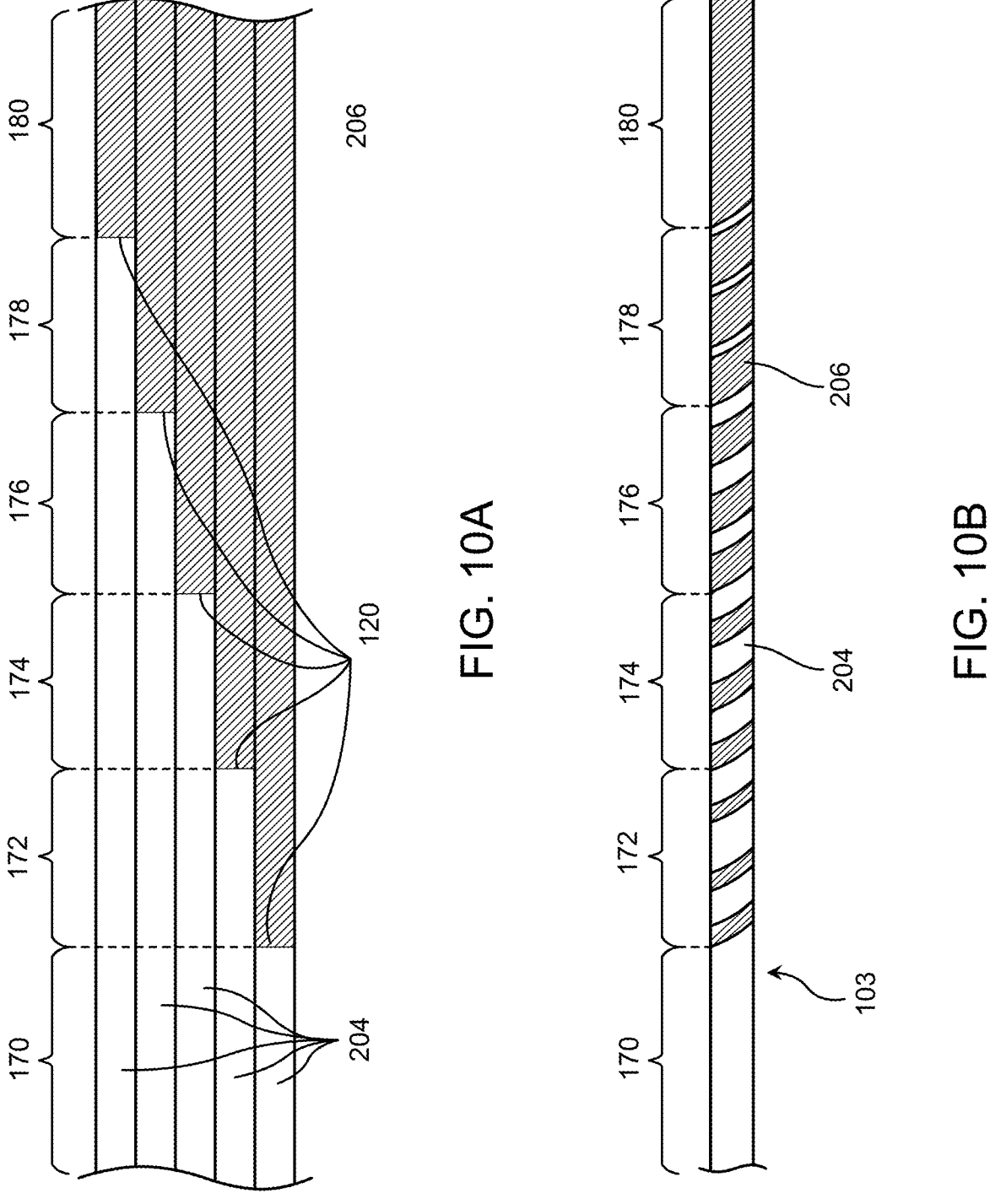
FIGS. 10A to 10D illustrate another variation of the device that changes polymers incrementally to construct a wound catheter with a gradually changing transition region between different sections of the finished polymer tube.
Figures 10C, 10D:
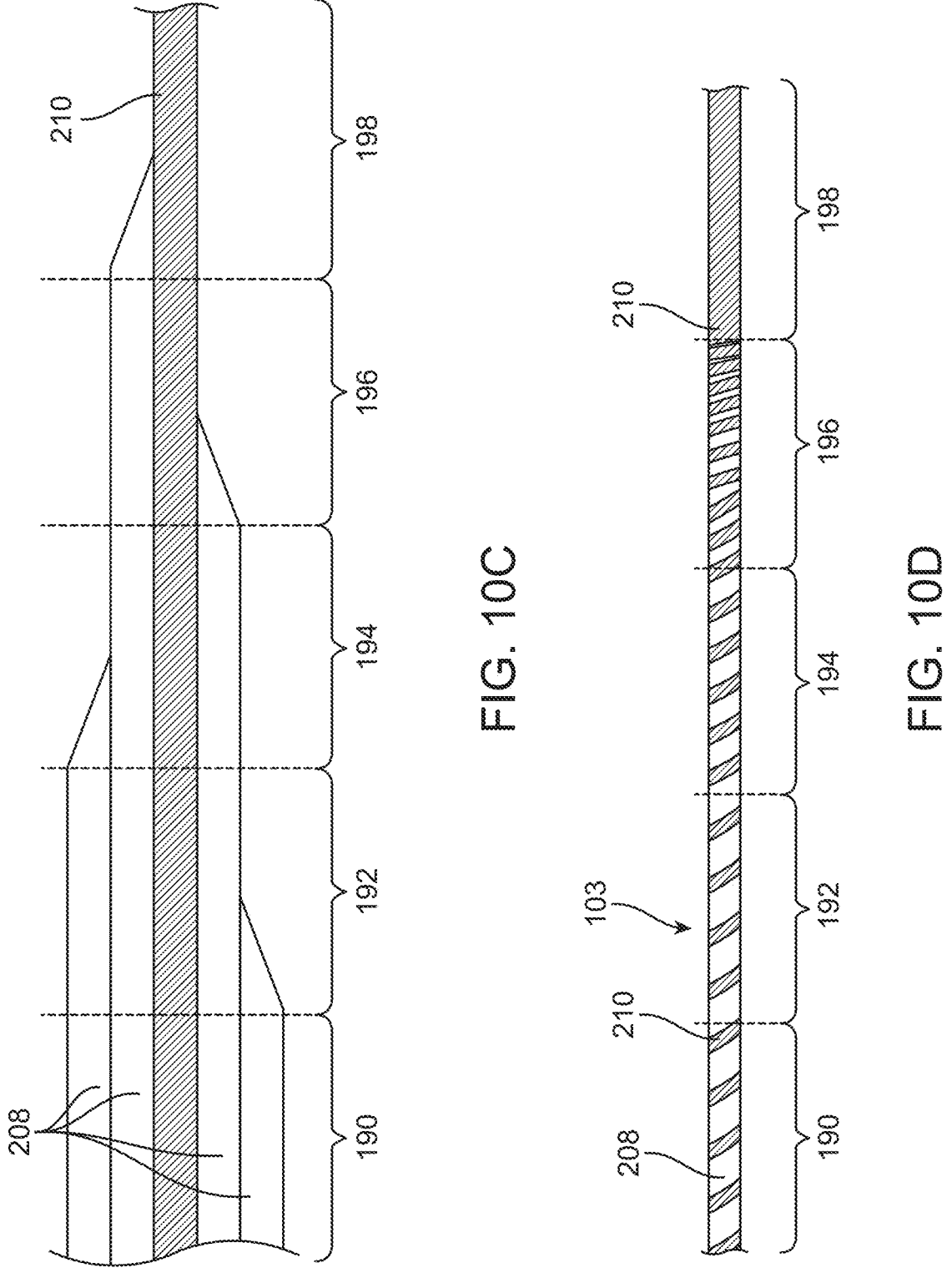

FIGS. 10A to 10D illustrate another example of an arrangement of strands to form a tubular member for use in a catheter. FIGS. 10A and 10C show a group of joined strands that can be varied to produce configurations as shown in FIGS. 10B and 10D, respectively. FIG. 10A illustrates a 5-strand construction, where one end of the joined strands comprises strands 204 of a first polymer. The strands 204 of the first polymer are each replaced at individual transition sections 120 that are staggered to gradually replace strands 204 with strands 206 of a second polymer over a transition region comprising length 172, 174, 176, and 178. This construction allows for a gradual variation over the transition region 172, 174, 176, 178 along the finished tubular assembly 103 (as shown in FIG. 10B) that has the properties of the first polymer in a first lengthwise region 170 and gradually changes over transition region 172, 174, 176, and 178 to the properties of the second polymer until lengthwise region 180 comprises all of the second polymer. The transitioning of materials in lengthwise regions 172, 174, 176, 178 represents an example of gradually transitioning material properties over a lengthwise transition region of a tubular assembly 103 or finished catheter construction. Clearly, any number of material sections or widths of material sections can be used to increase or decrease the rate of transitioning material properties. Moreover, variations of the devices described herein do not require staggering of transition sections 120. While staggering is usually desired to obtain a gradual transition, the transition regions can comprise an abrupt change in materials when desired.

It is noted that a transition section shall be used to describe the changing of one or more material strands with a different material. The term transition region shall describe the overall effect of the one or more transition sections. In some variations, the transition region does not include any transition sections because a material simply terminates. Therefore, catheter constructions of the present disclosure can have a transition region that gradually changes material properties over an axial length, or, alternatively, the transition region can be a region of an abrupt change in material properties.

FIG. 10B also illustrates that each lengthwise region 172, 174, 176, 178 comprises at least two material sections 204 and 206, where a width of a material section 204 or 206 increases or decreases while the other material section 206 or 204 decreases or increases respectively. The variation of the tube 103 shown in FIG. 10B also includes lengthwise regions 170 and 180 entirely formed a single material section. Again, any tube construction 103 discussed herein can be incorporated into a catheter construction as shown in FIG. 2A, or such tube construction 103 can be incorporated into any medical device or non-medical device.

As shown, the catheter section can comprise the various sections: section 170 consists of 5 strands of a first polymer (5 and 0); section 172 consists of 4 strands of the first polymer and 1 strand of the second polymer (4 and 1); section 174 comprises 3 strands of the first polymer and 2 strands of the second polymer (3 and 2); section 176 comprises 2 strands of the first polymer and 3 strands of the second polymer (2 and 3); section 178 comprises 1 strand of the first polymer and 4 strands of the second polymer (1 and 4); and section 180 comprises 5 strands of the second polymer (0 and 5). The construction of FIG. 10A produces the catheter shown in FIG. 10B after the strands are helically formed and melted into a catheter section.

FIG. 10C illustrates a plurality of joined strands where section 190 comprises 4 strands 208 of a first polymer and a single strand 210 of a second polymer (4 and 1). As shown, in the change to region 192 one strand 208 is tapered leaving only four strands (3 and 1). The next section 194 another strand 208 is tapered leaving only 3 strands (2 and 1). The process continues through sections 196 (1 and 1), until the strand 210 of the second polymer remains. The wrapping of the joined strands is adjusted (e.g., the pitch is altered) such that the reduction in number of strands does not leave any openings or gaps between strands. This construction produces a tube construction 103 similar to FIG. 10D As shown, the tubular construction 103 includes two material sections in lengthwise region 109, the width of the material section 210 increases in section 192 relative to section 190 while the width of material section 208 decreases in section 192 relative to section 190. The widths of material sections 208 and 210 continue to inversely change through lengthwise regions 194 and 196 until region 198 includes a single material section 210. The construction shown in FIG. 10D shows a tubular section 103 having transition regions 192, 294, 196 where the material sections change but there are no transition sections of materials 208 since the material just terminates as shown in FIG. 10C. While the construction of FIGS. 10A/10B and 10C/10D are different; both designs produce a shaft that transitions from a first material property to a second material property using a very gradual basis. This graduation and uniformity are significantly greater than what can be produced with conventional catheter technology. One example of the material properties is stiffness/softness. For example, the catheters of 10B and 10D can transition from a relatively stiff material property at, e.g., 170 of FIGS. 10C and 190 of FIG. 10D to a much softer material property at, e.g., 180 of FIG. 10B and 198 of FIG. 10D. The transition region (e.g., 172-178 FIG. 10B and 192-196 of 10D) can be customized by selection of polymers, length of transitions, etc., to produce transitions that were simply not found in currently available commercial catheters. It is also noted that the lengths of regions 170-180 and 190-198 (as well as the lengths throughout this disclosure) are intended to convey the principles of the present designs. The lengths are not required to be the same and are not to scale unless otherwise claimed.

Clearly, the length of each section shown in FIGS. 10A and 10C is intended for illustrative purposes only. In addition, any number of polymer strands can be used along with any number of polymers. Moreover, it is noted that in FIG. 10A, a material section can be considered all of the separate elements 204 of the same material. Therefore, region 170 includes a material section that changes in width stepwise to region 172 and so forth. The change in width can be stepwise or incremental, as shown. Alternatively, the change can be tapered such that the change in width is continuous, as shown by regions in FIG. 10C where the ends of material 208 taper off.

Figure 11A:
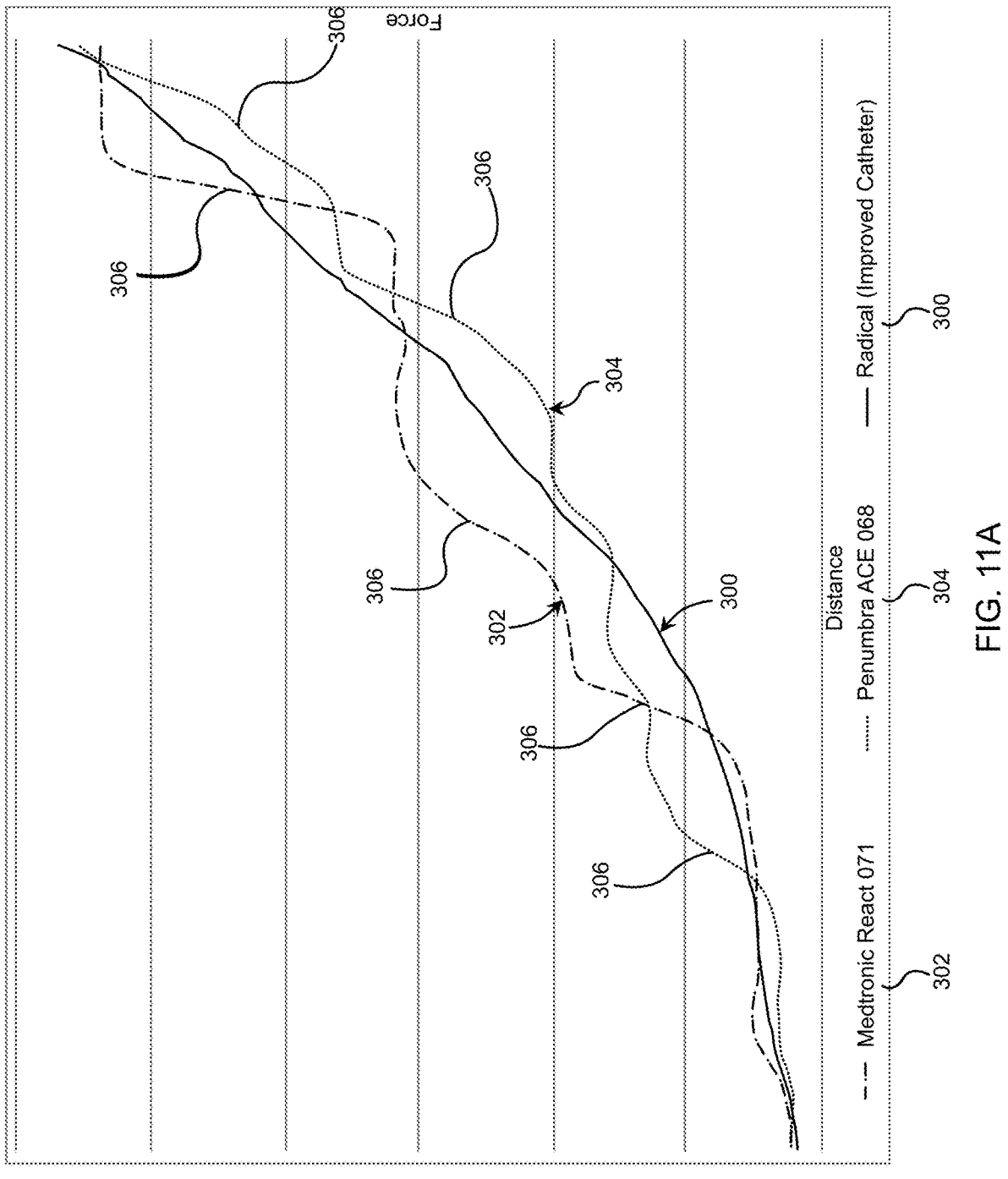
FIG. 11A illustrates a graph of bend stiffness versus shaft location to aid in understanding the ability of catheters of the present disclosure to produce transition regions that are significantly improved over the currently available catheters.

FIG. 11A illustrates a graph of bend stiffness versus shaft location to aid in understanding the ability of catheters of the present disclosure to produce transitions regions that are significantly improved over the currently available catheters. FIG. 11A illustrates the result of a test where a force is measured to displace a catheter by a given distance, commonly known as a 3-point bend test. The catheter is supported at two points such that a gap between the two points will be deflected by the given distance. The force required to produce this deflection is measured and graphed to correspond to a distance from the distal end of the catheter. For example, the left side of the graph shows the amount of force required to displace the catheter section at the closest point to the distal end of the catheter (i.e., the distal end). The right side of the graph of force shows the amount of force required to displace the catheter section at the closest point to the proximal end of the catheter. The three catheters tested in this manner included a catheter 300 constructed under the present disclosure, a commercially available catheter 302 manufactured by Medtronic (React 071), and a commercially available catheter 304 manufactured by Penumbra (ACE 068). The graph shows the improved catheter 300 as having a gradual increase in bend stiffness with no sudden or irregular increases in bend stiffness. In contrast, the graphed data of the Medtronic catheter 302 bend stiffness shows two significant regions of abrupt changes in properties 306. The graphed data of the Penumbra catheter 304 bend stiffness shows three significant regions of abrupt changes 306.

Figure 1D:
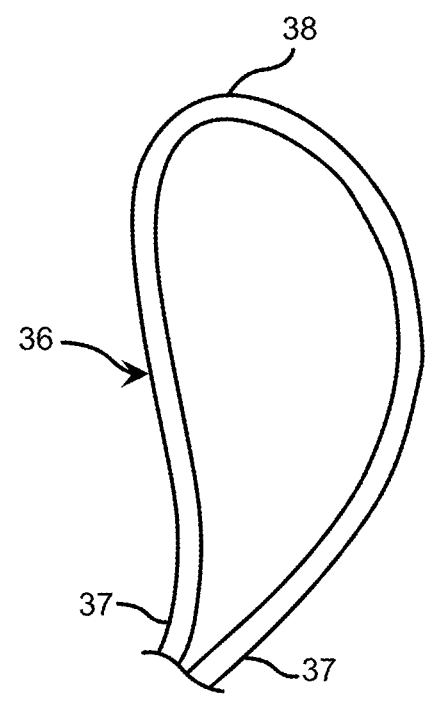
FIG. 1D shows a representation of a photo of a catheter having abrupt changes in structural properties between regions and is held in a bent or curved profile such that the abrupt change of the catheter causes the bend radius to be irregular.
Figure 11B:
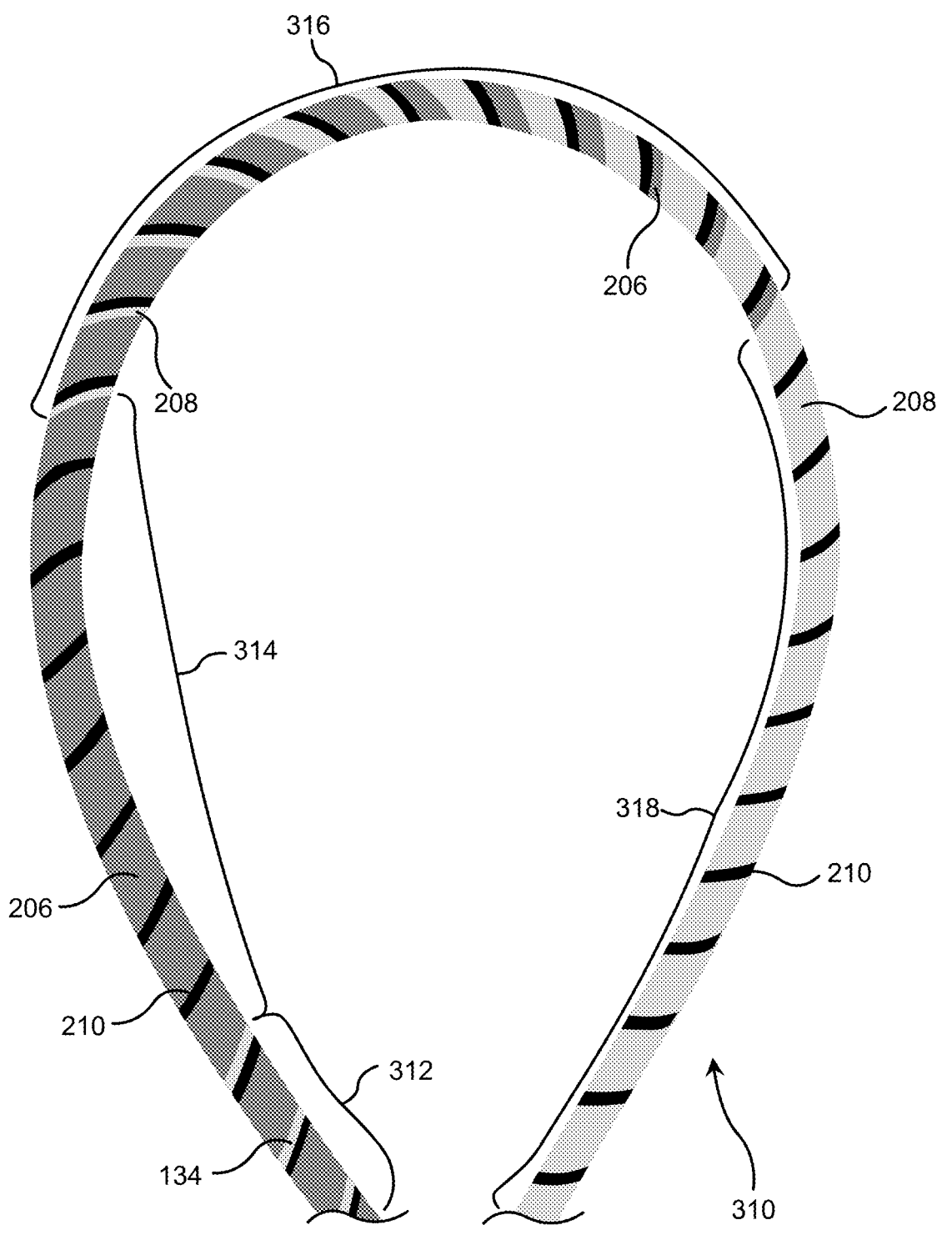
FIG. 11B shows an image of a section of a catheter constructed in accordance with the disclosure herein where the catheter section is held in a position similar to the position of the catheter shown in FIG. 1C.

FIG. 11B represents a section of a catheter constructed in accordance with the disclosure herein where the catheter section is held in a position similar to a position of the catheter shown in FIG. 1D. However, the improved catheter 310 is constructed in accordance with the disclosure such that materials are actively selected to provide desired properties and characteristics of the catheter 310 over various lengthwise regions 312, 314, 316, and 318 to avoid any areas of abrupt changes that would otherwise cause bending irregularities. FIG. 11B shows just one example of a catheter 310 using materials 134, 206, 208, and 210. Clearly, any number of combinations, as described herein, are within the scope of this disclosure. As shown, lengthwise region 312 includes three material section of materials 134, 206 and 210. Lengthwise region 314 includes two material sections of materials 206 and 210. Lengthwise section 316 includes three material sections of materials 206, 208, and 210. This section also shows material sections changing in width such that a thickness of material/material section 206 decreases and material/material section 208 increases in a direction towards lengthwise section 318. Lengthwise section 318 includes two material sections of materials 208 and 210. The end result of the construction of catheter 310 is that length-wise sections 312 and 314 comprise significantly different structural characteristics as compared to lengthwise section 318 but the change is sufficiently gradual to avoid significant discontinuities in bending stiffness.

Figure 12A:
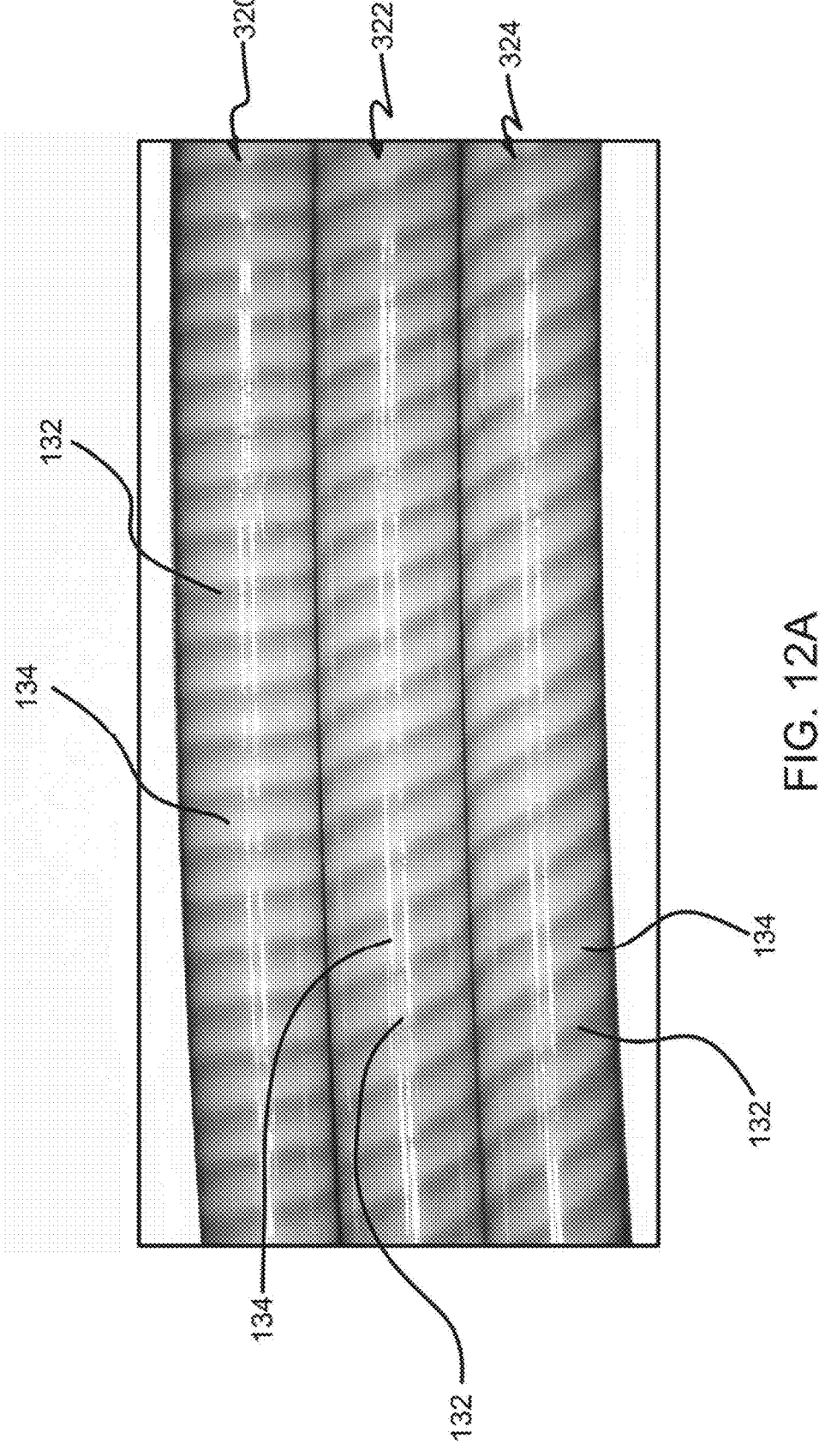
FIGS. 12A and 12F show images of various catheters to show variations of patterns that can be formed in joined polymer strands to produce features and/or patterns in a catheter section.

FIGS. 12A to 12D are greyscale images of exemplary catheter constructions under the present disclosure. FIG. 12A illustrates 3 different catheter sections, 320, 322, and 324, each having different helical pitch angles (i.e., the angle the material section 134, 132 makes with an axis of the catheter). Catheter 320 shows a near radial angle (meaning the angle is almost perpendicular to the axis). The construc-tion for this catheter section included two strands: one strand of material 134 and one strand of material 132. Catheter 322 shows an intermediate pitch angle. The construction for this catheter section included 4 strands: one strand of material 134, one strand of material 132, one strand of material 134 and one strand of material 132. Catheter 324 shows an increased pitch angle relative to catheters 320 or 322. The construction for this catheter section included 6 strands: one strand of material 134 and one strand of material 132 repeated three times. The greater number of strands used during construction allows for a greater increase in pitch angle.

Figure 12B:
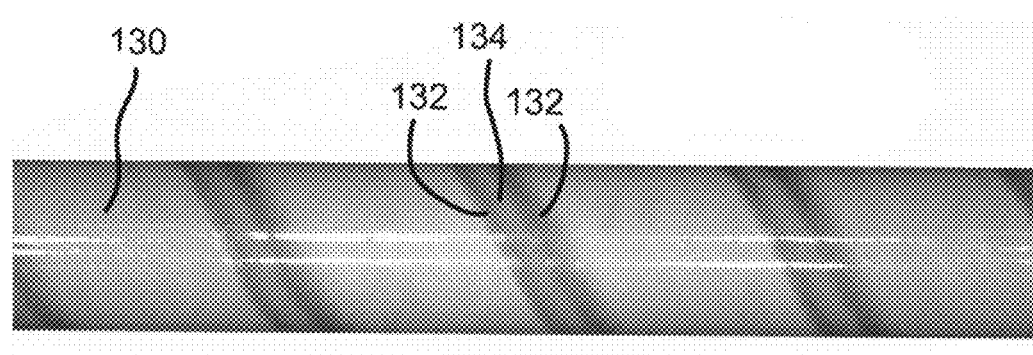
Figure 12C:
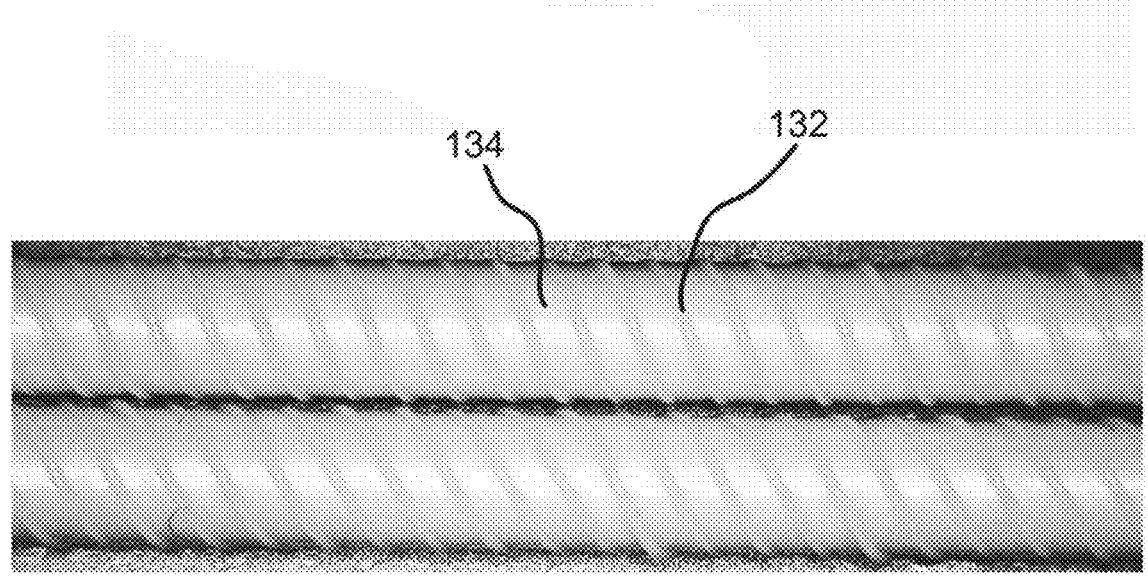
Figure 12D:
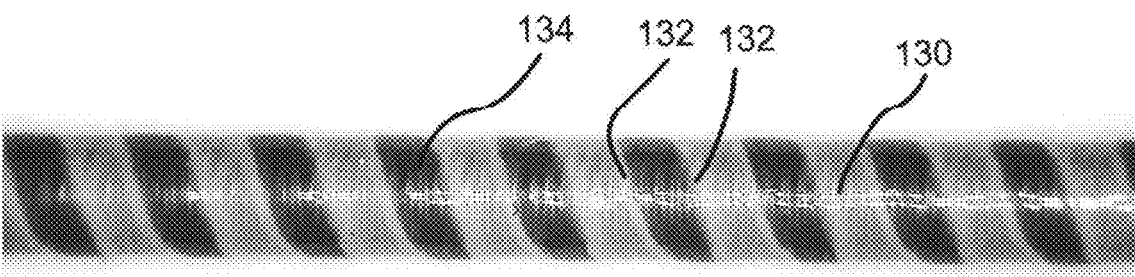

FIG. 12B shows another greyscale image of another variation of a constructed catheter section having two mate-rial sections of the same material on either side of a material section having a flexible material 134 with a material section 130 having a larger width. Such a configuration can com-prise a "shock-absorber" if materials 132 are stiffer materi-als. FIGS. 12C and 12D show catheters constructed accord-ing to the present invention with undulating outer surfaces. FIG. 12C shows a greyscale image of another example of a constructed catheter section similar made in a similar man-ner as the construction shown in FIG. 3J. In this variation, a height of material 132 was greater than a height of the adjacent material 134, and a width of material 132 is less than adjacent material 134. In spite of the height differences, the materials were able to be fused together to form the polymer layer. FIG. 12D illustrates another catheter where material section 134 has a diameter that is greater than adjacent materials 132 and 130. In another variation, the undulating surfaces can be formed using one or more materials during the fusing process (e.g., as described in FIG. 3A) with a non-fusable material (e.g., a high melt-temperature polymer such as PTFE, a metal alloy, etc.) on top of the strands such that the non-fusable material is removed to leave a void in the finished polymer layer.

Figure 12E:
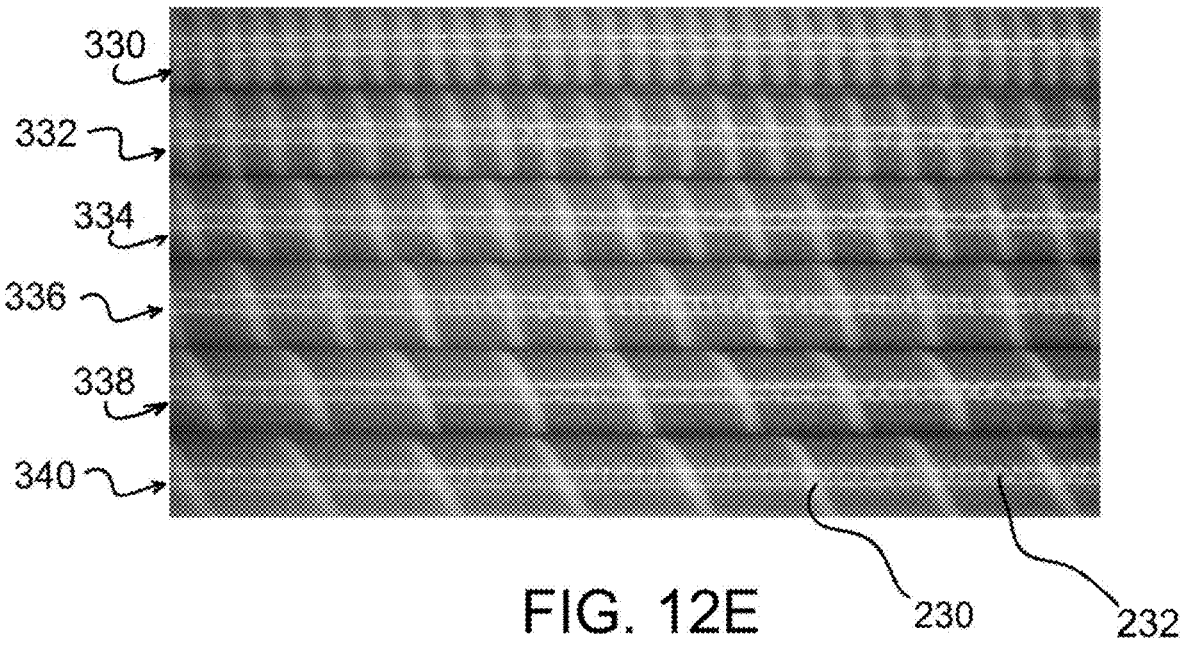
Figure 12F:
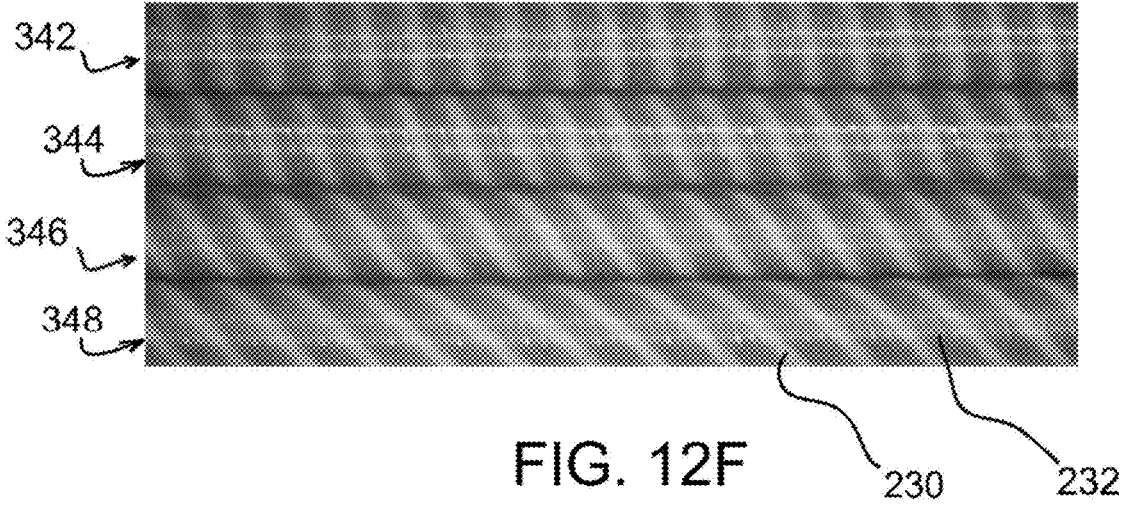

FIGS. 12E and 12F show pictures of variations of tubing 330-348 that can be incorporated into a catheter or used as a tube device without a catheter construction. FIGS. 12E and 12F show two material sections, 230, 232 that can comprise any variation of materials. In one example, FIG. 12E shows section 230 comprised of a hard 72D durometer ribbon (used as a torque coil) embedded in section 232, comprising a softer 60A durometer ribbon. The pitch (i.e., spacing) of material 230 increases from 330 to 340 by increasing the number of material sections in each unit, i.e., tubing 330 has a single material section 230 with material section 232. In contrast, construction 340 was formed from construction that included multiple strands of material 230 and multiple strands of material 232.

FIG. 12F shows a picture of four tubings 342, 344, 346, and 348 where an angle of material section 230 and material section 232 varies in each tube. In each of these units, the spacing (i.e., pitch) of material section 230 white 72D coil does not change (i.e., width of material section 232 in between material section 230 is the same dimension in each of the units). However, the angle of the material section 230 changes in each unit. For example, tube 342 shows an angle of material section 230 that is the most radial (i.e., extending in a radial direction from the tube), while the bottom tube 348 comprises the most axial or linear material section 230. Tube 342 comprised three strands: one strand 230 and two strands 232 to produce material section 230 and 232. Tube 344 was constructed with 6 strands: 230×1+232×2+230×1+232×2. Tube 346 was constructed from nine strands, and tube 346 was constructed from 12 strands using the same arrangement.

Figure 13A:
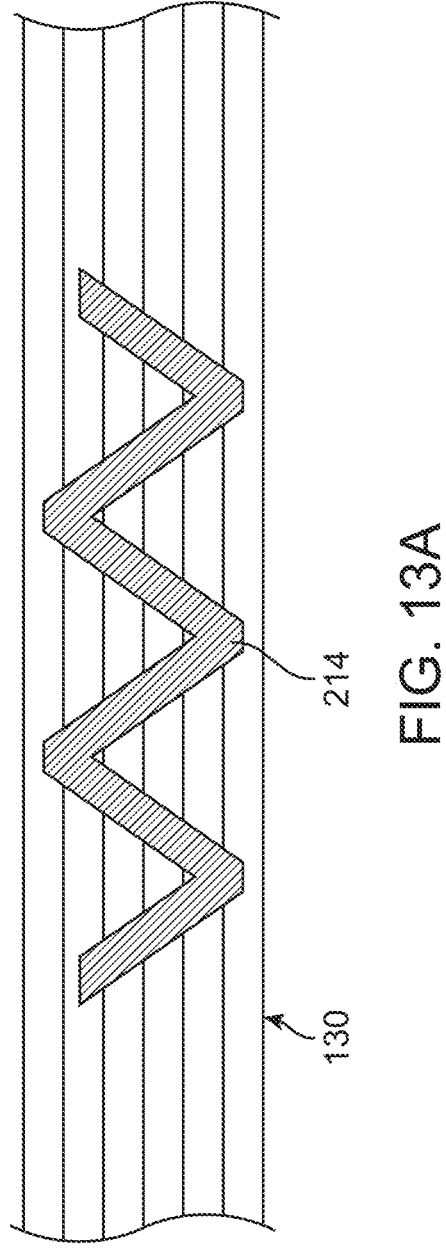
FIGS. 13A and 13B show a plurality of material sections having additional discrete materials formed therein.
Figure 13B:
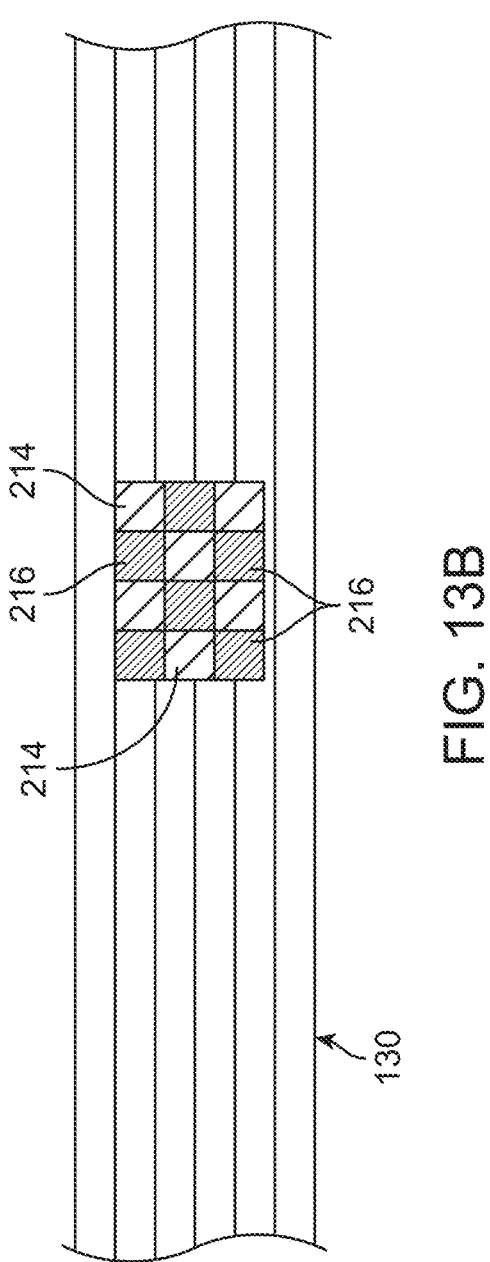

FIGS. 13A and 13B depict another feature of the catheter construction where a plurality of strands (either a similar polymer or different polymers) is joined together, as dis-cussed above. However, in these variations, a variety of discrete materials (i.e., polymers, metals, composites, alloys, etc.) can be patterned on the joined strands 130. In FIG. 13A, a polymer is patterned into the illustrated shape 214. The base strands 130 can be removed, or the polymer 214 can be positioned on top of the base strands. Likewise, multiple polymers 214 and 216 can be positioned on a base strand 130 of polymers. In alternate variations, the base polymer strands 130 can be removed such that the patterned polymer 214 or 216 can be positioned in the space left by the removed base strand 130. The finished assembly 130 can be fabri-cated into a tube construction for incorporation as a catheter or other medical device shaft.

FIGS. 14A to 14C illustrate another variation of con-structing a composite polymer tube 294 having a plurality of material sections under the present disclosure. As shown in FIG. 14A, the initial construction can comprise a conven-tional polymer tube 290 with one or more strands 292 wrapped about the tube 290. The tube 290 and strand 292 are then heat fused together to produce a composite polymer layer 294 where the strand 292 becomes at least partially embedded within the tube 290 such that the polymer layer 294 comprises a first material section comprising material 290 of the tube and a second material section comprising 292 of the strand. Clearly any number of variations of strands (as described above) can be embedded within the tube. Moreover, the outer diameter of the polymer layer 294 can include undulations. FIG. 14C illustrates the polymer tube 294 with a portion removed to highlight the cross-sectional area of the polymer layer. In an additional varia-tion, the construction of FIGS. 14A to 14C can replace the conventional polymer tube 290 with a composite polymer tube with varying material sections constructed as described herein.

Figures 15A, 15B:
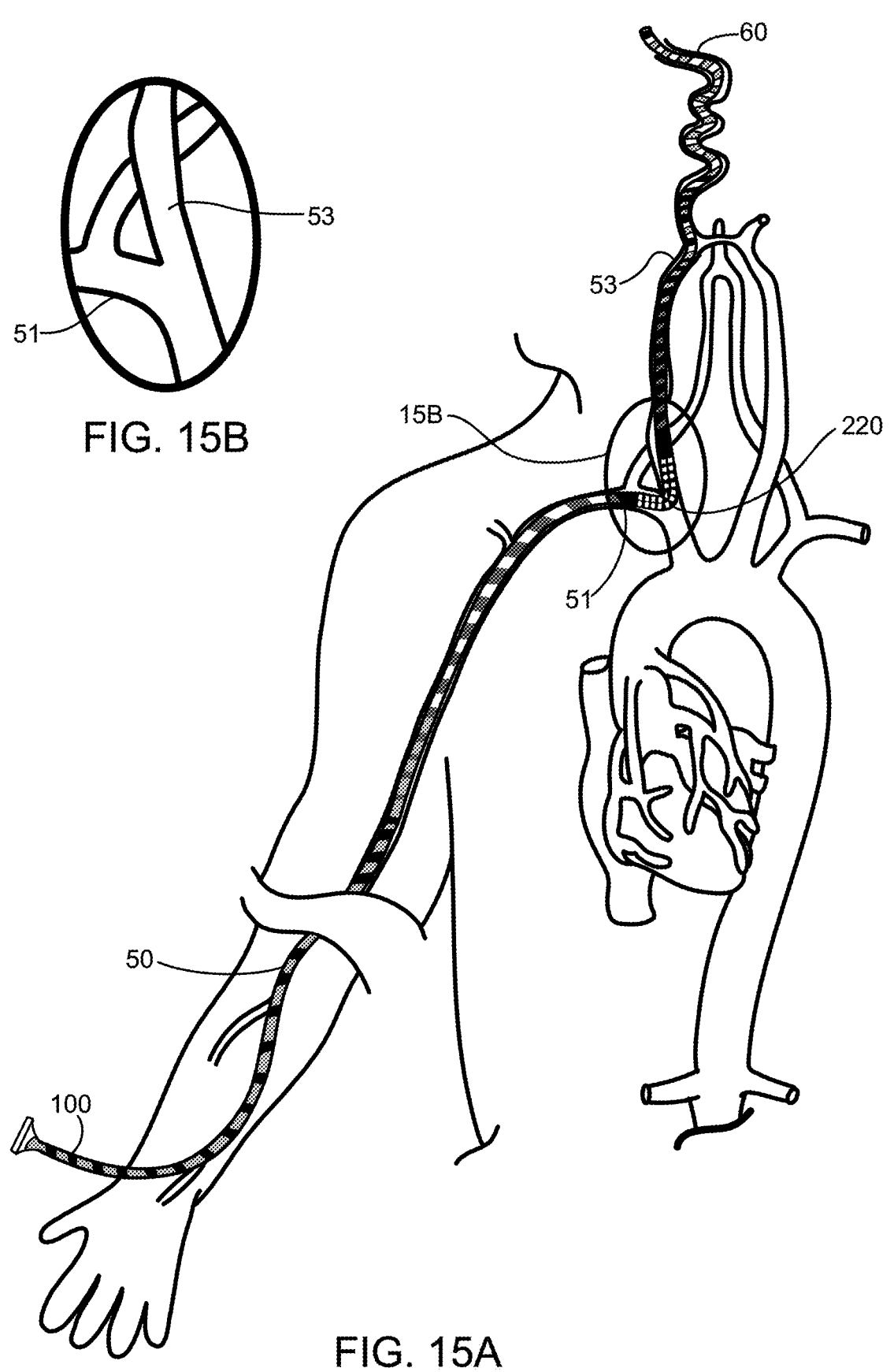
FIG. 15A illustrates a variation of a catheter having a hybrid region.
FIG. 15B shows a magnified view of the vessels in region 15B of FIG. 15A.

FIG. 15A illustrates a partial view of a patient's anatomy to demonstrate one feature of catheters 100 of the current disclosure. FIG. 15A illustrates the catheter 100 being inserted using a radial access procedure. Clearly, the catheter constructions described herein (as well as the polymer layers) can be incorporated in any device where selection of materials for specific performance characteristics is desired. Radial access procedures are becoming more of a desirable access point for interventional procedures. Radial access is the dominant mode for cardiac procedures and is becoming more commonplace for neurovascular procedures. However, the acute bends, particularly in trying to access the neurovascular, create considerable challenges for conventional catheters. The catheter constructions described herein are well suited to address the acute anatomical challenges faced by conventional catheters.

FIG. 15A illustrates a catheter 100 of the present disclosure advanced into a radial artery 50 and navigated to a right subclavian artery 51 and into an internal carotid artery 53 and ultimately to a neurovascular vessel 60. The catheter 100 shown in FIG. 15A includes regions of varying material sections, as discussed above. However, this variation of the catheter 100 includes a hybrid-region 220 that allows for multiple catheter performance characteristics at the region. Such a configuration not only allows for navigation through a tortuous bend but also does not suffer from the same drawbacks as a catheter simply constructed from a soft polymer. The present disclosures contemplate catheters having any number of hybrid-regions with any permutation of material characteristics. FIG. 15B illustrates the area from FIG. 15A and shows an acute bend between the right subclavian artery 51 and the right internal carotid artery 53. The catheter is removed from FIG. 15B for the purposes of illustrating the bend. Conventional catheters encounter problems when advanced through such acute bends because it is difficult for harder/firmer polymers to navigate through tortuous curving of the anatomy. Softer polymers are able to navigate such acute bends, but the softer section will not transmit adequate push forces and torque to the region of the catheter distal to the bend and soft polymer.

Figure 15C:
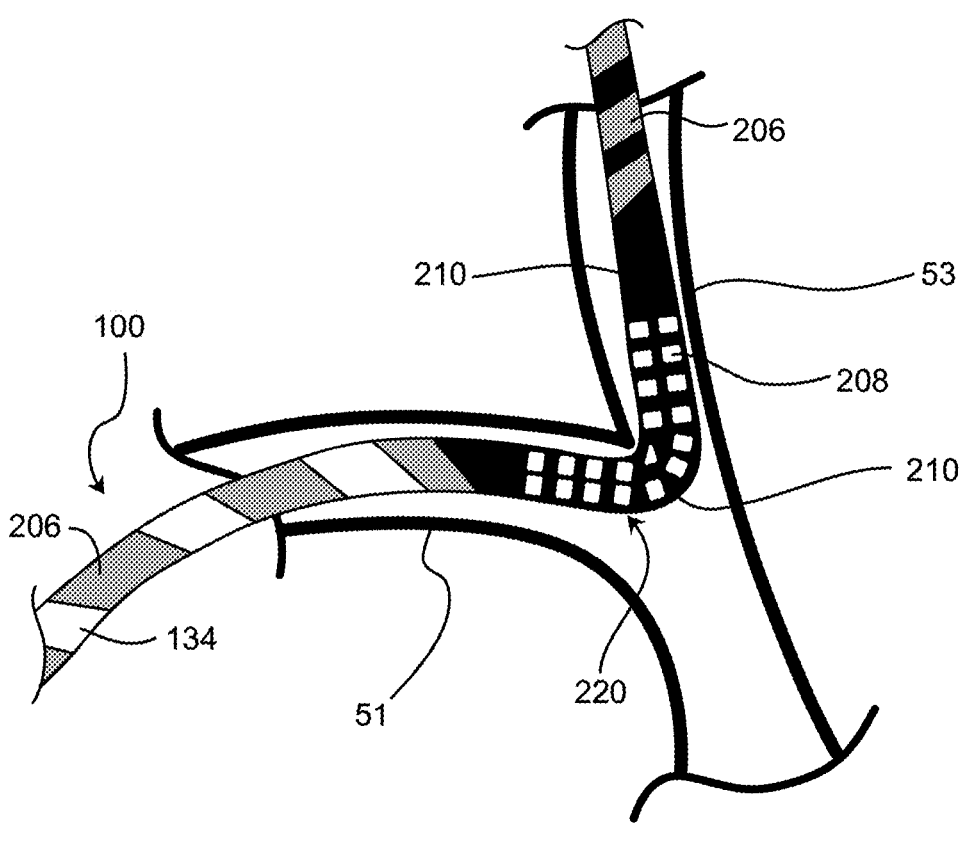
FIG. 15C illustrates a magnified view of the portion of the catheter in FIG. 15A that traverses an acute bend in arteries.

FIG. 15C illustrates a magnified view of a portion of catheter 100 that traverses the acute bend between the right subclavian 51 and the right internal carotid 53 arteries. The catheter 100 is designed such that the hybrid section 220 is positioned (or of a sufficient length) such that the hybrid section 220 is located within the bend when the distal end of the catheter 100 is at or near its intended target. FIG. 15C illustrates the catheter 100 as having multiple material sections 134, 206, etc. However, in this variation, the hybrid section 220 includes a material section 210 that is stiffer and allows for torque and force transmission of the catheter 100. The hybrid section 220 can also include one or more discrete sections of material 208 that provide a desirable material property that is different from the base material section 210. In this example, the discrete sections of material 208 comprise a flexible material. Such a construction allows the catheter to bend acutely because of the flexible discrete material sections 208. Meanwhile, the harder durometer base section 210 transmits pushing forces and torque to a distal region of the catheter.

Figure 15D:
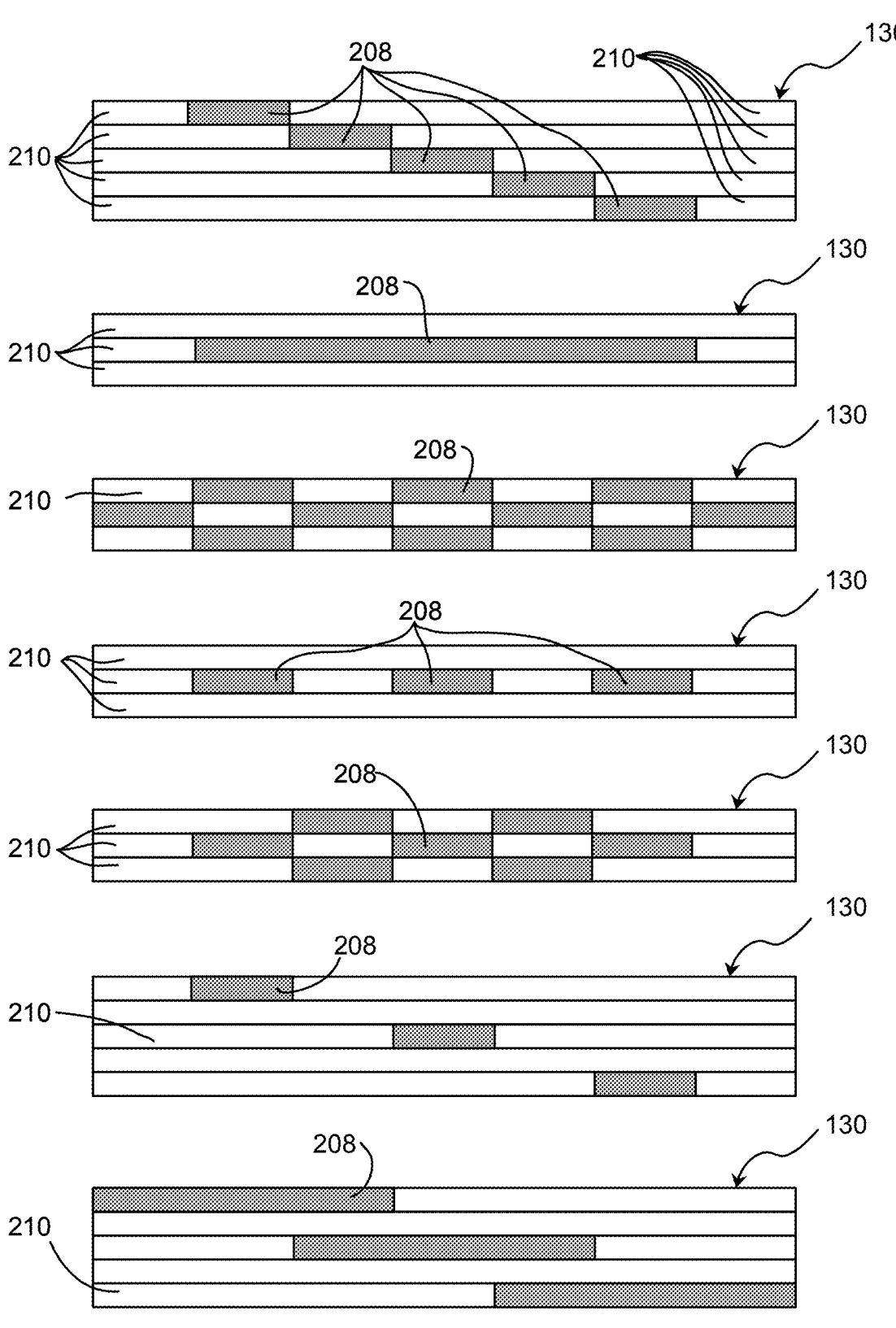
FIG. 15D shows a number of non-exhaustive design configurations to produce a hybrid region, as shown in FIGS. 15A and 15C.

FIG. 15D shows a number of non-exhaustive design configurations to produce a hybrid region as shown in FIGS. 15A and 15C. The hybrid region of the catheter/finished tube is formed from a plurality of materials 130 joined together where a base material 210 is interrupted by a discrete section of a second material 208 having different properties than the base. For example, in one variation of the design, materials 210 can comprise a stiffer/harder durometer material or polymer while materials 208 comprise flexible/soft material or polymer. Clearly, any material properties other than hard/soft materials can be selected and configured into a hybrid region.

Figures 16A, 16B:
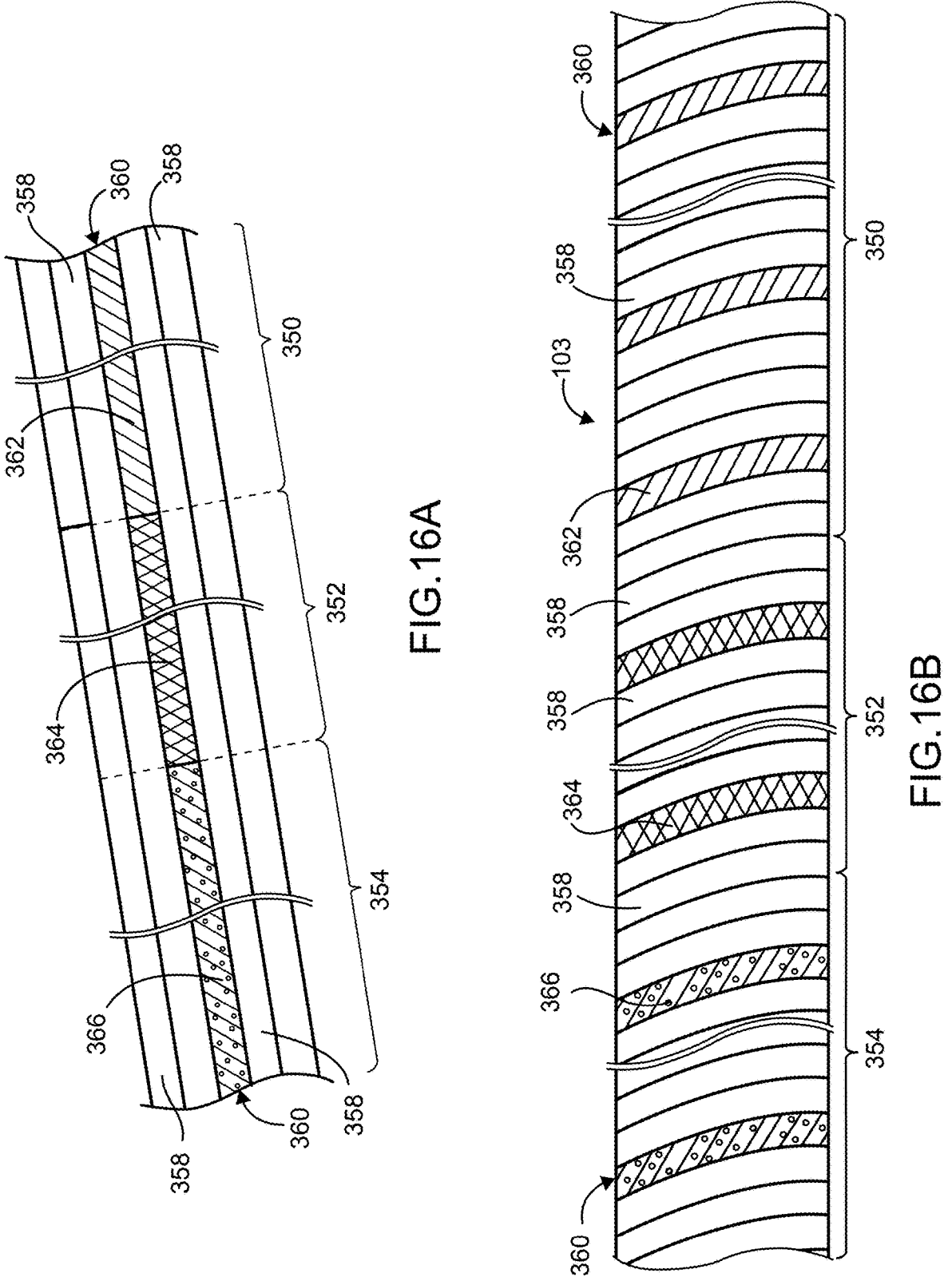
FIGS. 16A to 16F illustrate additional examples of various constructions of tube members for use with the devices described herein.

FIGS. 16A and 16B illustrate an additional example of a construction of a tube 103 for use with the devices described herein. FIG. 16A is a sectional view of a number of strands 358, 362, 364, 366 that are joined to form a tubular section as depicted in FIG. 16B. In FIG. 16B, the tubular section 103 includes a plurality of material sections that extend in a continuous spiral over the tube section 103, where one material section 360 that extends from region 350 through regions 352 and 354 changes materials at each region. In one example, the material section 360 comprises a reinforcement material section as it continuously and spirally extends over multiple regions. In addition, the structural properties of each region can be selectively engineered based the individual materials 362, 364, and 366. For example, to increase flexibility from a proximal to distal direction of a device, the first region 350 can comprise a material 362 having a hardness/durometer that is greater than material 364 in adjacent/second region 352.

In additional variations, the third region 354 can comprise a material 366 having a durometer/hardness that is less than a hardness/durometer material 364. It is noted that material sections adjacent to material section 360 (e.g., 358) can include any number of materials as discussed herein. However, in some variations of the devices described herein, material section 360 comprises a hardness/durometer that is greater than a hardness/durometer of each adjacent material section 358 in the respective region. For example, in first region 350, material section 360 can comprise a material 362 that has a durometer/hardness greater than the material of each adjacent materials section 358 in that same region (i.e., region 350).

Similarly, in additional variations, this construction can be repeated in regions 352 and 354, where material 364 comprises a greater durometer than the materials in the adjacent material sections within that region, and material 366 comprises a greater durometer than the materials in the adjacent material sections within that region. In such an example, material section 360 can effectively function as a continuous torque coil within the tube member 130 (at least across any two sections) but can have a hardness/durometer that changes or is gradually decreased as required by the application. In those situations that require a catheter to reach distal regions, the catheter can be constructed via the tubular member 103 to have increasing flexibility towards a distal region while still employing a continuous torque coil that also decreases in flexibility.

In yet an additional variation, the constructions shown in FIGS. 16A and 16B can comprise configurations where material section 360 comprises a durometer/hardness that is lower than the adjacent material sections 358 and/or decreases in each region (350, 352, 354).

Figures 16C, 16D:
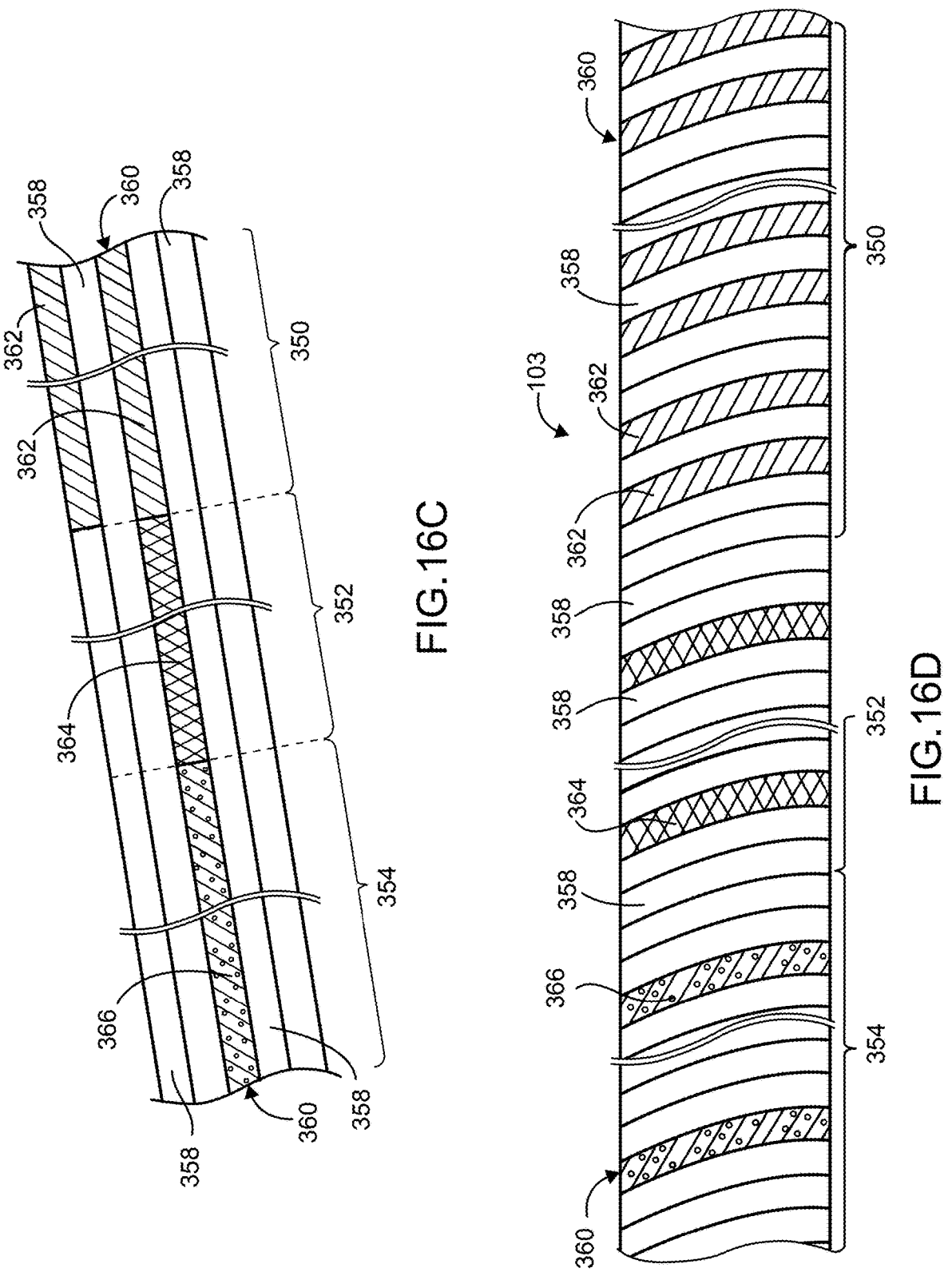

FIGS. 16C and 16D illustrate another example of a construction of a tube 103 for use with the devices described herein. FIG. 16C shows a sectional view of a number of strands 358, 362, 364, 366 that are joined to form a tubular section as depicted in FIG. 16D. However, the area that forms region 350 includes two sections of material 362 having the same durometer/hardness. This construction is shown in FIG. 16D, where the tubular section 103 includes a plurality of material sections that extend in a continuous spiral over the tube section 103 where one material section 360 that extends from region 350, through regions 352 and 354 changes materials at each region, while region 350 includes two spirally wound materials 362 having the same durometer/hardness. In such a configuration, first region 350, material section 360 comprises a material 362 that has a durometer/hardness different than the material of each adjacent materials section 358 in that same region (i.e., region 350) but equal to another material section material 362. As noted above, the durometer/hardness of material 362 can be greater or less than the adjacent sections.

Figures 16E, 16F:
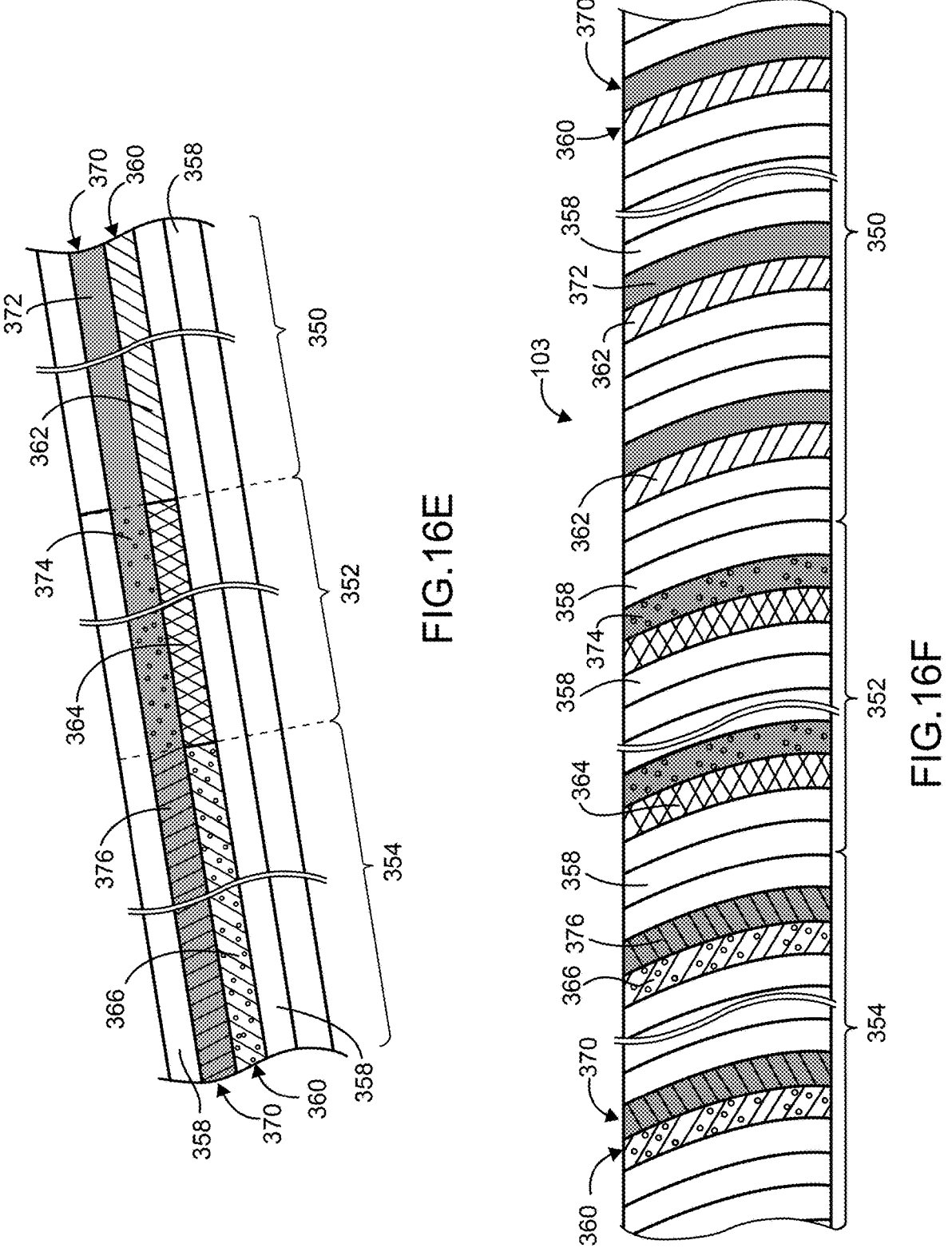

FIGS. 16E and 16F show another potential example of a construction of a tube 103 for use with the devices described herein. FIG. 16E illustrates a sectional view of a number of strands 358, 362, 364, 366 that are joined to form a tubular section as depicted in FIGS. 16A and 16B above, with an additional material section 370 that contains materials 372, 374, and 376 in respective sections 350, 352, and 354. FIG. 16E shows the tubular section 103 formed from the configuration of FIG. 16E where the plurality of material sections that extend in a continuous spiral over the tube section 103 and one material section 360 serves as a reinforcement material section, where the hardness/durometer of materials 362, 364, 366 in that material section extends across regions 350, through regions 352 and 354 and changes materials at each region. However, the construction shown in FIGS. 16E and 16F also show a material section 370 having materials 372, 374, and 376 that are lower than or equal to the hardness/durometers of adjacent materials in material sections 358. In additional variations, the hardness/durometers of materials 372, 374, and 376 can decrease respectively in sections 350, 352, and 354. While material section 360 is shown to be directly spirally adjacent to material section 370, additional variations include spacing of the highest and lowest durometer materials as opposed to being directly adjacent.

Figure 17A:
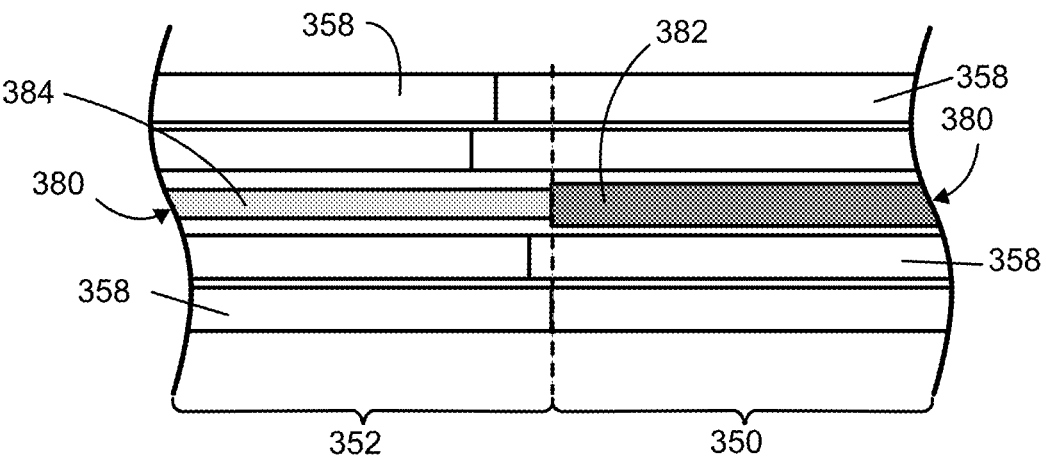
FIGS. 17A and 17B illustrate another example of customizing material sections using a transition material section that reduces in width.
Figure 17B:
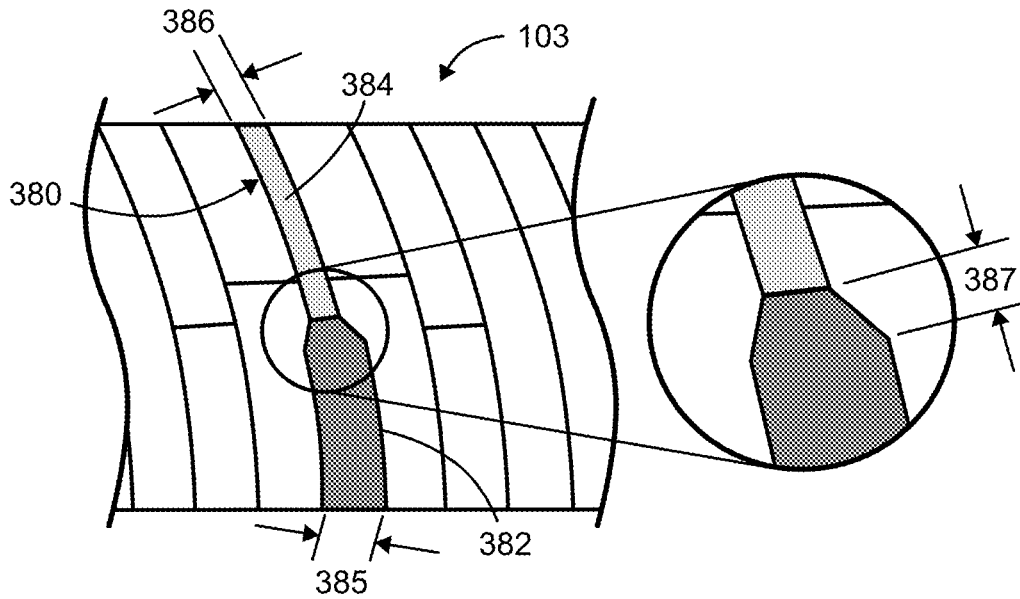

FIGS. 17A and 17B illustrate another example of customizing material sections to adjust the structural characteristics of a tube member 103 and/or device as described above. FIG. 17A illustrates a series of material sections 358 adjacent to a transition material section 380. As noted above, material section 358 can comprise any variety of materials that are desired for adjusting the characteristics of the device. FIGS. 17A and 17B illustrate a transition material section 380, which includes a first width 385 corresponding to a width of the transition region 380 in the first region 350. The transition material section includes a second width 386 corresponding to a width of the transition region 380 in the second region. As discussed herein, not only can the widths vary but the height/depth of the material can be changed. Moreover, FIG. 17B illustrates that material section 380 initially comprises a first material 382 and then transitions to a second material 384, however, in additional variations the material section can comprise a single material that changes from a first width 385 to a second width 386. Additional variations of the design can include a transition region that changes from a smaller dimension to a larger dimension in a distal direction along the tubing.

As discussed above, FIG. 17A illustrates the state of the tubular portion prior to the material sections being joined in a spiral configuration. Once joined into a tubular structure 103, as shown in FIG. 17B, the materials on either side of the thinner region of the transition material section 380 fill in to form a completely sealed joint between adjacent material sections. As shown, the first region 350 can include a section where a width of the transition material section is consistent and, at the start of the second region 352, the transition material section 380 steps down at a stepdown region 387. Variations of this configuration include a length of the stepdown region 387 being less than the width of the larger transition material section. In another variation of this configuration, the transition material section 380 can include a first material 382 in the first region 350 and a second material 384 in the second region 352. As described above, the transition material section 380 can comprise materials to permit the section 380 to function as a torque coil, e.g., where the hardness/durometer of the transition section is greater than adjacent material sections. Alternatively, the transition material section can comprise a hardness/durometer that is less than adjacent material sections. In even further variations, a single tubular structure 103 can include multiple step-down regions for different material sections. Alternatively, or in combination, section 380, or any material that has a greater hardness/durometer than an adjacent material, functions as a type of "push coil" where this increased hardness/durometer material is helically formed in the catheter tubing and reinforces the tubing when pushed from a proximal location.

Figure 18A:
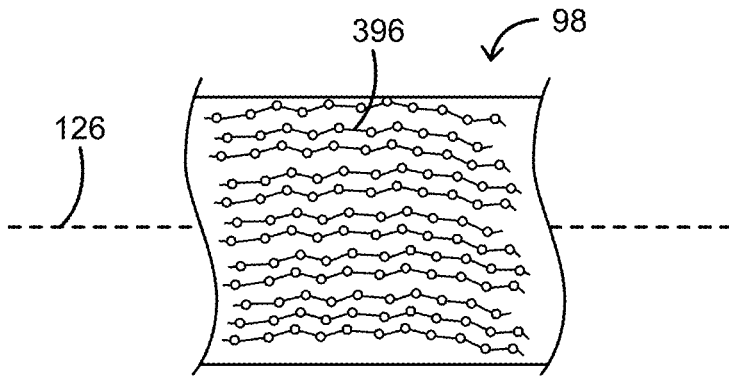
FIG. 18A shows a traditional catheter construction where the polymer chains are aligned with an axis or axial length of the tube.
Figure 18B:
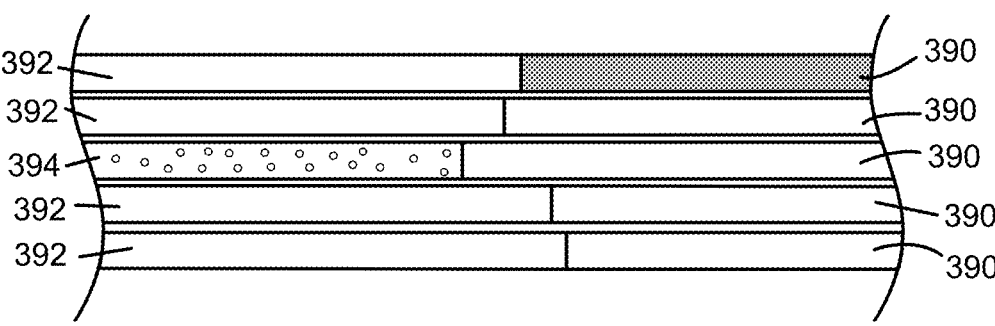
FIGS. 18B to 18E illustrate additional design variations for use in composite tubing sections having a high modulus of elasticity/stiffness.
Figure 18C:
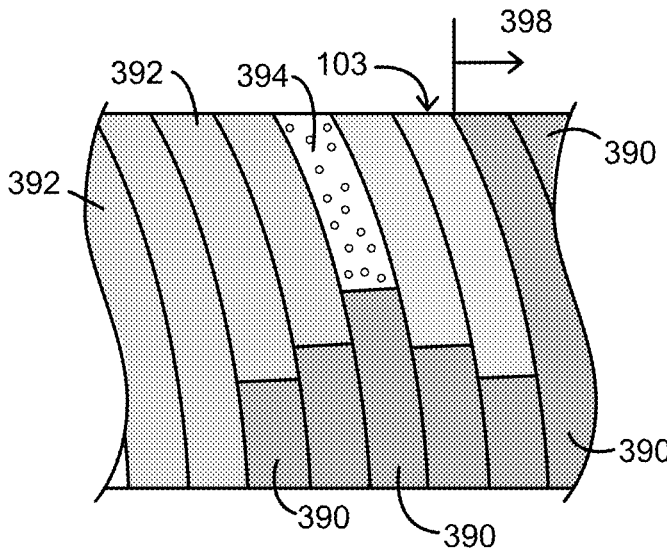
Figure 18D:
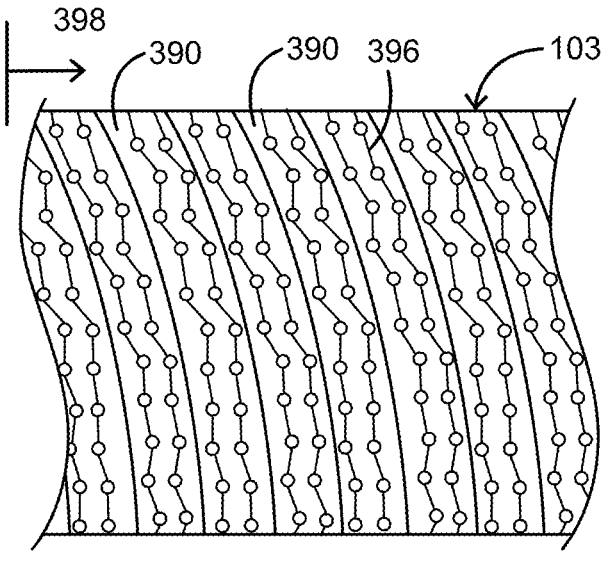
Figure 18E:
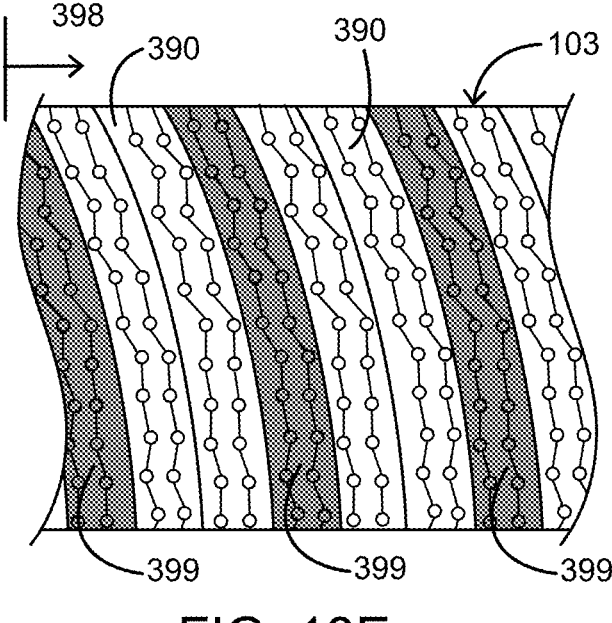

FIGS. 18B to 18E illustrate another design variation for use in composite tubing sections. In a traditional catheter construction, as shown in FIG. 18A, the use of an extruded material 98 aligns the polymer chains 396 along an axial length of the tube in alignment with an axis 126 of the material 98. Therefore, flexure of a conventional stiff tube causes bending in a normal direction against a backbone of the polymer chain 396. Excessive bending can lead to fracture of the polymer 98. One benefit of constructing tube 103 from one or more polymers that have a high elastic modulus/stiffness is that the polymer chains 396 are oriented in a spiral direction about the tube structure 103. For example, in the variations as shown in FIGS. 18C to and 18E, the polymer chains 396 extend in a helical pattern, which allows increased flexure of the polymer and reduce the risk of fracture of the material due to bending of the tube structure 103. FIG. 18B illustrates one example of a plurality of material sections where material 390 is joined to materials 392 and 394. These materials are sealingly joined to form tube structure 103 of FIG. 18C, where the material sections extend spirally along an axial length of the tube structure 103 to form a wall that can optionally be incorporated into one of the devices described herein. In this variation, the material sections in a first region (designated in the direction shown by arrow 398) are formed from a first polymer 390 such that a polymer chain extends spirally in that region following the spiral of the material section as it is wrapped to form the tube 103, as shown in FIG. 18D. Having a construction as shown in FIG. 18C, where in the first region, the plurality of material sections comprises a first polymer 390 that has a high modulus/stiffness adjacent to a second region where each of the polymers 392, 394 comprise a lower modulus/stiffness than material 390 allows a device design with a proximal region that is stiff but more resistant to fracture. FIG. 18E shows another variation of a construction 103 where the first region 398 formed from one or more material sections extending spirally and comprising a single polymer 390 with a similar polymer 399 having the same structural properties as the first polymer 390 but is distinguishable/identifiable from the first polymer 390 (e.g., via color, surface texture, markers, radiographic, etc.). In such a construction, the material properties of section 398 are the same, but the tubular structure 103 can be uniquely identified by the distinguishable pattern either visually and/or mechanically) resulting from materials 390 and 399 so that a caregiver can identify the tubing relative to other tubing. For example, when used in a catheter positioned in a patient via a femoral or radial artery, the caregiver is able to distinguish the catheter having the features shown in FIG. 18E relative to other catheters when region 398 extends from the patient's body. It is understood that section 398 will comprise at least two distinguishable material sections, 390, 399 having similar or the same structural properties, while the remaining region of the catheter (e.g., as shown in FIG. 18C) could have additional material sections as discussed herein. Alternatively, the remainder of the catheter could also have a conventional extruded construction.

Figure 19A:
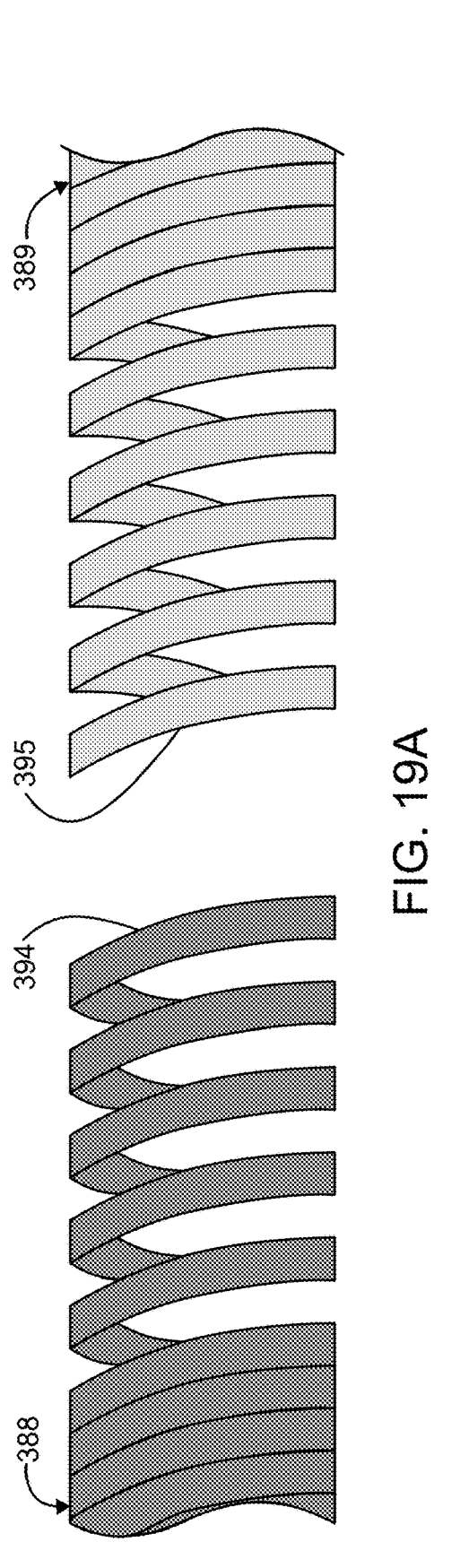
FIGS. 19A to 19D illustrate another variation of a composite tube.
Figure 19B:
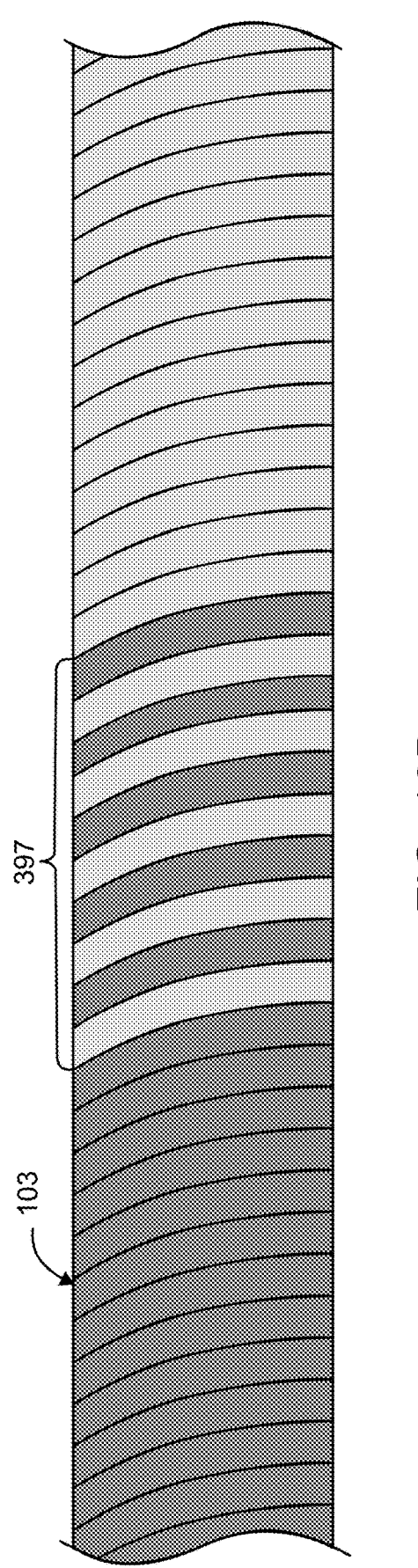
Figure 19C:
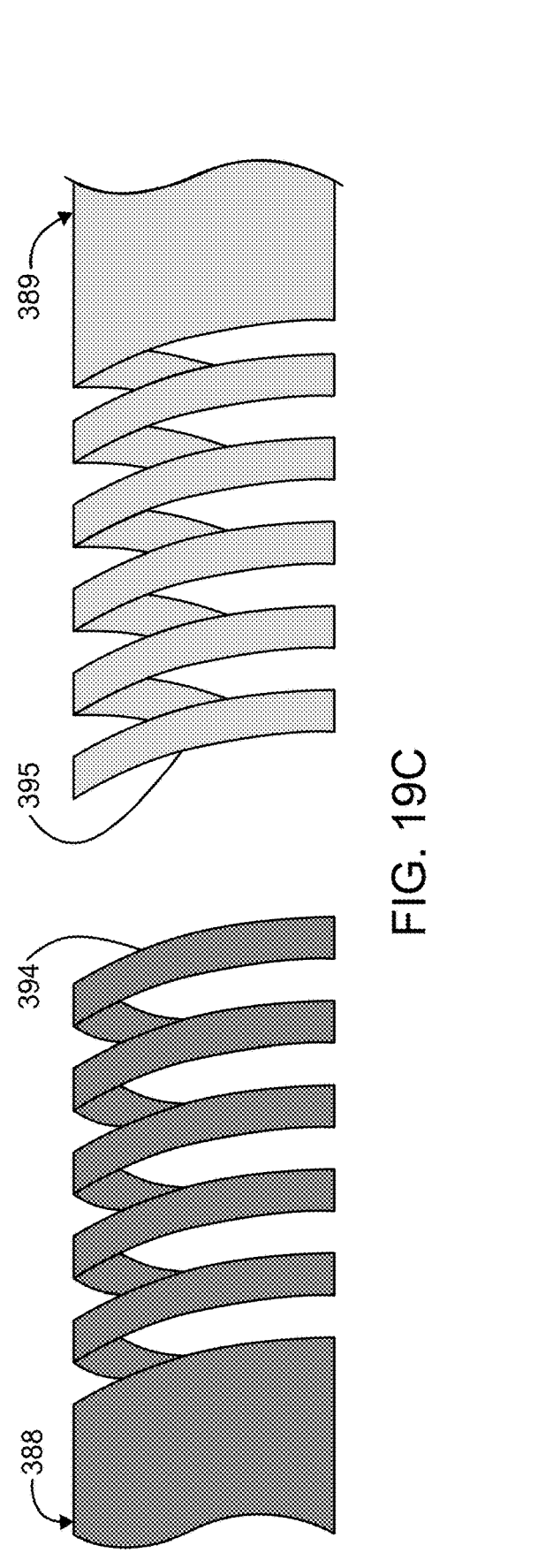
Figure 19D:
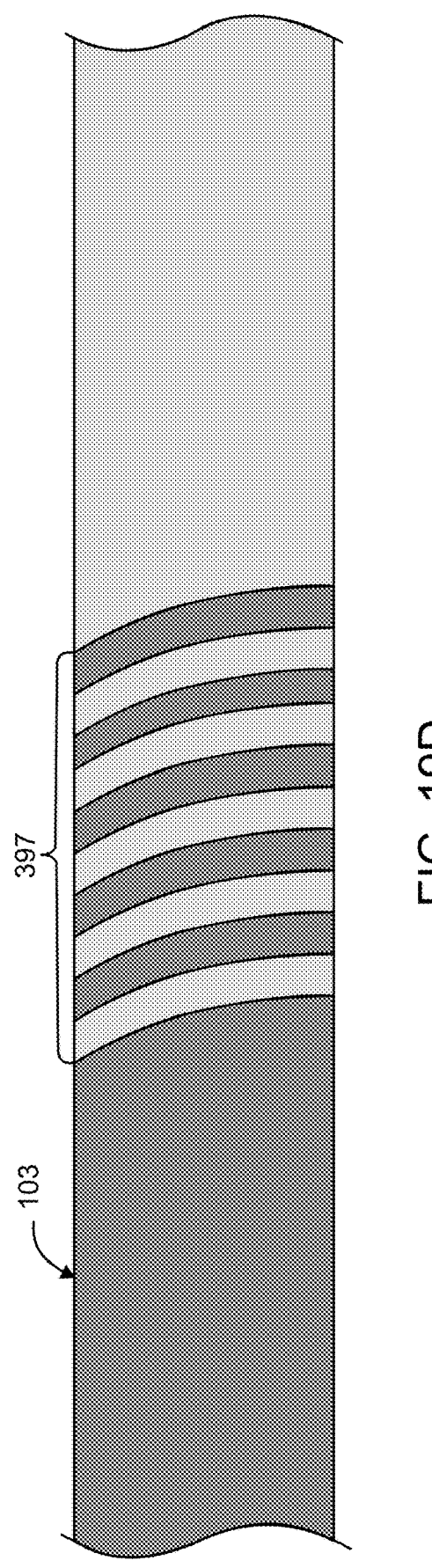

FIGS. 19A to 19D illustrate another variation of a composite tube 103 for use in the devices described herein. In this variation, FIG. 19A shows a first material tube 388 that can be conventionally extruded as a common single lumen tubing. As shown, the tube 388 is separately spaced from a second conventionally formed material tube 389. Each material tube 388, 389 can have separate properties as discussed above. In addition, the tubes 388, 389 can be respectively cut (e.g., via laser cutting) to create a spiral or other helical pattern 394, 395. FIG. 19B illustrates the tubes 388 and 389 of FIG. 19A sealingly joined together such that the different properties of each material section provide a transition section 397 similar to those discussed above. FIG. 19C illustrates a variation where a first material tube 388 and second material tube 389 are continuous and then cut to form a helical patterns 394, 395 that are ultimately joined to form transition section 397 as shown in FIG. 19D.

The ability to incorporate softer materials with a relatively harder material, as shown in the above figures allow for improved custom selection of device properties. Moreover, the ability to transition continuously spiral material sections into different materials as well as controllably stepping down in width allows for a drastic improvement in catheter design. The ability to change materials as described herein provide manufacturers with the ability to change a greater number of catheter design elements to fine tune catheter construction to a degree that was previously unavailable with conventional catheter construction.

Figure 20A:
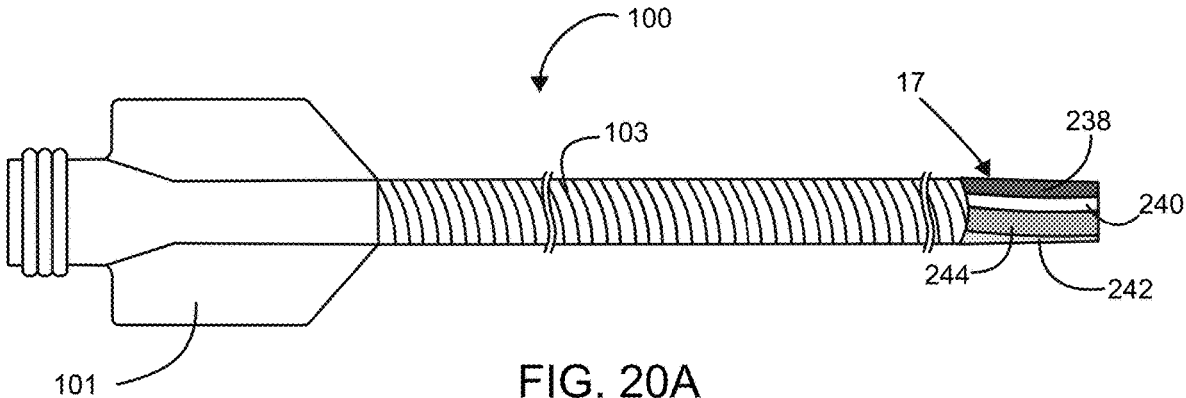
FIG. 20A illustrates another aspect of an improved catheter incorporating a composite layer at a tip of the catheter.

FIG. 20A illustrates another aspect of an improved catheter 100 incorporating a composite layer at a tip 17 of the catheter. As shown, catheter 100 can include any number of material sections 238, 240, 244, and 242 to form a directional tip 17 that is located at a distal end of the catheter body 103. Variations of a catheter 10 with a directional tip 17 can include a catheter body having a composite structure as discussed above. Alternatively, the catheter body can comprise a conventional catheter construction with a directional composite tip 17.

Figure 20B:
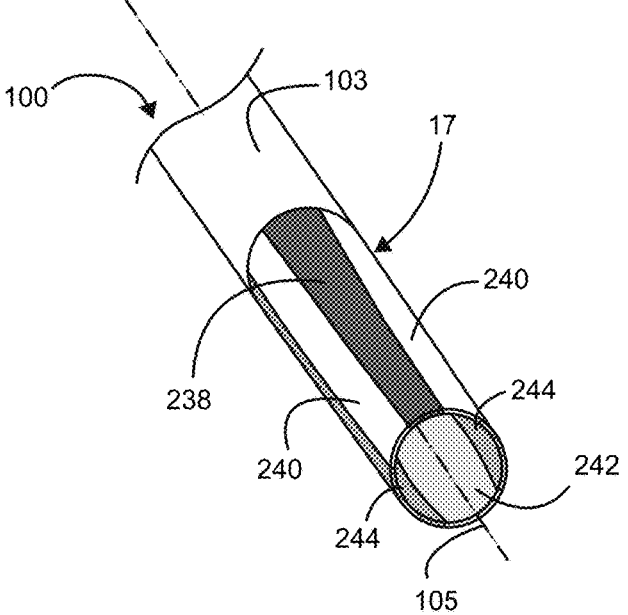
FIG. 20B illustrates a directional tip at a distal end of the catheter body.

FIG. 20B illustrates a directional tip 17 at a distal end of the catheter body 103. As shown the material sections 238, 240, 244, and 242 can comprise polymers of varying durometer, thickness, widths, etc. In addition, the material sections 238, 240, 244, and 242 can be spirally wound about the tip 17 or can extend parallel to an axis 105 of the catheter 100 as shown.

Figure 20C:
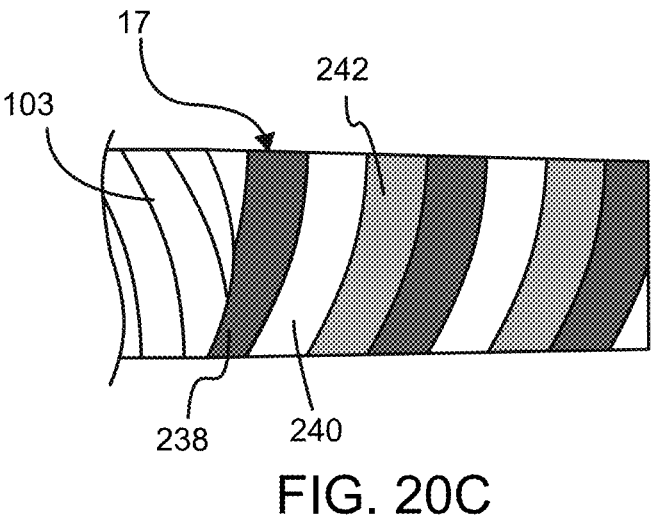
FIGS. 20C and 20D illustrate another variation of a directional tip located at a distal end of a catheter body.
Figure 20D:
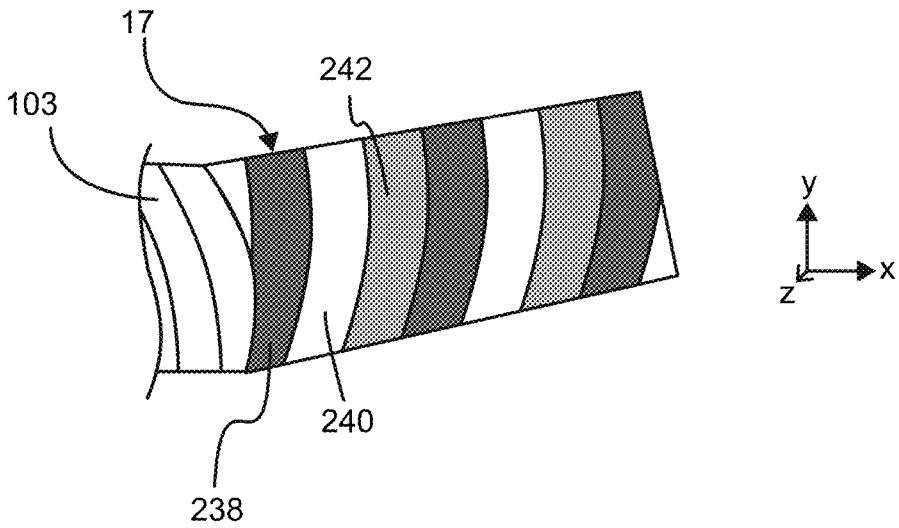

FIGS. 20C and 20D illustrate a variation of a directional tip 17 located at a distal end of a catheter body 103. In this variation, the material sections 238, 240, and 242 extend helically or spirally to form the tip 17. Moreover, as shown in FIG. 20D, the material sections can be designed to preferentially bend towards a particular direction when encountering resistance, such as a vessel wall. In the illustration shown in FIG. 20C, the directional tip 17 bends in the "y" direction. The directional tip 17 uses a combination of materials and material dimensions to control the preferential bend. It is noted that variations of directional tip 17 can bend in multiple directions but will be biased to bend towards the preferential direction. Moreover, the preferential bend direction of the directional tip 17 can occur in multiple directions in three-dimensional space and not just towards a single axis as depicted.

Figure 21A:
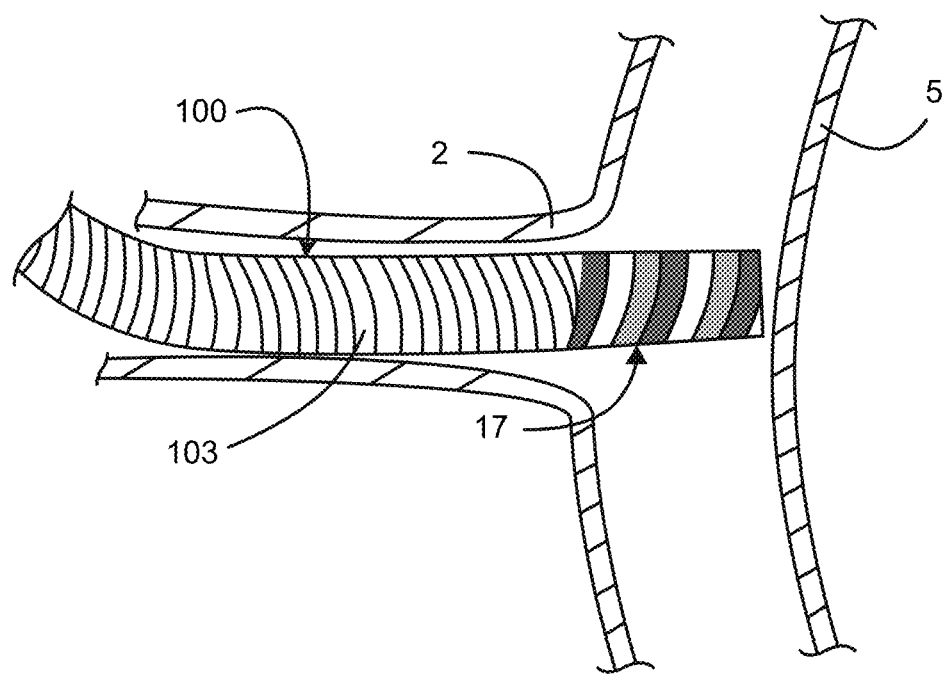
FIGS. 21A and 21B show another example of a catheter with a directional tip.
Figure 21B:
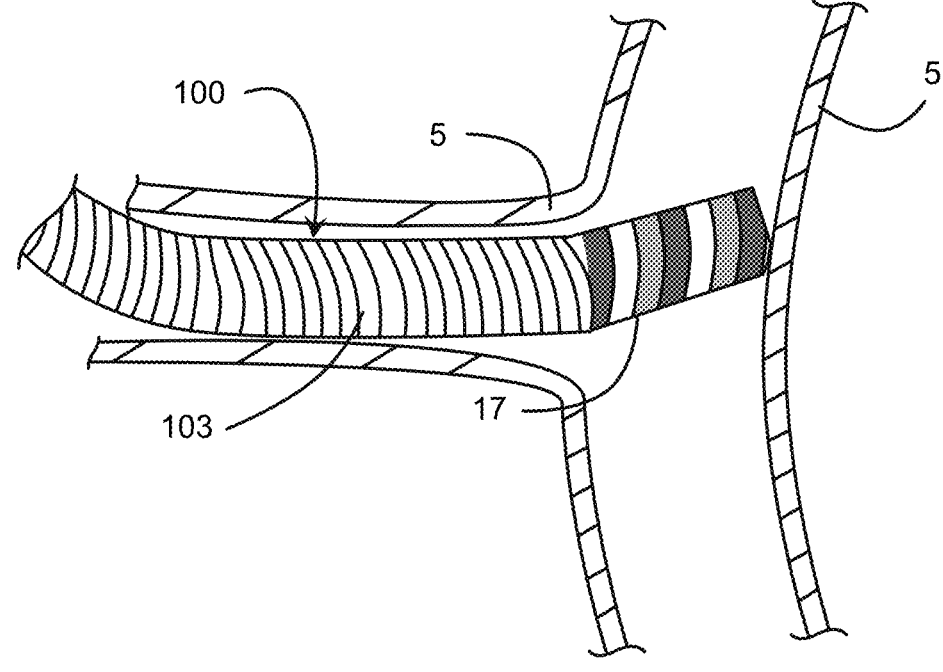

FIGS. 21A and 21B show an example of a catheter 100 with a directional tip 17. FIG. 21A illustrates the catheter 100 advanced through a vessel 2 into a branching vessel 5. As the catheter approaches a far wall of the branching vessel 5, an end of the directional tip 17 engages a wall and deflects towards a preferential direction in FIG. 21B. It is noted that FIG. 21B illustrates the tip member 17 deflected upwards. Many conventional catheters rely on a soft distal tip to minimize the risk of causing trauma to a vessel, freeing plaque from a vessel wall, puncturing a vessel, or creating embolisms in the bloodstream. When the square/flat tip of conventional catheters engages the back wall of the branching vessel it can often get caught since it is not designed to deflect in a preferential direction. Having a directional tip 17 that bends in a preferential direction reduces the chances that the directional tip 17 becomes caught against a branching vessel wall.

Figure 22A:
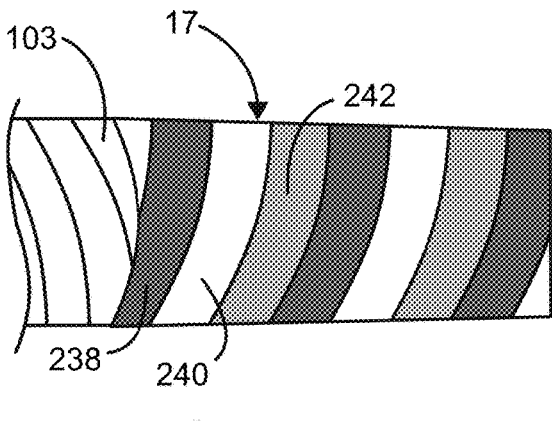
FIGS. 22A to 22D illustrate various configurations of material sections forming directional tips at the end of the catheter body.
Figure 22B:
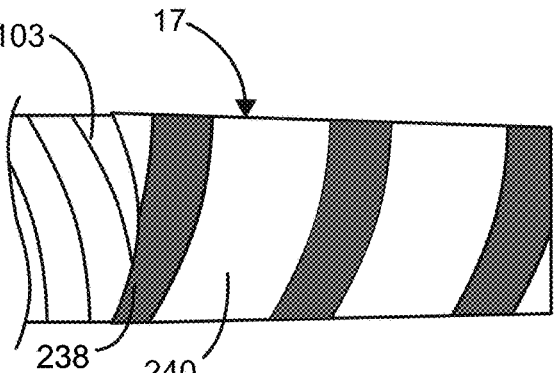
Figure 22C:
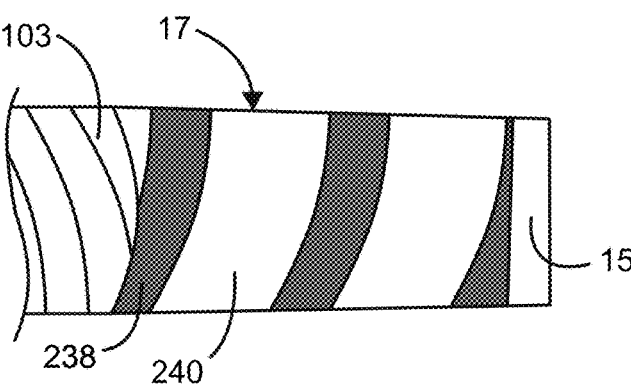
Figure 22D:
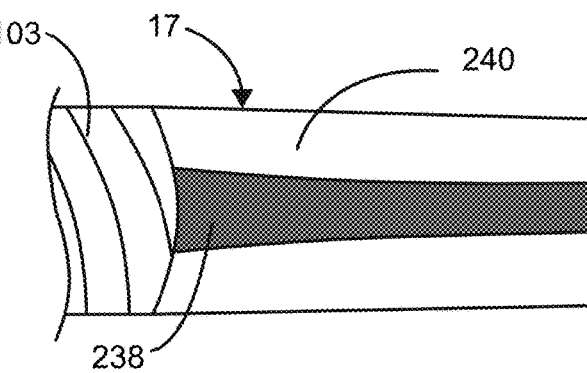

FIGS. 22A to 22D illustrate various configurations of material sections 238, 240, 242 forming the directional tip 17 at the end of the catheter body 103. FIG. 22A illustrates a number of spirally wrapped material sections 238, 240, 242. FIGS. 22B and 22C illustrate two material sections 238 and 240 having different widths where FIG. 22C shows a directional tip 17 with a traditional soft tip 15 at an end. FIG. 22D illustrates material sections 238 and 240 extending parallel to the axis of the tip 17. As with conventional soft tips, the directional tip 17 will ordinarily comprise soft polymers with various reinforcement or other designs to permit preferential bending.

Figures 23A, 23B:
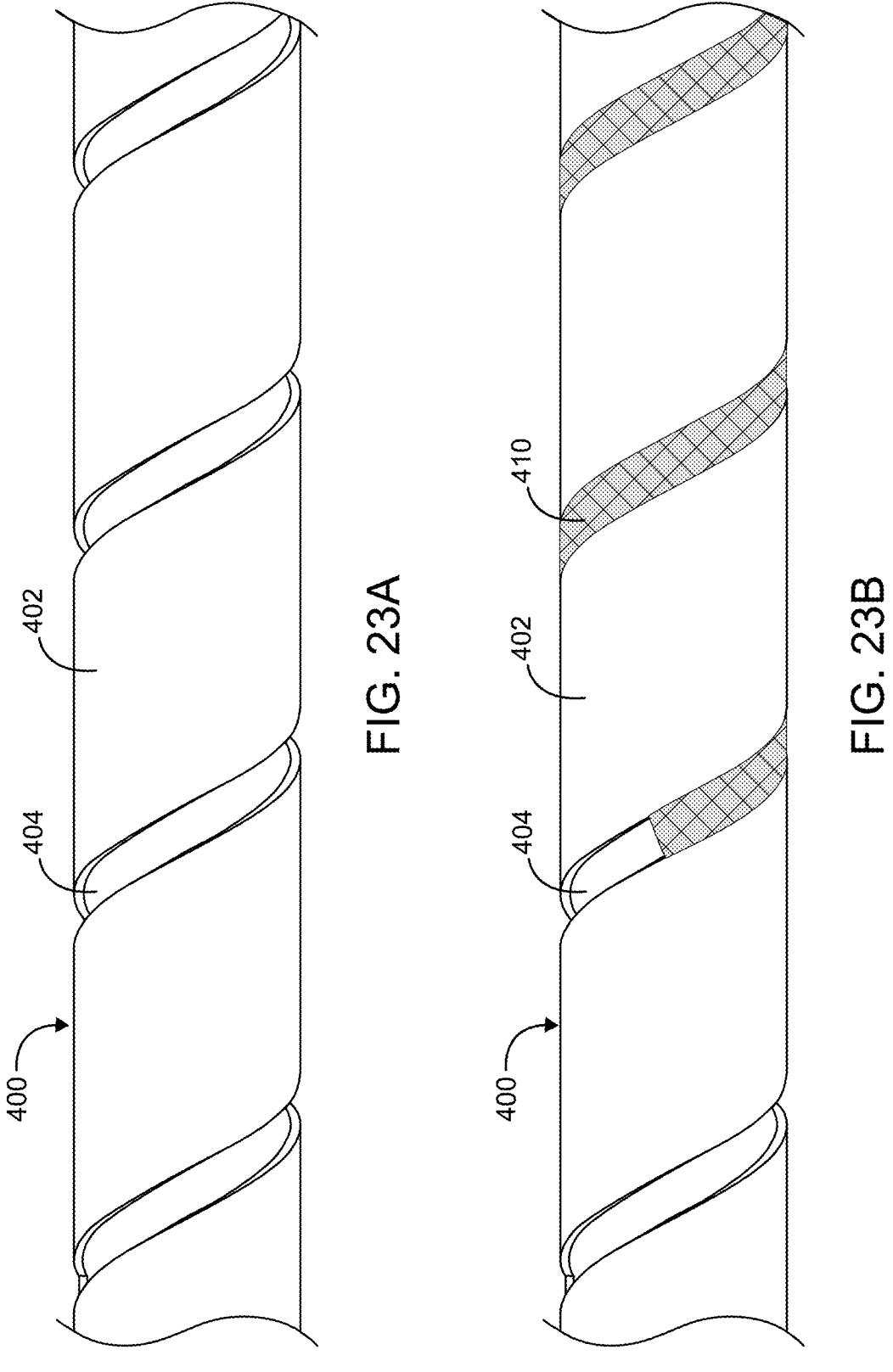

FIG. 23A to 23F illustrates another variation of fabrication of a composite tube. As shown, in FIG. 23A, a tube 400 can be formed from a base material 400 (e.g., by extrusion, 3D printing, or any other fabrication process). The tube 400 can be altered or formed to have spiral grooves (that extend through the wall) or slots (i.e., cuts that do not extend through the entirety of the wall). Next, as shown in FIG. 23B, a material such as a polymer or other material, is joined to the tube material 402 within the groove 404 to form a material section 410 that extends within the tube 400. FIG. 23C shows a second material forming a second material section 412 that is positioned within the groove and joined to an end of the first material section 410. Accordingly, FIG. 23C shows a tube structure 400 having three different materials 402, 410, and 412.

Figure 23F:
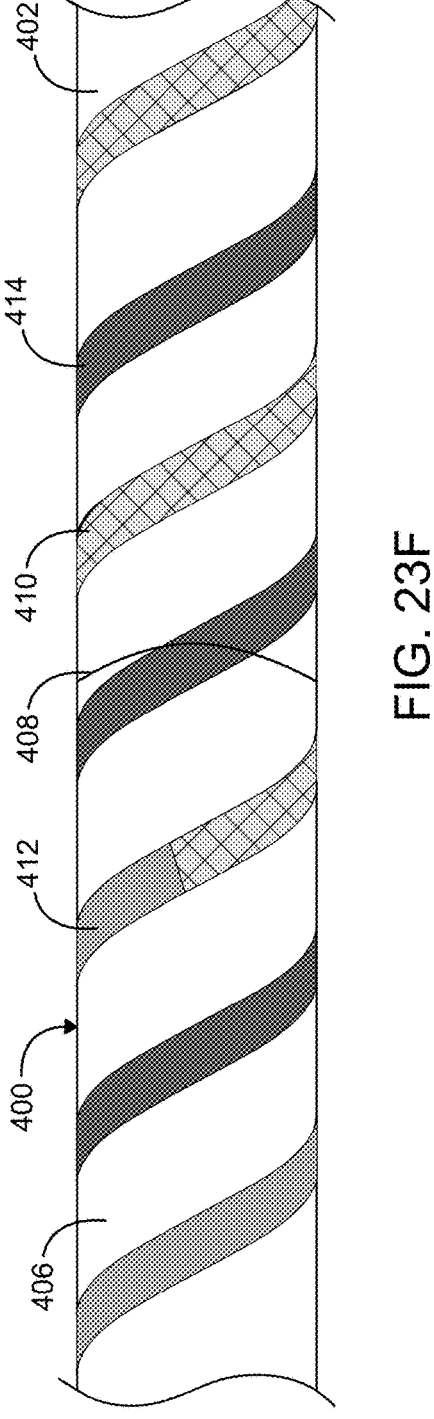

FIG. 23D shows a variation similar to that shown above, but where material sections 410 and 412 are adjacent to a different material section 414. FIG. 23E illustrates two joined material sections 410 and 412 with a material section that is spaced apart 414. FIG. 23F shows another variation where the tube structure 400 can be formed from a plurality of tubes having different materials 402, 406 with different structural properties or different distinguishable properties. In such a case, a tube comprising material 402 can be joined to a tube comprising material 406 at a juncture 408 and the composite tube 400 can be altered as discussed above in FIG. 23A.

Figure 24:
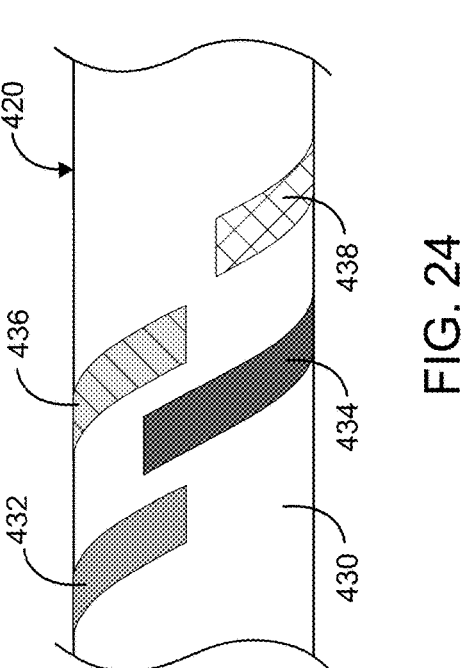
FIG. 24 illustrates another variation of a composite tube that is formed with non-overlapping material sections.

FIG. 24 illustrates another variation of a composite tube 420 that is formed with non-overlapping material sections 432, 434, 436, 438 such that the material or polymer of the tube 430 separates the material sections. As shown, the material sections can be axially spaced (e.g., 434 is axially spaced from 432 and 436). Furthermore, the ends of the material sections can overlap (e.g., 434, 432, 436) or the ends can be spaced as well (e.g., 438). The construction 420 shown in FIG. 24 can be fabricated by entirely by the use of material sections where material 430 is wound with the remaining material sections. Alternatively, the composite tube 420 can comprise a polymeric (formed from an extrusion) or other tube comprising material 430 and mechanically altered with slots or grooves to allow for insertion of the material sections 432, 434, 436, 438.

Figure 25:
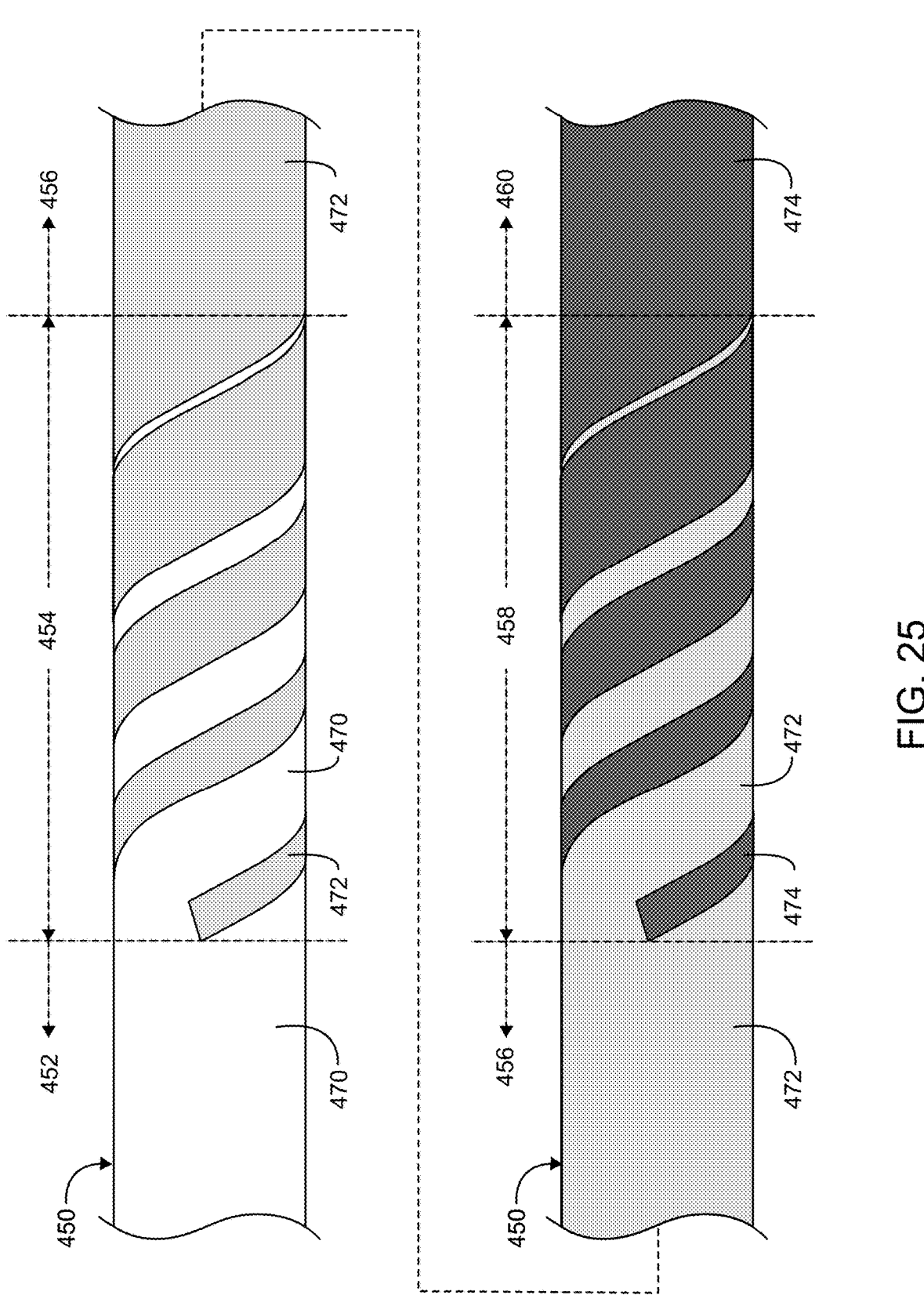
FIG. 25 illustrates another variation of a composite tubing.

FIG. 25 illustrates another variation of a composite tubing 450 that can be formed using any process described herein or used in manufacturing of tubing. FIG. 25 illustrates the tubing 450 having a first region that comprises a single material 470, where the first region 452 is adjacent to a second region 454 where a material section 472 comprising a second material begins in a spiral pattern. In the second region 452 the first material forms a first material section 470 that decreases in a width (as measured axially) while the second material section 472 increases in width until a third region 456 that is fully formed from the second material 472. The composite tubing continues to a fourth region 458 where a third material section 474 causes formation of material section 472, which decreases in width as the third material section 474 increases in width. As discussed herein, each material 470, 472, 474 will have different properties (e.g., different structural properties and/or visually distinguishable properties) allowing for the overall property of the composite tube 450 to be customized. FIG. 25 also shows that the third material 474 continues in a fifth region 460 that is entirely formed from the third material 474. It is noted that the widths, spacing, and spiral wind of the material sections shown in FIG. 25 are for illustrative purposes only and can be combined with any variation discussed herein. In addition, in regions 452, 456, and/or 460 in the composite tube 450 can be formed from extruded tubes, which are mechanically altered in the second region 454 and fourth region 458. Alternatively, regions 452, 456, and/or 460 can be spirally wound.

It is noted that the polymer strands disclosed herein can extend in a helical manner about the inner braid/coil or support structure. In additional variation, the polymer strands can be aligned in a lengthwise manner with an axis of the catheter and wrapped about the support structure to form a catheter section. Any number of manufacturing practices can be used to produce the catheter constructions of the present disclosure. For example, the strands can be directly wrapped on a liner/braid construction and then fused together to form a catheter construction; 2) the strands can be wrapped over a tube and fused, then transferred to the remaining components to produce a catheter construction; and/or 3) the strands can be produced as a flat construction (either fused together, extruded, molded, or otherwise formed) and then ribbon assembly wrapped and fused onto a liner/braid. The devices described herein can also be constructed using a 3-d printing process.

It is understood that any manufacturing process is within the scope of this disclosure and should not be limiting upon any claimed structure to any claims relating to composite polymer tubes or catheter constructions.

As for other details of the present invention, materials and manufacturing techniques may be employed as within the level of those with skill in the relevant art. The same may hold true with respect to method-based aspects of the invention in terms of additional acts that are commonly or logically employed. In addition, though the invention has been described in reference to several examples, optionally incorporating various features, the invention is not to be limited to that which is described or indicated as contemplated with respect to each variation of the invention.

Various changes may be made to the invention described, and equivalents (whether recited herein or not included for the sake of some brevity) may be substituted without departing from the true spirit and scope of the invention. Also, any optional feature of the inventive variations may be set forth and claimed independently or in combination with any one or more of the features described herein. Accordingly, the invention contemplates combinations of various aspects of the embodiments or combinations of the embodiments themselves, where possible. Reference to a singular item includes the possibility that there are plural of the same items present. More specifically, as used herein and in the appended claims, the singular forms "a," "and," "said," and "the" include plural references unless the context clearly dictates otherwise.

It is important to note that where possible, aspects of the various described embodiments, or the embodiments themselves can be combined. Where such combinations are intended to be within the scope of this disclosure.

The invention claimed is:
1. A medical tubing comprising:
a tubular body having an axis extending lengthwise, the tubular body having multiple regions including at least a first region, where the multiple regions extend along the axis and each have a wall formed from a plurality of material sections that extend spirally along the axis;
the plurality of material sections including a reinforcement material section next to an adjacent material section, where the reinforcement material section and the adjacent material section extend in a continuous spiral over the multiple regions; and
wherein the reinforcement material section comprises a first hardness in the first region and decreases in each of the multiple regions in a distal direction along the tubular body, where the plurality of material sections are configured such that the tubular body increases in flexibility towards the distal direction, and where a second hardness of the adjacent material section is less than the first hardness;
wherein in the first region the reinforcement material section comprises a first structural dimension and in a second region the reinforcement material section comprises a second structural dimension that is less than the first structural dimension, a stepdown region of the reinforcement material section that is located between the first region and the second region having a third structural dimension, where the first structural dimension and the second structural dimension are constant adjacent to the stepdown region, and where the third structural dimension steps down in the stepdown region from the first structural dimension to the second structural dimension.

2. The medical tubing of claim 1, further comprising an inner liner that is interior to the tubular body.

3. The medical tubing of claim 2, further comprising a reinforcement structure that is exterior to the inner liner.

4. The medical tubing of claim 3, wherein the reinforcement structure is embedded within the wall of at least one of the multiple regions.

5. The medical tubing of claim 1, wherein the plurality of material sections extends in a right-hand wind direction in the first region.

6. The medical tubing of claim 1, wherein the plurality of material sections extends in a left-hand wind direction in the first region.

7. The medical tubing of claim 1, wherein at least one of the plurality of material sections comprises a non-fusable material.

8. The medical tubing of claim 1, further comprising a soft distal tip section.

9. The medical tubing of claim 8, wherein the soft distal tip section comprises a single material.

10. The medical tubing of claim 1, wherein the tubular body comprises a proximal region located proximally to the first region, the proximal region comprising a single material having a polymer chain that extends in a helical pattern over the proximal region.

11. A medical tubing comprising:

a tubular body having an axis extending lengthwise, the tubular body having multiple regions including at least a first region, where the multiple regions extend along the axis and each have a wall formed from a plurality of material sections that extend spirally along the axis;

the plurality of material sections including a reinforcement material section next to an adjacent material section, where the reinforcement material section and the adjacent material section extend in a continuous spiral over the multiple regions; and wherein the reinforcement material section comprises a first hardness in the first region and decreases in each of the multiple regions in a distal direction along the tubular body, where the plurality of material sections are configured such that the tubular body increases in flexibility towards the distal direction, and where a second hardness of the adjacent material section is less than the first hardness;

wherein in the first region the reinforcement material section comprises a first width and a second region the reinforcement material section comprises a second width that is less than the first width, a stepdown region of the reinforcement material section that is located between the first region and the second region, and where the stepdown region steps down from the first width to the second width.

12. The medical tubing of claim 11, further comprising an inner liner that is interior to the tubular body.

13. The medical tubing of claim 12, further comprising a reinforcement structure that is exterior to the inner liner.

14. The medical tubing of claim 13, wherein the reinforcement structure is embedded within the wall of at least one of the multiple regions.

15. The medical tubing of claim 11, wherein the plurality of material sections extends in a right-hand wind direction in the first region.

16. The medical tubing of claim 11, wherein the plurality of material sections extends in a left-hand wind direction in the first region.

17. The medical tubing of claim 11, wherein at least one of the plurality of material sections comprises a non-fusable material.

18. The medical tubing of claim 11, further comprising a soft distal tip section.

19. The medical tubing of claim 18, wherein the soft distal tip section comprises a single material.

20. The medical tubing of claim 11, wherein the tubular body comprises a proximal region located proximally to the first region, the proximal region comprising a single material having a polymer chain that extends in a helical pattern over the proximal region.

* * * * *